(12) United States Patent
Maynard et al.

(10) Patent No.: US 11,879,019 B2
(45) Date of Patent: *Jan. 23, 2024

(54) DUAL-ENZYME RESPONSIVE PEPTIDES

(71) Applicant: THE REGENTS OF THE UNIVERSITY OF CALIFORNIA, Oakland, CA (US)

(72) Inventors: Heather D. Maynard, Los Angeles, CA (US); Natalie Boehnke, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1026 days.

This patent is subject to a terminal disclaimer.

(21) Appl. No.: 16/469,452

(22) PCT Filed: Dec. 19, 2017

(86) PCT No.: PCT/US2017/067284
§ 371 (c)(1),
(2) Date: Jun. 13, 2019

(87) PCT Pub. No.: WO2018/118902
PCT Pub. Date: Jun. 28, 2018

(65) Prior Publication Data
US 2020/0199177 A1     Jun. 25, 2020

Related U.S. Application Data

(60) Provisional application No. 62/558,566, filed on Sep. 14, 2017, provisional application No. 62/436,147, filed on Dec. 19, 2016.

(51) Int. Cl.
*C07K 5/02* (2006.01)
*A61K 47/65* (2017.01)
*C07K 7/02* (2006.01)
*C12P 21/06* (2006.01)

(52) U.S. Cl.
CPC ........... *C07K 5/0215* (2013.01); *A61K 47/65* (2017.08); *C07K 7/02* (2013.01); *C12P 21/06* (2013.01)

(58) Field of Classification Search
None
See application file for complete search history.

(56) References Cited

U.S. PATENT DOCUMENTS

| | | |
|---|---|---|
| 5,037,883 A | 8/1991 | Kopecek |
| 8,920,836 B2 | 12/2014 | Hayes |
| 8,962,266 B2 | 2/2015 | Kirkland |
| 2004/0116348 A1 | 6/2004 | Chau |
| 2012/0183948 A1* | 7/2012 | Howitz ............... C07D 493/10 549/288 |
| 2012/0295834 A1 | 11/2012 | Jenkins et al. |
| 2013/0330409 A1 | 12/2013 | Mohammad |
| 2014/0121152 A1 | 5/2014 | Jenkins et al. |
| 2014/0206597 A1 | 7/2014 | Jenkins et al. |
| 2014/0335550 A1 | 11/2014 | Zhang |

FOREIGN PATENT DOCUMENTS

| | | |
|---|---|---|
| EP | 2663187 A2 | 11/2013 |
| WO | 1992001477 | 2/1992 |
| WO | 2000064486 | 11/2000 |
| WO | 2002056670 A2 | 7/2002 |
| WO | 2006121552 | 11/2006 |
| WO | 2015061503 A1 | 4/2015 |
| WO | 2016115234 A1 | 7/2016 |

OTHER PUBLICATIONS

Boehnke, Natalie, and Heather D. Maynard. "Design of modular dual enzyme-responsive peptides." Peptide Science 108.5 (2017): e23035.
Dijk, Maarten van, et al. "Synthesis and characterization of biodegradable peptide-based polymers prepared by microwave-assisted click chemistry." Biomacromolecules 9.10 (2008): 2834-2843.
Gorske, Benjamin C., et al. "Local and tunable n? p* interactions regulate amide isomerism in the peptoid backbone." Journal of the American Chemical Society 129.29 (2007): 8928-8929.
Huang, Rui, et al. "Multifunctional fluorescent probe for sequential detections of glutathione and caspase-3 in vitro and in cells." Analytical chemistry 85.13 (2013): 6203-6207.
International Searching Authority, International Search Report and Written Opinion for application PCT/US2017/067284, dated May 8, 2018, 16 pages.
Li, Shi-Ying, et al. "A dual-FRET-based fluorescence probe for the sequential detection of MMP-2 and caspase-3." Chemical Communications 51.77 (2015): 14520-14523.
Mulder, Monique PC, et al. "A cascading activity-based probe sequentially targets E1-E2-E3 ubiquitin enzymes." Nature chemical biology 12.7 (2016): 523.
Tucking, Katrin-Stephanie, et al. "Dual Enzyme-Responsive Capsules of Hyaluronic Acid-block-Poly (Lactic Acid) for Sensing Bacterial Enzymes." Macromolecular rapid communications 36.13 (2015): 1248-1254.
Van De Bittner, Genevieve C., Carolyn R. Bertozzi, and Christopher J. Chang. "Strategy for dual-analyte luciferin imaging: in vivo bioluminescence detection of hydrogen peroxide and caspase activity in a murine model of acute inflammation." Journal of the American Chemical Society 135.5 (2013): 1783-1795.
Anja Watzke, et al., "Selective Activity-Based Probes for Cysteine Cathepsins", Angew. Chem. Int. Ed. 2008, 47, 406-409.
Andre Warnecke, et al., "Synthesis, Cleavage Profile, and Antitumor Efficacy of an Albumin-Binding Prodrug of Methotrexate that is Cleaved by Plasmin and Cathepsin B", Arch. Pharm. Chem. Life Sci. 2007, 340, 389-395.

* cited by examiner

*Primary Examiner* — Christina Bradley
(74) *Attorney, Agent, or Firm* — Quarles & Brady LLP

(57) ABSTRACT

An enzyme-responsive peptide and a method off using such enzyme-responsive peptide are disclosed. An enzyme-responsive peptide, the peptide comprising an amino acid having an α-amino group, an α-carboxylic acid group and a ε-amine group, wherein the ε-amine group is covalently bonded with a first group and the α-carboxylic acid is covalently bonded with a second group.

19 Claims, 36 Drawing Sheets

Specification includes a Sequence Listing.

| Condition | Time Subjected | Pass/Fail |
|---|---|---|
| General Test (24°C) | | Pass |
| Microwave | 1 | Pass |
| Microwave | 5 | Pass |
| Microwave | 10 | Burned |
| Microwave | 20 | Burned |
| Oven Heating (260°C) | 15 | Pass |
| Oven Heating (260°C) | 30 | Pass |
| Oven Heating (260°C) | 60 | Pass |
| Cooling (4°C) | 12h | Pass |
| Cooling (4°C) | 24h | Pass |
| Cooling (18°C) | 12h | Pass |
| Cooling (18°C) | 24h | Pass |

SEQ ID NO: 14

Toluene:THF
4-arm PEG-SH

SEQ ID NO: 4

```
                        SEQUENCE LISTING

<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: covalently bonded to side chain of lysine

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: covalently bonded to side chain of lysine

<400> SEQUENCE: 2

Asp Val Glu Asp
1

<210> SEQ ID NO 3
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: covalently bonded to side chain of lysine

<400> SEQUENCE: 3

Ile Glu Pro Asp
1

<210> SEQ ID NO 4
<211> LENGTH: 4
<212> TYPE: PRT
<213> ORGANISM: Artificial Sequence
<220> FEATURE:
<223> OTHER INFORMATION: synthetic
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: covalently bonded to phenylalanine

<400> SEQUENCE: 4

Cys Ala Ala Lys
1

<210> SEQ ID NO 5
<211> LENGTH: 4
<212> TYPE: PRT
<213> ORGANISM: Artificial Sequence
<220> FEATURE:
<223> OTHER INFORMATION: synthetic

<400> SEQUENCE: 5

Asp Glu Asn Asp
1

<210> SEQ ID NO 6
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 6

Asp Xaa Xaa Asp
1

<210> SEQ ID NO 7
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 7

Asp Glu Val Asp
1

<210> SEQ ID NO 8
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 8

Ile Glu Pro Asp
1

<210> SEQ ID NO 9
```

```
<211> LENGTH: 4
<212> TYPE: PRT
<213> ORGANISM: Artificial Sequence
<220> FEATURE:
<223> OTHER INFORMATION: synthetic

<400> SEQUENCE: 9

Cys Ala Ala Lys
1

<210> SEQ ID NO 10
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 10

Asp Val Glu Asp
1
```

DUAL-ENZYME RESPONSIVE PEPTIDES

CROSS-REFERENCE TO RELATED APPLICATION(S)

This application represents the National Phase Entry of International Application PCT/US2017/067284, filed Dec. 19, 2017; which claims benefit of U.S. Provisional Application 62/436,147 filed Dec. 19, 2016, and U.S. Provisional Application 62/558,566 filed Sep. 14, 2017, both of which are incorporated herein by reference for all purposes.

STATEMENT REGARDING FEDERALLY SPONSORED RESEARCH OR DEVELOPMENT

This invention was made with government support under Grant Number HL119893, awarded by the National Institutes of Health. The government has certain rights in the invention.

BACKGROUND OF THE INVENTION

Due to their high selectivity and specificity, enzyme responsive systems are commonly used for diagnostic and drug delivery applications.[1] Though many single enzyme responsive systems show promise in specific targeting, response to more than one enzyme allows for greater target selectivity and indirect enzyme detection, and provides information about cellular environments.[2] For example, caspase-sensitive reporters, which respond to peroxide production or to cancer related matrix metalloproteinases, have been designed to detect cell injury[3] as well as to monitor reactivation of the apoptotic pathway after anticancer therapy delivery, respectively.[2a,4] Small molecule and protein-based probes have also been designed to monitor enzyme cascades, though these often require very specific enzymes, limiting their modularity.[5]

Enzyme responsive systems can also enable selective biodegradation of materials for biomedical applications. By incorporating multiple enzyme cleavage sites, materials will only degrade and release drugs at specific locations in vivo. Many of these systems are responsive to the serine protease trypsin due to its widespread presence throughout the body, including in the digestive tract, and its association with various cancers.[6] For example, trypsin-sensitive sequences have been grafted into enhanced green fluorescent protein to monitor trypsinogen activation in pancreatic cancer cells.[7] Additionally, trypsin responsive sequences have been incorporated into abuse-deterrent opioid formulations, which allow drug release.

Trypsin is a serine protease that cleaves the C-terminus of positively charged amino acids such as lysine[9] but does not cleave if the ε-amine of lysine is acetylated, or masked.[10] Previously, trypsin has been used to indirectly measure histone deacetylase (HDAC) activity by monitoring trypsin digestion of lysine after deacetylation by I-IDAC.[2c,11] Needed in the art are dual-responsive peptides which are only cleavable under multiple enzymes' digestion.

SUMMARY OF THE INVENTION

In one aspect, the present invention discloses an enzyme-responsive peptide. The peptide comprises an amino acid having an α-amino group, an α-carboxylic acid group and a ε-amine group, wherein the ε-amine group is covalently bonded with a first group and the α-carboxylic acid is covalently bonded with a second group.

In one embodiment, the amino acid is a lysine, an arginine, a glutamine or an isoserine. In one embodiment, the amino acid is a lysine.

In one embodiment, the α-amino group is protected by an acyl group. In one embodiment, the α-amino group is protected by an acetyl group.

In one embodiment, the α-amino group is covalently bonded with a peptide. In one embodiment, the peptide comprises a cysteine.

In one embodiment, the second group comprises a cysteine.

In one embodiment, the second group comprise a drug such as a protein, a peptide, a DNA, a siRNA or a small organic molecule.

In one embodiment, the second group comprises a reporter molecule.

In one embodiment, the first group is an enzyme substrate. In one embodiment, the enzyme substrate is a protease selected from the group consisting of a chymotrypsin substrate, a papain substrate, a caspase 8 substrate and a caspase 3 substrate.

In one embodiment, the enzyme-responsive peptide requires digestion by two separate enzymes to cleave the bond between the α-carboxylic acid and the second group to release the second group. In one embodiment, the enzyme-responsive peptide requires digestion by a first enzyme selected from the group consisting of a chymotrypsin, a papain, a caspase 8 and a caspase 3 and subsequently by a second enzyme of trypsin.

In one embodiment, the enzyme-responsive peptide requires digestion by a first enzyme of chymotrypsin and subsequently by a second enzyme of trypsin.

In one embodiment, The enzyme-responsive peptide of claim 1, wherein the enzyme-responsive peptide has a general structure of:

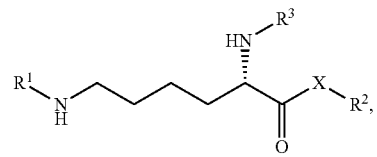

wherein X=O, NH or S; R1=an enzyme substrate; R2=a reporter molecule, an amino acid, a peptide, a polymer, or an active ingredient; and R3=a protecting group, a H, an amino acid or a peptide.

In one embodiment, X=NH.

In one embodiment, $R^1$ is a protease substrate selected from the group consisting of a chymotrypsin substrate, a papain substrate, a caspase 8 substrate and a caspase 3 substrate.

In one embodiment, $R^2$ is a reporter molecule. In one embodiment, the reporter molecule is p-nitrophenol.

In one embodiment, $R^2$ is a peptide. In one embodiment, the peptide comprises a cysteine.

In one embodiment, $R^2$ is an active ingredient.

In one embodiment, $R^3$ is a protecting group. In one embodiment, the protecting group is an acyl group such as an acetyl group.

In one embodiment, the enzyme-responsive peptide requires digestion by two separate enzymes to cleave the bond between the α-carboxylic acid and X—$R^2$ to release X—$R^2$.

In one embodiment, the enzyme-responsive peptide requires digestion by a first enzyme selected from the group consisting of a chymotrypsin, a papain, a caspase 8 and a caspase 3 and subsequently by a second enzyme of trypsin.

In one aspect, the present invention is a polymeric formulation of controlled releasing an active ingredient by using the enzyme as discussed above.

In another aspect, the present invention is a method for controlled releasing an active ingredient. The method comprises the steps of (1) making a compound having a general structure of

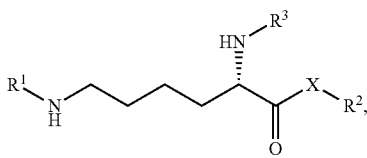

X=O, NH or S; $R^1$=an enzyme substrate; $R^2$=a reporter molecule, an amino acid, a peptide, a polymer, or an active ingredient; and $R^3$=a protecting group, a H, an amino acid or a peptide; (2) contacting the compound with a first enzyme, wherein $R^1$ is cleaved from the compound upon digestion by the first enzyme to form a second compound with a free 6-amine group; and (3) contacting the second compound with a second enzyme, wherein the active ingredient $R^2$—X is released from the second compound upon digestion of the second enzyme.

In one embodiment, $R^1$ is a protease substrate selected from the group consisting of a chymotrypsin substrate, a papain substrate, a caspase 8 substrate and a caspase 3 substrate.

In one embodiment, $R^2$ is a reporter molecule such as p-nitrophenol.

In one embodiment, $R^2$ is a peptide. In one embodiment, the peptide comprises a cysteine.

In one embodiment, $R^2$ is an active ingredient such as a protein, a peptide, a DNA, a siRNA or a small organic molecule.

In one embodiment, $R^3$ is a protecting group such as an acyl group. In one embodiment, the acyl group is an acetyl group.

In one embodiment, the first enzyme is a protease. In one embodiment, the first enzyme is selected from a chymotrypsin, a papain, a caspase 8 and a caspase 3.

In one embodiment, the second enzyme is a protease. In one embodiment, the second enzyme is trypsin.

In one embodiment, the active ingredient is not cleavable before the cleavage of $R^1$ from the compound.

DETAILED DESCRIPTION OF THE INVENTION

In General

Figure 1:
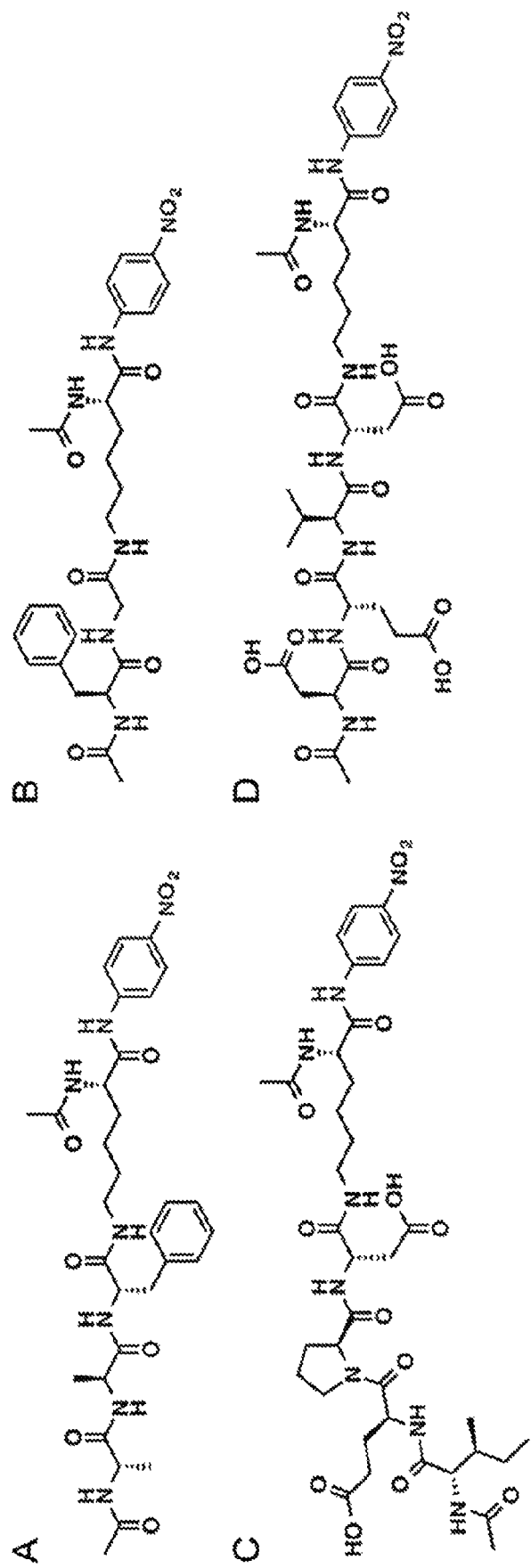
FIGS. 1A-D are a set of chemical compounds showing exemplary structures of chymotrypsin/trypsin sensitive peptide (AcAAF)K-pNA (A), papain/trypsin sensitive peptide (AcFG)K-pNA (B), caspase 8/trypsin sensitive peptide (AcIEPD)K-pNA (SEQ ID NO: 3) (C), and caspase 3/trypsin Sensitive peptide (AcDEVD)K-pNA (SEQ ID NO: 1) (D).

Before the present materials and methods are described, it is understood that this invention is not limited to the particular methodology, protocols, materials, and reagents described, as these may vary. It is also to be understood that the terminology used herein is for the purpose of describing particular embodiments only and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

I. Definitions

Unless defined otherwise, all technical and scientific terms used herein have the same meaning as commonly understood by one of ordinary skill in the art to which this invention belongs. As used herein the following terms have the following meanings.

The term "comprising" or "comprises," as used herein, is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about," when used before a numerical designation, e.g., temperature, time, amount, and concentration, including range, indicates approximations which may vary by (+) or (—) 10%, 5% or 1%.

The term "amino-protecting group," as used herein, refers to a substituent that protects an amino functionality against undesirable reactions during synthetic procedures. Amino-protecting groups are typically acyl, urea, urethane, nitroso, nitro, sulphenyl, sulphonyl, sulfonic acid, or trialkylsilyl. Examples include acetyl, carbobenzyloxy (also benzyloxycarbonyl or carbobenzoxy), formyl, t-butyloxycarbonyl, fluorenylmethyloxycarbonyl, 2-nitrophenylsulfenyl, methanesulfonyl, 4-toluenesulfonyl, and the like. A thorough discussion of amino-protecting groups disclosed in Protective Groups in Organic Synthesis, John Wiley & Sons, N Y, 1981, by T. W. Greene and P. G. M. Wuts, which is incorporated herein by reference.

The term "functional group," as used herein, refers to any of numerous combinations of atoms that form parts of chemical molecules, that undergo characteristic reactions themselves, and that influence the reactivity of the remainder of the molecule. Typical functional groups include, but are not limited to, hydroxyl, carboxyl, aldehyde, carbonyl, amino, azide, alkynyl, thiol and nitril. Potentially reactive functional groups include, for example, amines, carboxylic acids, alcohols, double bonds, and the like. Preferred functional groups are potentially reactive functional groups of amino acids such as amino groups or carboxyl groups.

The term "enzyme" and "enzymes," as used herein, refers generally to proteins that can catalyze biochemical reactions. Enzymes may be proteins that generally enable chemical transformations of organic compounds. Enzymes may be powerful catalysts and they are highly specific. Preferably the enzymes may be selected from the group consisting of lyases, hydrolases, oxidoreductases, transferases, isomerases, and ligases, and combinations thereof. In general, six classes or types of enzymes (as classified by the type of reaction that is catalyzed) may be recognized. For example, enzymes catalyzing reduction/oxidation or redox reactions may be referred to generally as EC 1 (Enzyme Class 1) Oxidoreductases. Enzymes catalyzing the transfer of specific radicals or groups may be referred to generally as EC2 (Enzyme Class 2) Transferases. Enzymes catalyzing hydrolysis may be referred to generally as EC 3 Hydrolases. Enzymes catalyzing removal from or addition to a substrate of specific chemical groups may be referred to generally as EC 4 Lyases. Enzymes catalyzing isomerization may be referred to generally as EC 5 Isomerases. Enzymes catalyzing combination or binding together of substrate units may be referred to generally as EC 6 Ligases. Hydrolase enzymes may include, but are not limited to, a lipase, a phosphatase, an amylase, a cellulase, a protease, a peptidase, a urease, or a deaminase.

Enzymes such as amylases and proteases may break down large molecules (starch or proteins, respectively) into smaller ones, so they can be absorbed by the intestines. Starch molecules, for example, may be too large to be absorbed from the intestine, but enzymes may hydrolyze the starch chains into smaller molecules such as maltose and eventually glucose, which can then be absorbed. Different enzymes may digest different food substances. For example, in ruminants, which have herbivorous diets, microorganisms in the gut produce another enzyme, cellulase, to break down the cellulose cell walls of plant fiber.

The term "trypsin," as used herein, refers to a serine protease from the PA clan superfamily, which can be found in the digestive system of many vertebrates. A trypsin can hydrolyze proteins. Trypsin may be formed in the small intestine when its proenzyme form, the trypsinogen produced by the pancreas, is activated. Trypsin may cleave peptide chains mainly at the carboxyl side of the amino acids lysine or arginine, except when either is followed by proline. It is used for numerous biotechnological processes. The process is commonly referred to as trypsin proteolysis or trypsinisation, and proteins that have been digested/treated with trypsin are said to have been trypsinized.

The term "chymotrypsin," as used herein, refers to a digestive enzyme component of pancreatic juice acting in the duodenum where it may perform proteolysis, the breakdown of proteins and polypeptides. Chymotrypsin may preferentially cleave peptide amide bonds where the carboxyl side of the amide bond (the P1 position) is a large hydrophobic amino acid (tyrosine, tryptophan, and phenylalanine). These amino acids may contain an aromatic ring in their sidechain that fits into a 'hydrophobic pocket' (the Si position) of the enzyme. A chymotrypsin may be activated in the presence of trypsin. The hydrophobic and shape complementarity between the peptide substrate P1 sidechain and the enzyme Si binding cavity accounts for the substrate specificity of this enzyme. Chymotrypsin may also hydrolyze other amide bonds in peptides at slower rates, particularly those containing leucine and methionine at the P1 position. Structurally, it is the archetypal structure for its superfamily, the PA clan of proteases.

Chymotrypsin, as a digestive protease, may be produced in inactive form as chymotrypsinogen in the pancreas and transported in this form to the stomach where it can be activated. This stops the enzyme from digesting the pancreas or other tissues before it enters the gut. This type of inactive precursor to an enzyme is known as a zymogen or proenzyme.

The term "papain" or "papaya proteinase I," as used herein, refers to a cysteine protease enzyme present in papaya (*Carica papaya*) and mountain papaya (*Vasconcellea cundinamarcensis*). Papain belongs to a family of related proteins with a wide variety of activities, including endopeptidases, aminopeptidases, dipeptidyl peptidases and enzymes with both exo- and endo-peptidase activity.

In one embodiment, papain refers to any enzyme of the papain family of thiol proteases derived from plants which is capable of exerting debriding activity in vitro and in vivo. Papain may be a sulfhydryl protease derived from the *Carica papaya* latex. Native pure papain may be partially reactive until activated upon by mild reducing agents such as cysteine, at the free SH functional group thereof. Papain may be commercially provided as partially purified crystalline form or crude papain, the latter being a mixture comprising papain, chymopapain and lysozyme. According to the principles of the present invention, the term papain refers to papain having an activity within the range of 10,000 to 100,000 US units per mg protein, wherein one USP unit of papain activity is that which releases an equivalent of 1 mg of tyrosine from a casein substrate solution as described in the United States Pharmacopeia reference guide.

The term "caspase 3," as used herein, refers to a caspase protein that interacts with caspase-8 and caspase-9. It may be encoded by the CASP3 gene. CASP3 orthologs have been identified in numerous mammals for which complete genome data are available. Unique orthologs may be also present in birds, lizards, lissamphibians, and teleosts.

The CASP3 protein is a member of the cysteine-aspartic acid protease (caspase) family. Sequential activation of caspases may play a central role in the execution-phase of cell apoptosis. Caspases may exist as inactive proenzymes that undergo proteolytic processing at conserved aspartic residues to produce two subunits, large and small, that dimerize to form the active enzyme. This protein may cleave and activates caspases 6 and 7; and the protein itself may be processed and activated by caspases 8, 9, and 10. It is the predominant caspase involved in the cleavage of amyloid-beta 4A precursor protein, which is associated with neuronal death in Alzheimer's disease. Alternative splicing of this gene may result in two transcript variants that encode the same protein.

In one embodiment, caspase 3 may refer to mammalian caspase-3 protein and biologically active fragments thereof.

Caspase-3 is a serine protease which is capable of cleaving other polypeptides and/or proteins and is also known as CPP32, Yama and apopain. Caspase-3 may cleave most efficiently at the cleavage motif DEND (SEQ ID NO: 5) but is also capable of cleaving at other sites (including those with a DXXD (SEQ ID NO: 6) motif), albeit with lower efficiency. As is known in the art, caspase-3 may be synthesized as a proenzyme comprising a N-terminal peptide (PRO-domain) and two sub-units (see review by Cohen, G. M., Biochem. J., (1997) 326:1-16). The PRO-domain may be cleaved off the proenzyme to provide active caspase-3. Both the pro-form and various active form(s) of the protein are, therefore, encompassed by the term "caspase-3." In the human enzyme, the proposed cleavage site for the PRO-domain may be either Asp-9 or Asp-28, or both. Formation of the two sub-units of active caspase-3 may be proposed to take place by an additional cleavage at amino acid residue Asp-175. Further processing may take place in one or both of the subunits. Thus, the active form of caspase-3 may comprise a single polypeptide, two or more sub-unit polypeptides, or a mixture of these components. For example, many caspases may be active as a heterotetramer comprising two of each subunit. The term "caspase-3 signaling pathway," as used herein, refers to the cellular signaling pathway that is mediated by the caspase-3 protein and which ultimately affects cell differentiation.

The term "peptide," as used herein, encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to, N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), a-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

The term "amino acid" or "amino acids," as used herein throughout, is understood to include the 20 naturally occurring amino acids; those amino acids often modified post-translationally in vivo, including, for example, hydroxyproline, phosphoserine and phospho threonine; and other unusual amino acids including, but not limited to, 2-aminoadipic acid, hydroxylysine, isodesmosine, nor-valine, nor-leucine and ornithine. The term "amino acid" as used herein includes both D- and L-amino acids.

The term "protecting group," as used herein, refers to well-known functional groups which, when bound to a functional group, render the resulting protected functional group inert to the reaction conditions to be conducted on other portions of the compound and which, at the appropriate time, can be reacted to regenerate the original functionality. The identity of the protecting group is not critical and is selected to be compatible with the remainder of the molecule. In one embodiment, the protecting group is an "amino protecting group" which protects the amino functionality of amino acids during the reactions described herein. Examples of conventional amino protecting groups include, for instance, benzyl, acetyl, oxyacetyl, carboxybenzyl (Cbz), Boc, Fmoc, and the like. In another embodiment, the protecting group is a "hydroxy protecting group" which protects the hydroxyl functionality of amino acids. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, Protective Groups in Organic Synthesis, 2d Ed., 1991, John Wiley & Sons, and McOmie Protective Groups in Organic Chemistry, 1975, Plenum Press.

In one embodiment, the protecting group is a "thiol protecting group" which protects the S—H functionality of the thiols during the reactions described herein. Examples of conventional thiol protecting groups include, for instance, thioether, thioester, disulfide, p-methoxybenzyl (Mob), trityl (Trt), acetamidomethyl (Acm), tert-butyl and triphenylmethyl groups or others.

The term "enzyme responsive peptide" or "enzyme cleavable peptide," as used herein, refers to a peptide having one or more specific bonds that can be cleaved under an enzyme's digestion. In one embodiment, the bond[s] of enzyme responsive peptide may be cleaved by a protease. In one embodiment, the protease is selected from the group consisting of trypsin, chymotrypsin, papain and caspase 3.

The term "dual enzyme-responsive peptide" or "dual enzyme-cleavable peptide," refers to a peptide having one or more specific bonds that can be cleaved only under the digestive process of two (or more) different enzymes. In one embodiment, the enzyme is a protease. In one embodiment, the protease is selected from the group consisting of trypsin, chymotrypsin, papain and caspase 3. In one embodiment, the dual enzyme system is selected from the group consisting of trypsin/chymotrypsin, trypsin/papain, and trypsin/caspase 3.

The term "self-immolative linker," as used herein, refers to any linker molecule which cyclizes upon itself when an enzyme cleaves at the C-terminus of the lysine of the enzyme-responsive peptide-drug complex so that an unmodified drug is released. It is important to include a self-immolative linker in the complex because one does not need to modify a drug for the present invention. Many drugs may be applicable in the present invention and unmodified drugs could be released from a complex according to certain embodiments of the present invention. In one embodiment, the self-immolative linker is a methylaminoethylamine linker. Applicants envision that other self-immolative linker may also be used to release an unmodified drug from the complex of the present invention.

In one embodiment, a drug may be attached covalently to the complex without any self-immolative linker. In another embodiment, a drug may be attached covalently to the complex with one self-immolative linker so that an unmodified drug may be released. Example 5 and Scheme 6 show an exemplary self-immolative linker in one non-crushable cross-linked polymer for non-abusable formulation.

The term "alkyl," as used herein, refers to both a saturated aliphatic branched or straight-chain monovalent hydrocarbon having the specified number of carbon atoms. Thus, "(C1-C6) alkyl" means a hydrocarbon having from 1-6 carbon atoms in a linear or branched arrangement. Examples of "(C1-C6) alkyl" include, for example, n-propyl, iso-propyl, n-butyl, iso-butyl, sec-butyl, t-butyl, -pentyl, -hexyl, 2-methylbutyl, 2-methylpentyl, 2-ethylbutyl, 3-methylpentyl, and 4-methylpentyl. Alkyl can be optionally substituted with halogen, —OH, oxo, (C1-C6)alkyl, (C1-C6)alkoxy, (C1-C6) alkoxy(C1-C4)alkyl, aryl, heteroaryl, heterocyclyl, cycloalkyl, carbocyclyl, nitro, cyano, amino, acylamino, or carbamyl, —C(O)O(C1-C6)alkyl, or —C(O)(C1-C6)alkyl.

The term "alkenyl," as used herein, refers to a straight-chain or branched alkyl group having one or more carbon-carbon double bonds. Thus, "(C2-C6) alkenyl" means a hydrocarbon having 2-6 carbon atoms in a linear or branched arrangement having one or more double bonds. Examples of alkenyl groups include, but are not limited to, ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene).

The term "alkynyl," as used herein, refers to a straight-chain or branched alkyl group having one or more carbon-carbon triple bonds. Thus, "(C2-C6) alkynyl" means a hydrocarbon having 2-6 carbon atoms in a linear or branched arrangement having one or more triple bonds. Examples of alkynyl groups include, but are not limited to, ethynyl, propynyl, butynyl, pentynyl, and the like. The one or more carbon-carbon triple bonds can be internal (such as in 2-butyne) or terminal (such as in 1-butyne).

The term "alkoxy", as used herein, refers to an "alkyl-O—" group, wherein alkyl is defined above. Examples of alkoxy group include methoxy or ethoxy groups.

The terms "halogen" or "halo," as used herein, refer to fluorine, chlorine, bromine or iodine.

The term "aryl," as used herein, refers to an aromatic monocyclic or polycyclic (e.g., bicyclic or tricyclic) carbocyclic ring system. Thus, "(C6-C18) aryl" is a 6-18 membered monocyclic or polycyclic system. Aryl systems include optionally substituted groups such as phenyl, biphenyl, naphthyl, phenanthryl, anthracenyl, pyrenyl, fluoranthyl or fluorenyl. An aryl can be optionally substituted. Examples of suitable substituents on an aryl include halogen, hydroxyl, (C1-C12) alkyl, (C2-C6) alkenyl, (C2-C6) alkynyl, (C1-C6) haloalkyl, (C1-C3) alkylamino, (C1-C3) dialkylamino (C1-C6) alkoxy, (C6-C18) aryloxy, (C6-C18) arylamino, (C6-C18) aryl, (C6-C18) haloaryl, (5-12 atom) heteroaryl, —NO2, —CN, —OF3 and oxo.

In some embodiments, a (C6-C18) aryl is phenyl, indenyl, naphthyl, azulenyl, heptalenyl, biphenyl, indacenyl, acenaphthylenyl, fluorenyl, phenalenyl, phenanthrenyl, anthracenyl, cyclopentacyclooctenyl or benzocyclooctenyl. In some embodiments, a (C6-C18) aryl is phenyl, naphthalene, anthracene, 1H-phenalene, tetracene, and pentacene.

The term "heteroaryl," as used herein, refers aromatic groups containing one or more atoms is a heteroatom (O, S, or N). A heteroaryl group can be monocyclic or polycyclic, e.g., a monocyclic heteroaryl ring fused to one or more carbocyclic aromatic groups or other monocyclic heteroaryl groups. The heteroaryl groups of this invention can also include ring systems substituted with one or more oxo moieties. Examples of heteroaryl groups include, but are not limited to, thiophenyl, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. In other embodiments, a 5-20-membered heteroaryl group is pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, benzothienyl.

The term "haloalkyl," as used herein, includes an alkyl substituted with one or more F, Cl, Br, or I, wherein alkyl is defined above.

The term "haloaryl," as used herein, includes an aryl substituted with one or more F, Cl, Br, or I, wherein aryl is defined above.

The term "hetero," as used herein, refers to the replacement of at least one carbon atom member in a ring system with at least one heteroatom selected from N, S, or O.

"Hetero" also refers to the replacement of at least one carbon atom member in a acyclic system. A hetero ring system or a hetero acyclic system may have 1, 2, or 3 carbon atom members replaced by a heteroatom.

The terms "heterocyclyl" or "heterocyclic," as used herein, refer to a saturated or unsaturated group having a single ring or multiple condensed rings, from 1 to 10 carbon atoms and from 1 to 4 heteroatoms selected from nitrogen, sulfur or oxygen. In fused ring systems, one or more of the rings can be aryl or heteroaryl, provided that the point of attachment is at the heterocyclyl. Heterocyclyl can be unsubstituted or substituted in accordance with cycloalkyl.

The term "oxo," as used herein, refers to =O. When an oxo group is a substituent on a carbon atom, they form a carbonyl group (C(O)).

The term "Naltrexone," as used herein, refers to a medication (sold under the brand names REVIA and VIVITROL among others) primarily used to manage alcohol dependence and opioid dependence. It may also be called N-Cyclopropyl-methylnoroxymorphone, N-Cyclopropylmethyl-14-hydroxydihydro-morphinone, or 17-(Cyclopropylmethyl)-4,5α-epoxy-3,14-dihydroxymorphinan-6-one. In opioid dependence, Naltrexone may not be started until people are detoxified. Naltrexone may be taken by mouth or by injection into a muscle. Effects may begin within 30 minutes. A decreased desire for opioids however may take a few weeks. In one embodiment of the present invention, naltrexone is used as a model drug due to its structural similarity to opioids.

In one embodiment, the present disclosure reveals a dual-responsive peptide or method of using the peptide for controlled releasing a medication such as an opioid which has similar structure to naltrexone.

The term "opioid," as used herein, refers to a natural (e.g. morphine), semi-synthetic (e.g. buprenorphine) or synthetic (e.g. meptazinol) drug that acts by binding to one or more of the opioid receptors in the brain, thus displacing an endogenous analgesic ligand, namely an enkephalin or endorphin, and having a therapeutically useful pain-relieving effect. Opioids may include, but not limited to, oxycodone, morphine, fentanyl, hydrocodone, tapentadol, methadone, hydromorphone, meperidine, codeine and others, along with opiate antagonists such as buprenorphine, naloxone and naltrexone. The prescription names of these compounds can be found at http://www.rehabcenter.net/list-opioids-united-states/.

In one embodiment, the present disclosure reveals a dual enzyme-responsive peptide or method of using the peptide for controlled releasing a drug or a medicine to prevent abuse of the drug. The present disclosure is suitable for many drug or medicine such as small molecule drugs or large biomolecular drugs (e.g., proteins, peptides, DNAs, RNAs). For example, a dual enzyme-responsive peptide can be used to stabilize proteins or peptides in the stomach of a subject and controlled release them when needed. Applicants envision that many other drugs or medicines can be conjugated to the dual enzyme-responsive peptide for controlled delivery to the subject. In one embodiment, the drug or medicine is an opioid.

The term "PDMS," as used herein, refers to polydimethylsiloxane.

The term "PEG," as used herein, refers to polyethylene glycol.

The term "Fmoc," as used herein, refers to fluorenylmethyloxycarbonyl.

The term "DIPEA," as used herein, refers to N,N-diisopropylethylamine.

The term "DMF," as used herein, refers to dimethylformamide.

The term "TFA," as used herein, refers to trifluoroacetic acid.

The term "DCM," as used herein, refers to dichloromethane.

The term "ESI-MS," as used herein, refers to electrospray ionization-mass spectrometry.

The term "HBTU," as used herein, refers to 2-(1H-benzotriazol-1-yl)-1,1,3,3-tetramethyluronium hexafluorophosphate.

The term "HPLC," as used herein, refers to high-performance liquid chromatography.

The term "DME," as used herein, refers to dimethoxyethylene glycol.

The term "MeCN," as used herein, refers to acetonitrile.

The term "DIEA," as used herein, refers to diisopropylethylamine.

The term "TIPS," as used herein, refers to triisopropylsilane.

The term "t-BOC" or "BOC," as used herein, refers to ter-butyloxycarbonyl.

The term "TEA," as used herein, refers to triethylamine.

The term "Ac," as used herein, refers to acetyl.

The term "HOBt," as used herein, refers to 1-hydroxybenzotriazole.

The term "HEPES," as used herein, refers to 4-(2-Hydroxyethyl)piperazine-1-ethanesulfonic acid.

The term "DMSO," as used herein, refers to dimethyl sulfoxide.

The term "EDTA," as used herein, refers to ethylenediaminetetraacetic acid.

The term "trityl," as used herein, refers to triphenylmethyl.

The term "TCEP," as used herein, refers to Tris(2-carboxyethyl)phosphine.

The term "KHMDS," as used herein, refers to potassium bis(trimethylsilyl)amide.

The term "OECD," as used herein, refers to Organization for Economic Cooperation and Development.

The term "ALT," as used herein, refers to alanine aminotransferase.

The term "AST," as used herein, refers to aspartate aminotransferase.

The term "BUN," as used herein, refers to blood urea nitrogen.

The term "Creat," as used herein, refers to creatinine.

The term "natural amino acid," as used herein, refers to any one of the 20 amino acids used for protein biosynthesis as well as other amino acids which can be incorporated into proteins during translation (including pyrrolysine and selenocysteine). The 20 natural amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine and lysine.

The term "non-natural amino acid," as used herein, refers to an organic compound that is not among those encoded by the standard genetic code, or incorporated into proteins during translation. Therefore, non-natural amino acids may include amino acids or analogs of amino acids, but are not limited to, the D-isostereomers of amino acids, the beta-amino-analogs of amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, 7-amino butyric acid, and derivatives thereof wherein the amine nitrogen has been mono- or di-alkylated.

The term "lysine," as used herein, refers to an α-amino acid that is used in the biosynthesis of proteins. Lysine may contain an α-amino group (which is in the protonated —$NH_3^+$ form under biological conditions), an α-carboxylic acid group (which is in the deprotonated —COO— form under biological conditions), and a side chain lysyl (($CH_2)_4$ $NH_2$), classifying it as a charged (at physiological pH), aliphatic amino acid. Lysine may be essential in humans, meaning the body cannot synthesize it and thus it must be obtained from the diet.

The disclosure reveals multiple-responsive peptides which include bonds only cleavable under multiple enzymes' digestion and methods of using the peptides. For example, the disclosure reveals dual-responsive peptides which are only cleavable under two enzymes' digestion and methods of using these peptides.

The disclosure aims at controlled releasing chemical or biological substances such as a medicine or a drug at a specific location within the body of a subject. For example, multiple enzyme-responsive peptides or dual enzyme-responsive peptides are covalently bonded with a medicine or a drug, which may be controlled released at certain locations of the subject's body in vivo, such as the digestive tract.

The present disclosure reveals formulations comprising multiple enzyme-responsive peptides or dual enzyme-responsive peptides for controlled releasing a medicine or a drug. In another embodiment, the present disclosure may also be used in abuse-deterrent opioid formulations, which allow drug controlled release.

The terms "subject" or "patient," as used herein, refers to any animal, such as a dog, cat, bird, livestock, and particularly a mammal, preferably a human. In some instances, the subject may also be a "user" (and thus the user is also the subject or patient).

In one embodiment, dual enzyme-responsive peptides are synthesized masking the ε-amine of lysine with various enzyme substrates. Enzymatic cleavage of these sequences may unmask the ε-amine, allowing for further digestion by a second enzyme, which may be monitored colorimetrically. Specifically, a dual enzyme-responsive peptide system of the present disclosure requires sequential digestion by two enzymes for cargo release from system, such as the C-terminus of the dual enzyme-responsive peptide. For example, a first enzyme may cleave the peptide to unmask the recognition site and a second enzyme may subsequently digest and cleave another bond of the peptide to controlled release of the target compound, such as a medicine or a drug.

Throughout the disclosure, Applicants use lysine as a model system. Other amino acids such as arginine, glutamine and isoserine can be used in the same way as that of lysine. For example, dual enzyme-responsive peptides can be made by using arginine, glutamine or isoserine instead of lysine.

The term "carrier," as used herein, refers to a pharmaceutically acceptable solid or liquid filler, diluent or encapsulating material. A water-containing liquid carrier may contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials.

Many materials may serve as pharmaceutically acceptable carriers. For example, the pharmaceutically acceptable carriers may include sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator.

The term "stabilization agent," as used herein, refers to any suitable agent that can stabilize the peptides or formulations. For example, an approach for stabilizing solid peptide formulations of the invention is to increase the physical stability of purified, e.g., lyophilized, peptide. This will inhibit aggregation via hydrophobic interactions as well as via covalent pathways that may increase as proteins unfold. Stabilizing formulations in this context may often include polymer-based formulations, for example a biodegradable hydrogel formulation/delivery system. The critical role of water in protein structure, function, and stability is well known. Typically, proteins are relatively stable in the solid state with bulk water removed. However, solid therapeutic peptide formulations may become hydrated upon storage at elevated humidities or during delivery from a sustained release composition or device. The stability of peptides generally drops with increasing hydration. Water may also play a significant role in solid peptide aggregation, for example, by increasing peptide flexibility resulting in enhanced accessibility of reactive groups, by providing a mobile phase for reactants, and by serving as a reactant in several deleterious processes such as beta-elimination and hydrolysis.

An effective method for stabilizing peptides against solid-state aggregation may be to control the water content in a solid formulation and maintain the water activity in the formulation at optimal levels. This level depends on the nature of the protein, but in general, peptides maintained below their "monolayer" water coverage will exhibit superior solid-state stability.

The term "additive," as used herein, refers to any chemicals such as sugars and other polyols, which may also impart significant physical stability to dry, e.g., lyophilized peptides. These additives may also be used within the invention to protect the proteins against aggregation not only during lyophilization but also during storage in the dry state. For example, sucrose and Ficoll 70 (a polymer with sucrose units) exhibit significant protection against peptide or protein aggregation during solid-phase incubation under various conditions. These additives may also enhance the stability of solid peptides embedded within polymer matrices.

Yet additional additives, for example sucrose, may stabilize peptides against solid-state aggregation in humid atmospheres at elevated temperatures, as may occur in certain sustained-release formulations of the invention. These additives can be incorporated into polymeric melt processes and compositions within the invention. For example, polypeptide microparticles can be prepared by simply lyophilizing or spray drying a solution containing various stabilizing additives described above. Sustained release of unaggregated peptides and proteins can thereby be obtained over an extended period of time.

II. The Invention

The present disclosure relates to peptides, in particular multiple enzyme-responsive peptides such as dual enzyme-responsive peptides and related formulations and methods of using the peptides for controlled releasing a substance such as a medicine or a drug.

In one aspect, the present invention discloses an enzyme-responsive peptide. In one embodiment, the enzyme-responsive peptides are dual enzyme-responsive peptides.

In one embodiment, the dual enzyme-responsive peptide includes one masked site and one protected site, wherein the masked site is covalently bonded with a first substrate to a first enzyme and the protected site is covalently bonded with a substance such as a medicine or a drug, a peptide, a protein, a DNA, or a siRNA. Thus, the first enzyme is required to digest and cleave the first substrate to unmask the masked site. Subsequently, the second enzyme is used to digest and cleave another related bond to controlled release the substance such as a medicine or a drug, a peptide, a protein, a DNA or a siRNA.

In one embodiment, the enzyme-responsive peptide requires digestion by at least two different enzymes for cleaving covalent bond[s] in the enzyme-responsive peptide to release an active ingredient, e.g., a drug. In one embodiment, the enzyme-responsive peptide requires digestion by two different enzymes for cleaving covalent bond[s] in the enzyme-responsive peptide to release an active ingredient, e.g., a drug.

In one embodiment, an enzyme-responsive peptide comprises an amino acid having an α-amino group, an α-carboxylic acid group and a ε-amine group, wherein the ε-amine group is covalently bonded with a first group and the α-carboxylic acid is covalently bonded with a second group.

In one embodiment, the amino acid is a lysine. In another embodiment, the amino acid is a lysine derivative.

In one embodiment, the α-amino group is protected. The α-amino group may be protected by any suitable protecting group as appreciated by one skilled in the art.

For example, in one embodiment, the α-amino group is protected by an acyl group. In one specific embodiment, the α-amino group is protected by an acetyl group.

In one embodiment, the α-amino group is covalently bonded with another functional group. For example, the α-amino group may be covalently bonded with one amino acid.

In one embodiment, the α-amino group may be covalently bonded with at least two amino acids, or a peptide comprising at least two amino acids.

In one embodiment, the α-amino group is covalently bonded with one peptide.

In one embodiment, the amino acid or the peptide which is bonded with the α-amino group may comprise a free thiol group. For example, the peptide a cysteine. The cysteine provides a free thiol group, which provides a cross-linking function to the peptide for bonding with other compounds, functional groups, materials, or polymers.

In one embodiment, the second group, which is covalently bonded with the α-carboxylic acid of the enzyme-responsive peptide, may be an amino acid, a peptide, or an active substance or ingredient such as a medicine or a drug. Many medicines, drugs, biomolecule such as therapeutic peptides, proteins, siRNAs, DNA or diagnostic molecule may be used for the present invention.

In one embodiment, the second group comprises a free thiol group. For example, the second group comprises a cysteine. The first group may be a peptide which comprises a cysteine, provides a linking function to the peptide for bonding with other compounds or functional groups. In one embodiment, there is another free thiol in the enzyme-responsive peptide. The two thiols in the enzyme-responsive peptide provide a cross-linking function to the peptide for bonding with other compounds or functional groups. As such, the enzyme-responsive peptide with two free thiols may be used as a cross-linker.

In one embodiment, the second group comprises a chemical agent or a biological agent which can act as an active agent. For example, the second group comprises a drug such as e.g., an oxycodone, covalently bonded with the α-carboxylic acid of the enzyme-responsive peptide.

In one embodiment, the 6-amine of the enzyme-responsive peptide is covalently bonded with a first group. In one embodiment, the first group is an enzyme substrate such as a protease substrate. The examples of the protease substrate may include chymotrypsin substrate, papain substrate, caspase 8 substrate and caspase 3 substrate.

In one embodiment, the enzyme substrate is a protease substrate selected from the group consisting of a chymotrypsin substrate, a papain substrate, a caspase 8 substrate and a caspase 3 substrate.

In one embodiment, the enzyme-responsive peptide requires digestion by two separate enzymes to release a targeted function group such as a drug. For example, the enzyme-responsive peptide requires digestion by two separate enzymes to cleave the bond between the α-carboxylic acid and the second group to release the second group. The first group may include a drug.

Alternatively, the enzyme-responsive peptide requires digestion by two separate enzymes to cleave the bond between the α-amino group and the functional group $R^3$ to release $R^3$. Applicants envision that $R^3$ may comprise a chemical or biological agent which can act as an active ingredient, e.g., a drug.

In one embodiment, depending on the specific protease substrate on the ε-amine, the enzyme-responsive peptide requires digestion by a first enzyme selected from the group consisting of chymotrypsin, papain, caspase 8 and caspase 3 and subsequently by a second enzyme of trypsin. FIG. 1 shows some examples of protease substrates corresponding to chymotrypsin, papain, caspase 8 and caspase 3, which are covalently bonded with dual enzyme-responsive peptides of the present invention.

In another embodiment, Applicants envision the enzyme-responsive peptide may require digestion by two separate enzymes when the enzyme substrates are specifically designed into the enzyme-responsive peptide.

For example, when the major skeleton of the enzyme-responsive peptide is a lysine, the ε-amine of the lysine may be bonded with another protease substrate so that the specific protease is required for digestion by the enzyme-responsive peptide to produce the free ε-amine by releasing the protease substrate first. Subsequently, a trypsin is required for further digestion of the enzyme-responsive peptide to release the targeted active ingredient (e.g., the first group).

As one example, the protease substrate may be a chymotrypsin substrate, a papain substrate, a caspase 8 substrate or a caspase 3 substrate. Thus, digestion of the enzyme-responsive peptide by one protease of chymotrypsin, papain, caspase 8 or caspase 3 may be required before the enzyme-responsive peptide is digested by a trypsin. The enzyme-responsive peptide is a dual enzyme-responsive peptide, which requires two enzyme's digestion to release an active substance such as a medicine or a drug (e.g., the first group). Many medicines, drugs, biomolecule such as therapeutic peptides, proteins, siRNAs, DNA or diagnostic molecule may be used for the present invention.

Applicants envision that a dual enzyme-responsive peptide of the present invention may require any combination of proteases. For example, the dual enzyme-responsive peptide of the present invention may require any combination of proteases of trypsin, chymotrypsin, papain, caspase 8 and caspase 3.

For example, the dual enzyme-responsive peptide of the present invention may include a major skeleton with one specific amino acid or peptide which is a substrate corresponding to a first specific protease. Subsequently, the dual enzyme-responsive peptide may be further designed to include a second specific amino acid or peptide which is a substrate to the second protease. As such, the dual enzyme-responsive peptide would require digestion of the second protease first which can release the substrate to the first protease. Subsequently, a first protease may be used for digestion of the dual enzyme-responsive peptide to release the targeted active ingredient. As such, many combinations of the dual enzyme-responsive peptides may be produced by the present invention, which may require many combination of the proteases for digestion.

Applicants further envision that the present invention may be applicable to produce an enzyme-responsive peptide which requires digestion of more than two enzymes. For example, a triple or a quadruple enzyme-responsive peptide may be produced by using the same method as discussed herein of the present invention.

In one embodiment, an enzyme-responsive peptide of the present invention has a general structure of:

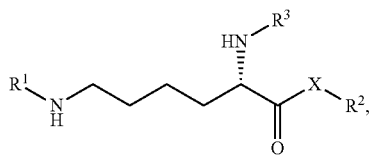

wherein X=O, NH or S; $R^1$=a first enzyme substrate; $R^2$=a reporter molecule, an amino acid, a peptide, a polymer, or an active ingredient; and $R^3$=a protecting group, a H, an amino acid or a peptide.

In one embodiment, X=NH.
In one embodiment, X=O.
In one embodiment, X=S.

In one embodiment, when $R^1$=a first enzyme substrate, the enzyme-responsive peptide is a dual enzyme-responsive peptide, which requires two separate proteases (such as a first protease of chymotrypsin, papain, caspase 8 or caspase 3 and a second protease of trypsin) for digestion.

In one embodiment, $R^1$ is a protease substrate selected from the group consisting of a chymotrypsin substrate, a papain substrate, a caspase 8 substrate and a caspase 3 substrate. As such, a dual enzyme-responsive peptide requires a first digestion of a chymotrypsin, a papain, a caspase 8 or a caspase 3 to release a free ε-amine. A second digestion by trypsin is then required to release $R^2$, which can be an active ingredient.

In one embodiment, $R^2$ is a reporter molecule. The reporter molecule may be any aromatic compound such as p-nitrophenol.

In another embodiment, $R^2$ is an amino acid or a peptide.

In one embodiment, $R^2$ is a peptide. In one specific embodiment, the peptide comprises a free thiol group. For example, the peptide comprises a cysteine. The free thiol group of the cysteine provides further bonding functionality to the enzyme-responsive peptide. For example, when more than two free thiols are present in the enzyme-responsive peptide, the enzyme-responsive peptide may be used as a cross-linker.

In another embodiment, $R^2$ is a chemical or biological agent, which can act as an active ingredient, such as a drug or a medicine. Many medicines, drugs, biomolecule such as therapeutic peptides, proteins, siRNAs, DNA or diagnostic molecule may be used for the present invention. In one specific embodiment, the active ingredient of $R^2$ can be released from the enzyme-responsive peptide under a specific condition, such as the digestive tract, in the stomach or intestine of a subject.

In one embodiment, $R^3$ is a protecting group.

$R^3$ can be any protecting group which can protect a free amine.

In one embodiment, $R^3$ is an acyl group such as an acetyl group.

In one embodiment, $R^3$ is a H.

In another embodiment, $R^3$ is an amino acid or a peptide.

In one embodiment, the enzyme-responsive peptide is a multiple enzyme-responsive peptide and the multiple enzyme-responsive peptide requires digestion by at least two separate enzymes to cleave the bond between the α-carboxylic acid and X—$R^2$ to release X—$R^2$.

In one embodiment, the enzyme-responsive peptide is a dual enzyme-responsive peptide and the enzyme-responsive peptide requires digestion by two separate enzymes to cleave the bond between the α-carboxylic acid and X—$R^2$ to release X—$R^2$.

In another embodiment, the enzyme-responsive peptide requires digestion by two separate enzymes to cleave the bond between the ε-amino group and the functional group R' to release $R^1$ and the bond between the α-carboxylic acid and X—$R^2$ to release X—$R^2$. Applicants envision that IV or $R^2$ may comprise a chemical or biological agent which can act as an active ingredient such as a drug.

In one embodiment, the enzyme-responsive peptide requires digestion by a first enzyme selected from the group consisting of chymotrypsin, a papain, caspase 8 and caspase 3 and subsequently by a second enzyme, wherein the second enzyme is trypsin.

In one aspect, the present invention discloses a formulation or a composition comprising any of the enzyme-responsive peptides as discussed above.

The formulation may further include other components. For example, a formulation or a composition including the enzyme-responsive peptides may further comprise a carrier, a diluent or filler, a binder, a sweetener, a flavoring agent, a solvent, a lubricant, or any other components suitable for a pharmaceutical formulation.

For example, the formulation of the enzyme-responsive peptides may further comprise a pharmaceutically acceptable solid or liquid filler, diluent or encapsulating material, pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials.

The formulation of the enzyme-responsive peptides may further comprise stabilization agents that stabilize the peptides or formulations. The formulation of the enzyme-responsive peptides may be either in solid form or in liquid form.

The formulation of the enzyme-responsive peptides may further comprise any additive that may also impart significant physical stability to dry, e.g., lyophilized peptides.

Various additional preparative components and methods, as well as specific formulation additives, are provided herein which yield formulations for peptides, wherein the peptide is stabilized in a substantially pure, unaggregated form using a solubilization agent. A range of components and additives are contemplated for use within these methods and formulations. Exemplary of these solubilization agents are cyclodextrins (CDs), which selectively bind hydrophobic side chains of polypeptides. These CDs have been found to bind to hydrophobic patches of proteins in a manner that significantly inhibits aggregation. This inhibition is selective with respect to both the CD and the protein involved. Such selective inhibition of peptide aggregation may provide additional advantages within the intranasal delivery methods and compositions of the invention.

Scheme 1 shows an exemplary structure of the enzyme-responsive peptide.

Specifically, Applicants found that enzyme-responsive peptides require digestion by two separate enzymes for cleavage at the C terminal position of lysine. The first enzyme cleaves the protease substrate that is coupled to the ε-amine of lysine, unmasking the primary amine, allowing for cleavage by a second protease, such as trypsin, that recognizes basic amino acids.

Utilizing this approach, Applicants have demonstrated sequences that are cleaved by trypsin/chymotrypsin, trypsin/papain, trypsin/caspase 8 or trypsin/caspase 3.

The Example and FIG. 1 show one example of enzyme-responsive peptides and methods for making such an enzyme-responsive peptide.

Specifically, Scheme 2 shows one exemplary synthetic procedure for making the enzyme-responsive peptide.

Scheme 2

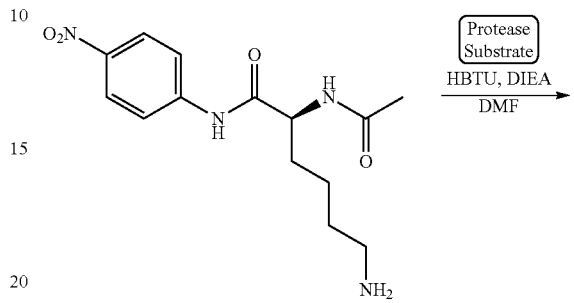

Scheme 1

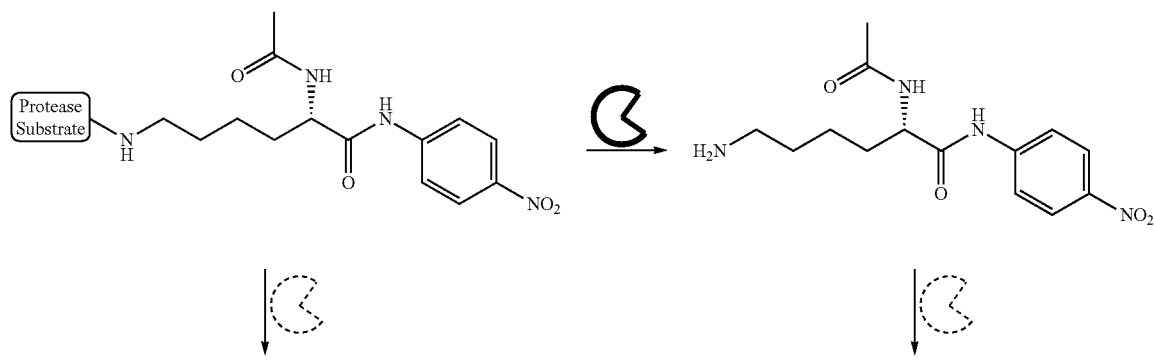

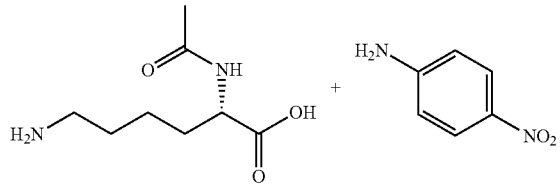

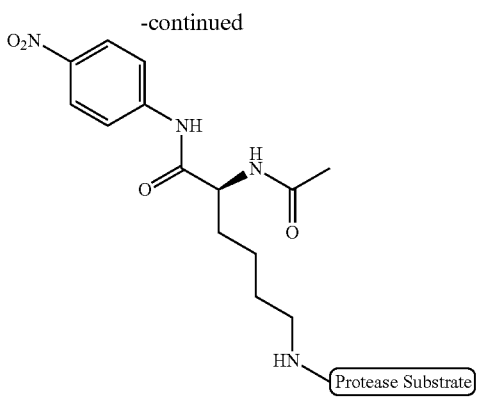

In one embodiment, the protease substrate is selected from the group consisting of Ac-AAF, Ac-F, Ac-FG, Ac-DEVD (SEQ ID NO: 7).

Protease substrates (Ac-AAF, Ac-F, Ac-FG, Ac-DEVD (SEQ ID NO: 7)) may be synthesized using standard fmoc solid-phase chemistry with 2-chlorotrityl chloride resin (0.4 or 1.2 mmol/g substitution).

0.1M HOBt in 20% 4-methylpiperidine in DMF may be used for Fmoc deprotection to reduce aspartimide formation. N-termini may be acetylated prior to cleavage from resin using 50 eq. acetic anhydride and DIEA in DMF for 30 min. Peptides may be cleaved from the resin using 0.5% TFA in DCM.

Reverse coupling to acetylated lysine p-nitroanilide may be carried out in DMF using 3 eq. HBTU and 6 eq. DIEA.

Nitroanilide peptides may be purified either by dissolving in ethyl acetate and washing with saturated $NaHCO_3$, $NH_4Cl$, and brine, or by preparative reverse-phase HPLC equipped with a C18 column using a linear gradient from 95:5 to 5:95 $H_2O$/acetonitrile with 0.1% TFA at a flow rate of 20 ml/min. ESI-MS may be used to confirm the molecular masses of the desired products.

In one embodiment, the dual enzyme-responsive peptides may further include cross-linkers for bonding with other compounds or functional groups. For example, a peptide bonding with the α-amino group may include a cysteine or a thiol group. The functional group bonding with the α-carboxylic acid of the enzyme-responsive peptide may also include a cysteine or a thiol group. These thiol groups provide linking function to the dual enzyme-responsive peptides so that the peptides may be linked to polymers for additional protections or controlled release. FIGS. 12-15 provide formulae showing chemical structures of exemplary dual enzyme cleavable peptides with thiol groups according to embodiments of the present invention.

In another embodiment, the present disclosure reveals a dual enzyme-responsive peptide for controlled releasing a medicine such as Naltrexone.

Example 5 showed the use of a dual enzyme-responsive peptide for controlled releasing Naltrexone with noncrushable cross-linked polymer for non-abusable formulations.

Figure 28:
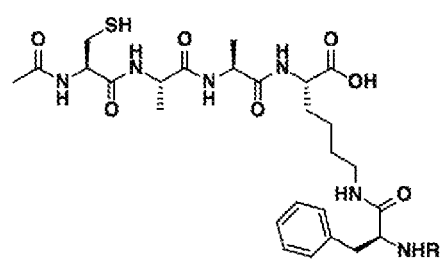
FIG. 28 is a set of chemical formulae showing other exemplary dual enzyme cleavable peptides according to certain embodiments of the present invention.
Figure 29:
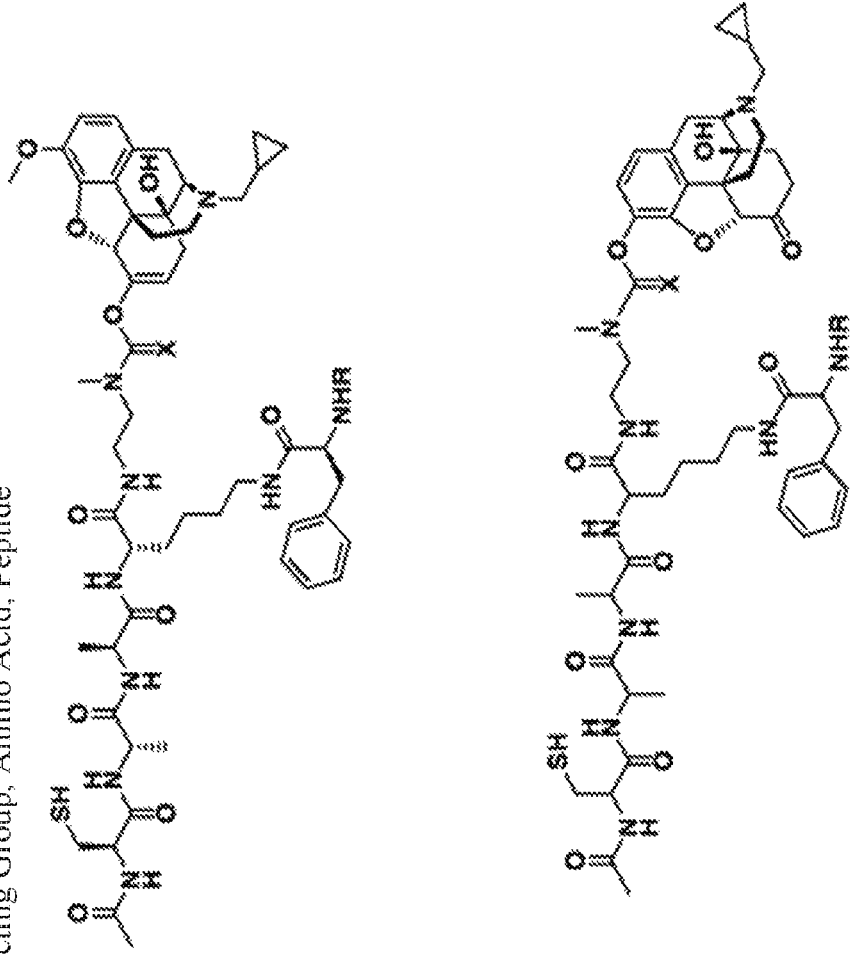
FIG. 29 is a set of chemical formulae showing other exemplary dual enzyme cleavable peptides conjugated to Naltrexone as an exemplary medication according to certain embodiments of the present invention.

FIG. 28 shows chemical formulae of exemplary dual enzyme cleavable peptides for controlled releasing Naltrexone. FIG. 29 shows chemical formulae of exemplary dual enzyme cleavable peptides covalently bonded with Naltrexone for controlled releasing Naltrexone.

In one aspect, the present invention is a method for controlled releasing an active ingredient by using the enzyme-responsive peptides as discussed above.

The method of the present invention include the step of making an enzyme-responsive peptide as discussed above. The Example shows a detail step for making an enzyme-responsive peptide. For example, a dual enzyme-responsive peptide of the present invention may be produced by specifically designing the enzyme substrates in the structure of the enzyme-responsive peptide.

The present invention may be applicable to produce an enzyme-responsive peptide which requires digestion of more than two enzymes. For example, a triple or a quadruple enzyme-responsive peptide may be produced by using the method of the present invention.

After the production of the enzyme-responsive peptide, the enzyme-responsive peptide may be delivered to a specific condition where the active ingredient may be released.

In one embodiment, the method comprising the steps of:
(1) making a compound having a general structure of

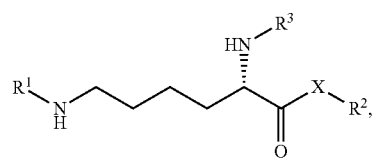

X=O, NH or S; $R^1$=an enzyme substrate; $R^2$=a reporter molecule, an amino acid, a peptide, a polymer, or an active ingredient; and $R^3$=a protecting group, a H, an amino acid or a peptide;
(2) contacting the compound with a first enzyme, wherein $R^1$ is cleaved from the compound upon digestion by the first enzyme to form a second compound with a free ε-amine group; and
(3) contacting the second compound with a second enzyme, wherein the active ingredient $R^2$—X is released from the second compound upon digestion of the second enzyme.

In one embodiment, $R^1$ is a protease substrate.

In one embodiment, the protease substrate is selected from the group consisting of Ac-AAF, Ac-F, Ac-FG, Ac-DEVD (SEQ ID NO: 7).

In one embodiment, $R^1$ is a protease substrate corresponding to a protease selected from the group consisting of chymotrypsin, papain, caspase 8, and caspase 3.

In one embodiment, $R^1$ is a protease substrate selected from the group consisting of a chymotrypsin substrate, a papain substrate, a caspase 8 substrate and a caspase 3 substrate.

In one embodiment, $R^2$ is a releasing group that can be controlled releasing in the peptide. Applicants envision that many functional groups or compounds may be used as a releasing group in the present invention.

In one embodiment, $R^2$ is a reporter molecule, an amino acid, a peptide, a polymer, or an active ingredient (e.g., a drug).

In one embodiment, $R^2$ is an amino acid, a peptide, a polymer, or an active ingredient.

In one embodiment, $R^2$ is an active ingredient.

In one embodiment, $R^2$ is a reporter molecule, such as an aromatic group.

In one embodiment, $R^2$ is a phenyl group.

In one specific embodiment, $R^2$ is a p-nitrophenol.

In one embodiment, $R^3$ is any protecting group that can protect a free amine group.

In one embodiment, $R^3$ is an acyl group.

In one embodiment, R³ is an acetyl group.

In one embodiment, the enzyme-responsive peptide is cleavable under the digestion of two enzymes, such as two proteases.

In one embodiment, the enzyme-responsive peptide is cleavable under the digestion of at least two enzymes including a first enzyme selected from the group consisting of chymotrypsin, papain, caspase 8 and caspase 3 and a second enzyme of trypsin.

In one embodiment, the enzyme-responsive peptide is cleavable under the digestion of two enzymes including a first enzyme selected from the group consisting of chymotrypsin, papain, caspase 8 and caspase 3 and a second enzyme of trypsin.

In one specific embodiment, the enzyme-responsive peptide is cleavable under the digestion of two enzymes selected from the enzyme pair group consisting of trypsin/chymotrypsin, trypsin/papain, trypsin/caspase 8 and trypsin/caspase 3. Exhibits A-C show some exemplary enzyme-responsive peptides which are digestible by trypsin/chymotrypsin, trypsin/papain, trypsin/caspase 8 and trypsin/caspase 3.

In one embodiment, the method of the present invention comprises the steps of (1) making a compound having a general structure of

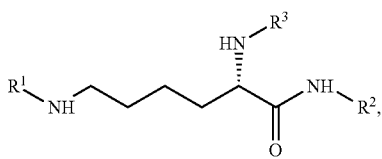

wherein R¹=an enzyme substrate or a H; R²=a reporter molecule, an amino acid, a peptide, a polymer, or an active ingredient; and R³=a protecting group, a H, an amino acid or a peptide; 2) contacting the compound with a first enzyme, wherein R¹ is cleaved from the compound under the digestion of the first enzyme to form a second compound with a free ε-amine group; and (3) contacting the second compound with a second, enzyme, wherein the active ingredient R²—NH is released from the second compound under the digestion of the second enzyme.

In one embodiment, IV is a protease substrate.

In one embodiment, the protease substrate is selected from the group consisting of Ac-AAF, Ac-F, Ac-FG, Ac-DEVD (SEQ ID NO: 7).

In one embodiment, R¹ is a protease substrate corresponding to a protease selected from the group consisting of chymotrypsin, papain, caspase 8 and caspase 3.

In one embodiment, R¹ is a protease substrate selected from the group consisting of a chymotrypsin substrate, a papain substrate, a caspase 8 substrate and a caspase 3 substrate.

In one embodiment, R² is a releasing group that can be controlled releasing in the peptide. Applicants envision that many functional groups or compounds may be used as a releasing group in the present invention.

In one embodiment, R² is a reporter molecule, an amino acid, a peptide, a polymer, or an active ingredient.

In one embodiment, R² is an amino acid, a peptide, a polymer, or an active ingredient.

In one embodiment, R² is an active ingredient.

In one embodiment, R² is a reporter molecule, such as an aromatic group.

In one embodiment, R² is a phenyl group.

In one specific embodiment, R² is a p-nitrophenol.

In one embodiment, R³ is any protecting group that can protects an amino group.

In one embodiment, R³ is an acyl group.

In one embodiment, R³ is an acetyl group.

In one embodiment, R³ is a chemical or biological agent which can act as an active ingredient, such as a drug.

In one embodiment, the first enzyme is a protease.

In one embodiment, the first enzyme is selected from the group consisting of chymotrypsin, papain, caspase 8 and caspase 3.

In one embodiment, the second enzyme is a protease.

In one embodiment, the second enzyme is trypsin.

In one embodiment, the active ingredient is not cleavable before the cleavage of R¹ from the compound.

Examples 1-5 demonstrate the synthesis of dual enzyme-responsive peptides and methods of using these dual enzyme-responsive peptides for controlled releasing an active substances such as a medicine or a drug. For example, Example 5 shows the synthesis of dual enzyme-responsive peptides covalently bonded with Naltrexone as one example of a medicine and methods of controlled releasing Naltrexone as a model system of opioids.

EXAMPLES

Example 1

Representative Peptide Synthesis:

Protease substrates (Ac-AAF, Ac-F, Ac-FG, Ac-DEVD (SEQ ID NO: 7)) were synthesized using standard fmoc solid-phase chemistry with 2-chlorotrityl chloride resin (0.4 or 1.2 mmol/g substitution). 0.1M HOBt in 20% 4-methylpiperidine in DMF was used for Fmoc deprotection to reduce aspartimide formation. N-termini were acetylated prior to cleavage from resin using 50 eq. acetic anhydride and DMA in DMF for 30 min. Peptides were cleaved from the resin using 0.5% TFA in DCM. Reverse coupling to acetylated lysine p-nitroanilide was carried out in DMF using 3 eq. HBTU and 6 eq. DIEA. Nitroanilide peptides were purified either by dissolving in ethyl acetate and washing with saturated NaHCO₃, NH₄Cl, and brine, or by preparative reverse-phase HPLC equipped with a C18 column using a linear gradient from 95:5 to 5:95 H2O/acetonitrile with 0.1% TFA at a flow rate of 20 ml/min. ESI-MS was used to confirm the molecular masses of the desired products.

Representative Dual Enzyme Assay:

Stock solutions of enzymes were prepared by dissolving trypsin (60 mg/ml) in 1 mM HCl and chymotrypsin (60 mg/ml) in pH 7.4 0.035M HEPES+0.1M NaCl. The peptide substrate, (Ac-AAF)K-pNA, was dissolved in DMSO to make a 1 mM stock solution.

To wells in a 96-well plate, 87.5 μL pH 7.4 0.035M HEPES+0.1M NaCl and 2.5 μL peptide substrate were added. Absorbance was measured using a plate reader at 405 nm. Then, 5 μL trypsin and 5 μL chymotrypsin were added to the wells, and absorbance was measured at pre-determined time points. Absorbance values were subtracted from initial reading of only buffer and peptide. When testing only one enzyme, 5 μL buffer were added to keep total volume per well at 100 μL. All conditions prepared and measured in triplicate.

Commercial Applications & Competitive Advantages:

These peptides can be used in polymeric formulations, either as cross-linkers or incorporated into the backbone, installing dual-enzyme sensitivity. Formulations will only be able to degrade when the peptide is successfully digested by two enzymes. If only one enzyme, or an enzyme that does not cleave the given peptide sequence, is used, no peptide cleavage can occur. We envision this to be useful for delayed release formulations/prodrugs, preventing users from releasing the drug compound through other routes than digestion. Currently, most enzyme responsive technologies are sensitive to a single enzyme or a single enzyme+an environmental stimulus. A similar dual enzyme system has used acetylated lysine to monitor histone deacetylase (HDAC) activity indirectly (see section 6 for more information), yet the combination of HDACs+trypsin are not relevant for prodrug formulations. Our system differs because it requires sequential digestion by two physiologically relevant enzymes, and the modular nature allows the system to be used for a variety of applications.

Example 2

Dual enzyme-responsive peptides were synthesized by masking the ε-amine of lysine with various enzyme substrates. Enzymatic cleavage of these sequences unmasked the F-amine, allowing for further digestion by a second enzyme, which was monitored colorimetrically. This modular peptide design should provide substrates for a large combination of clinically relevant enzymes.

We designed our system to be dual enzyme-responsive by modifying the F-amine of lysine with substrates for four different proteases: chymotrypsin, papain, and caspases 3 and 8 (FIG. 1). We chose these substrates to demonstrate that lysine modification can be used to analyze the activity of a broad range of enzymes.

Enzyme substrates chosen for chymotrypsin, papain, and caspases 3 and 8 were AcAAF, AcFG, AcDEVD (SEQ ID NO: 7), and AcIEPD (SEQ ID NO: 8), respectively. Peptides were synthesized using standard Fmoc solid phase chemistry. 12 Initially, the side chain of N2-acetyl-L-lysine was modified with various protease substrates on resin before coupling the peptide to p-nitroaniline (pNA) in solution phase after cleavage from the resin (Scheme 2). 13 This approach proved to be challenging to purify on a larger scale due to the large excess of reagents required to drive the reaction to completion.

Therefore, a more modular solution phase approach was subsequently used in which protease substrates were coupled to a lysine nitroanilide using solution phase conditions (Schemes 3 and 4). Peptide identity and purity were confirmed by LC-MS. Trypsin and chymotrypsin were chosen as initial model enzymes because they each require only a single amino acid for recognition and cleavage. The peptide sequence chosen for chymotrypsin/trypsin detection, (Ac-AAF)K-pNA, was designed with phenylalanine at the ε-amine of lysine nitroanilide to install chymotrypsin sensitivity since chymotrypsin recognizes and cleaves at the C-terminal side of bulky, aromatic amino acids.[14]

Figure 2:
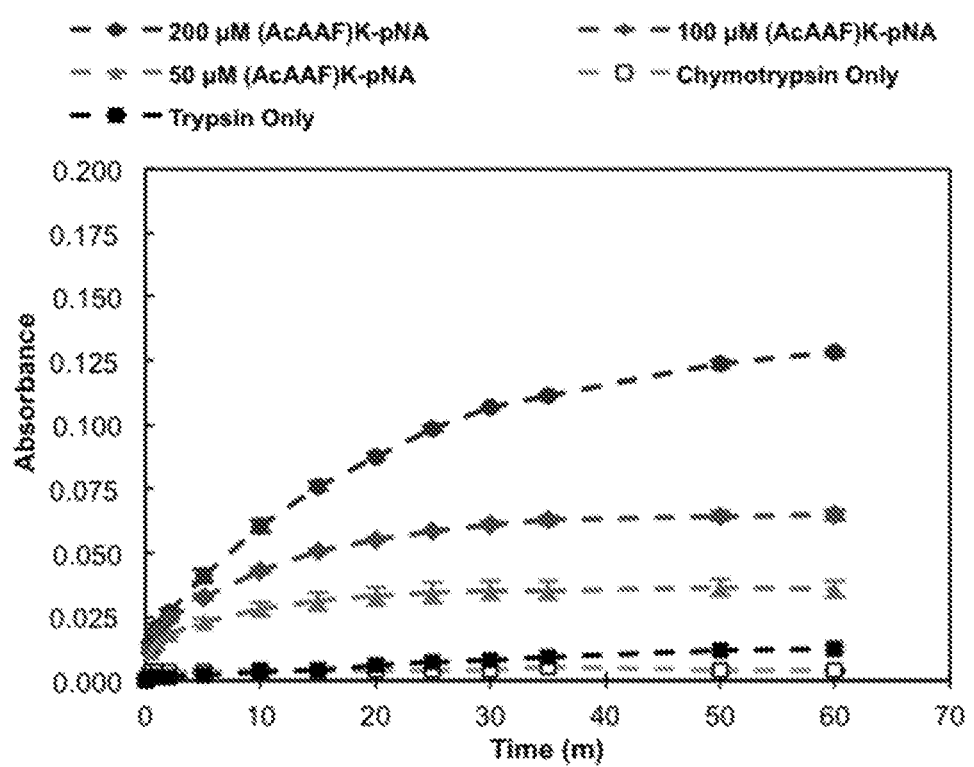
FIG. 2 is a graph showing (AcAAF)K-pNA digestion with trypsin and chymotrypsin resulted in an absorbance increase, corresponding to pNA release. Digestion with trypsin or chymotrypsin only did not result in a significant absorbance increase. Absorbance measurements were taken for first 60 minutes and at the five hour mark to confirm absorbance values had reached their maxima. Average and standard deviation of three repeats are shown.

To test the enzyme responsiveness of (AcAAF)K-pNA, the peptide was first incubated with both chymotrypsin and trypsin, and the absorbance at 405 nm, corresponding to pNA release, was monitored over time. A significant absorbance increase was observed, suggesting that both enzymes are required for complete substrate cleavage. Incubation of 501.1M (AAF)K-pNA with the enzymes showed an absorbance increase that leveled out at 0.039±0.003 AU After five hours. A two-fold absorbance increase to 0.070±0.002 AU was observed for 100 μM substrate, and a four-fold absorbance increase to 0.147±0.002 AU was observed for 200 μM substrate, indicating that release of pNA is substrate concentration dependent as expected (FIG. 2). When 100 μM peptide was incubated with only chymotrypsin, no change in absorbance was observed. However, a minimal absorbance increase (0.016±0.002 AU) was observed when 100 μM peptide was incubated with trypsin only. This minimal absorbance increase can be explained; it is known that commercial trypsin contains residual chymotrypsin activity, and thus the second enzyme is present at a low concentration.[15] Additionally, our other dual enzyme substrates (vide infra) did not show any absorbance increase when incubated with trypsin alone since they do not contain any chymotrypsin sensitive residues adjacent to lysine, further suggesting residual chymotrypsin activity is the source of the observed slight absorbance increase.

Figure 3:
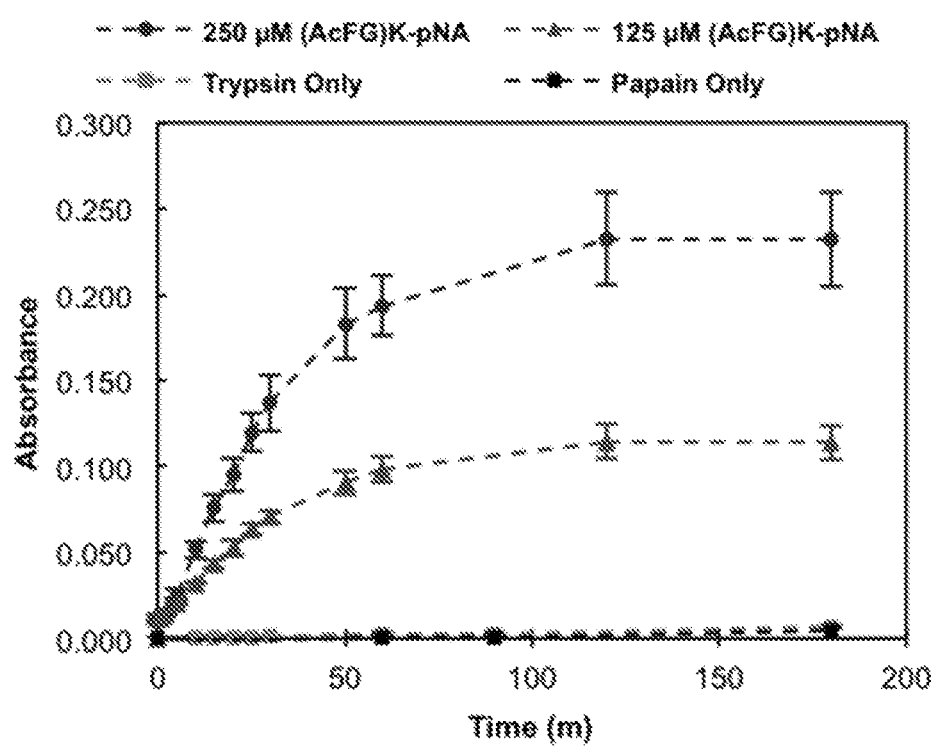
FIG. 3 is a graph showing (AcFG)K-pNA digestion with papain and trypsin at varying substrate concentrations resulted in proportional absorbance increases. Incubating the substrate with papain or trypsin only resulted in no absorbance increase. Average and standard deviation of three repeats are shown.

The second substrate, (AcFG)K-pNA, was incubated with papain and trypsin. Papain, a cysteine protease, cleaves the C terminal side one amino acid after an aromatic residue.[16] In the presence of papain and trypsin, pNA release from the substrate was observed to be substrate dependent, similar to what we had observed for (AcAAF)K-pNA digestion (FIG. 3). Again, no absorbance increase was observed when the substrate was incubated with each enzyme separately. It is interesting to note that papain digestion of basic amino acids, such as lysine, has been reported; however, cleavage rates are drastically lower than those observed for Phe-Gly, which is evidenced by the lack of absorbance increase when papain only was added to the substrate (FIG. 3).[17] To demonstrate the versatility of the design, two other dual-enzyme responsive peptides, (AcDEVD)K-pNA (SEQ ID NO: 1) and (AcIEPD)K-pNA (SEQ ID NO: 3), were synthesized by modifying lysine with substrates of two clinically relevant enzymes: caspases 3 and 8, respectively.[18] Caspases 3 and 8 are key proteases in apoptotic pathways that are down regulated in certain cancer cells,[19] and caspase 3 is found at elevated levels after myocardial infarctions.[20] Caspase activity assays are commonly used to monitor delivery of anti-cancer agents since activation of the apoptotic pathway can indicate successful cancer treatment.[21]

Figure 9:
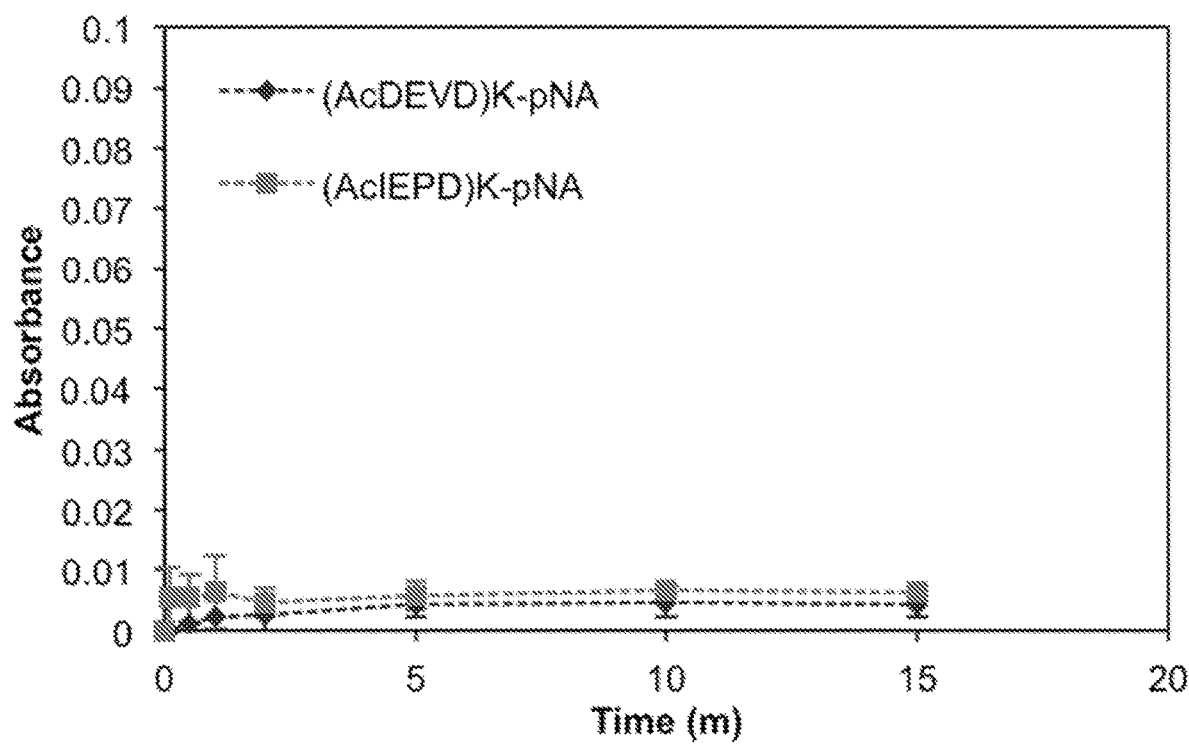
FIG. 9 is a graph showing that 500 µM (AcDEVD)K-pNA (SEQ ID NO: 1) and (AcIEPD)K-pNA (SEQ ID NO: 3) was incubated with caspase 8 for 24 hours before adding trypsin, which did not result in a significant absorbance increase. Average and standard deviation of three repeats are shown.
Figure 10:
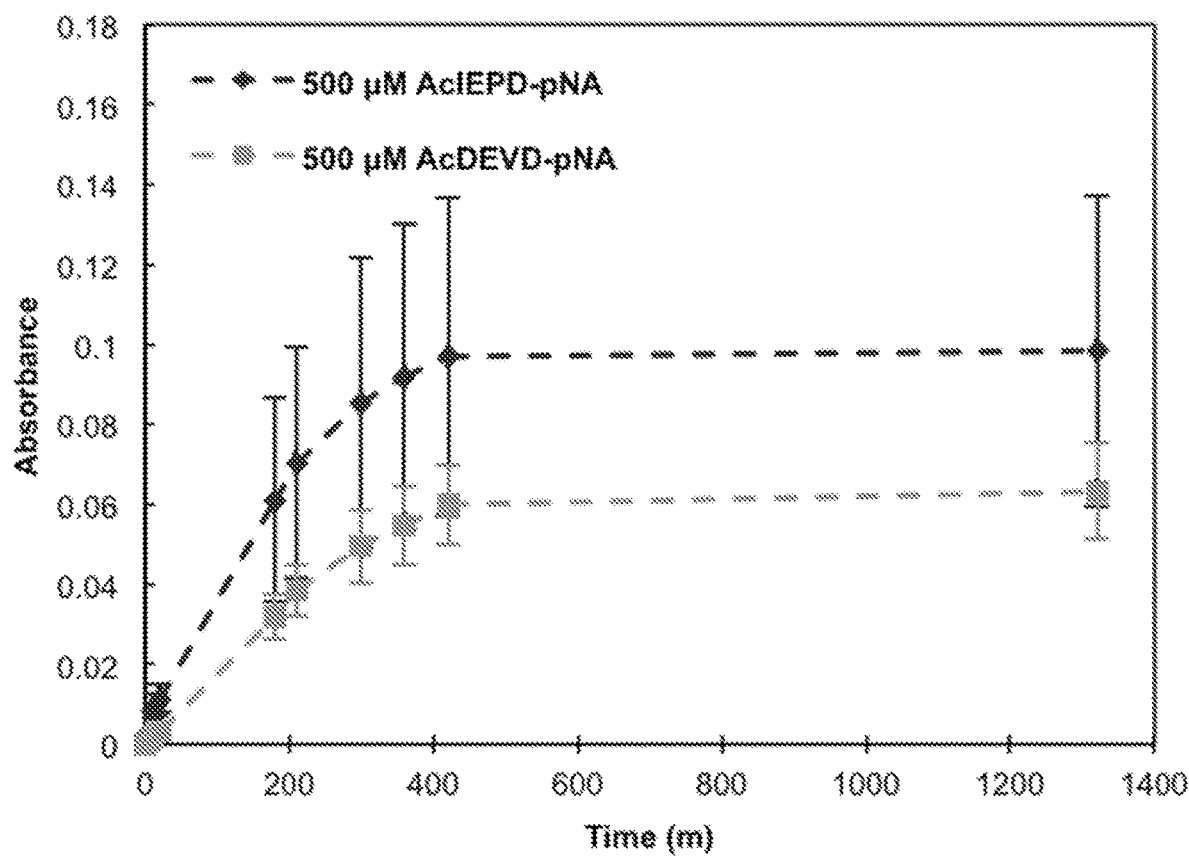
FIG. 10 is a graph showing that incubating caspase 8 with commercially available AcDEVD-pNA (SEQ ID NO: 7) and AcIEPD-pNA (SEQ ID NO: 8) resulted in a significant absorbance increase over time. Average and standard deviation of three repeats are shown.

Initial experiments with (AcIEPD)K-pNA (SEQ ID NO: 3) revealed little to no absorbance increase in the presence of caspase 8 and trypsin (FIG. 9). To ensure the enzyme itself was still active, the activity was confirmed using commercially available single enzyme substrates AcIEPD-pNA (SEQ ID NO: 8) and AcDEVD-pNA (SEQ ID NO: 7) (FIG. 10) which cleaved as expected. These results led us to hypothesize that caspase 8 is not able to efficiently digest our substrate because peptide amide bonds are much less labile than the acyl-nitroanilide in commercial substrates. Further, caspases are sensitive to the structure of the amino acid in the P1' position which is adjacent to the substrate cleavage site, and the presence of an ε-amide as P1' may negatively affect enzyme digestion.[22] Notably, $K_{cat}/K_m$ values for caspase 8 are reduced approximately 50 times on average when compared to caspase 3, prompting us to design a dual enzyme substrate sensitive to caspase 3 and trypsin.[22]

Figure 4:
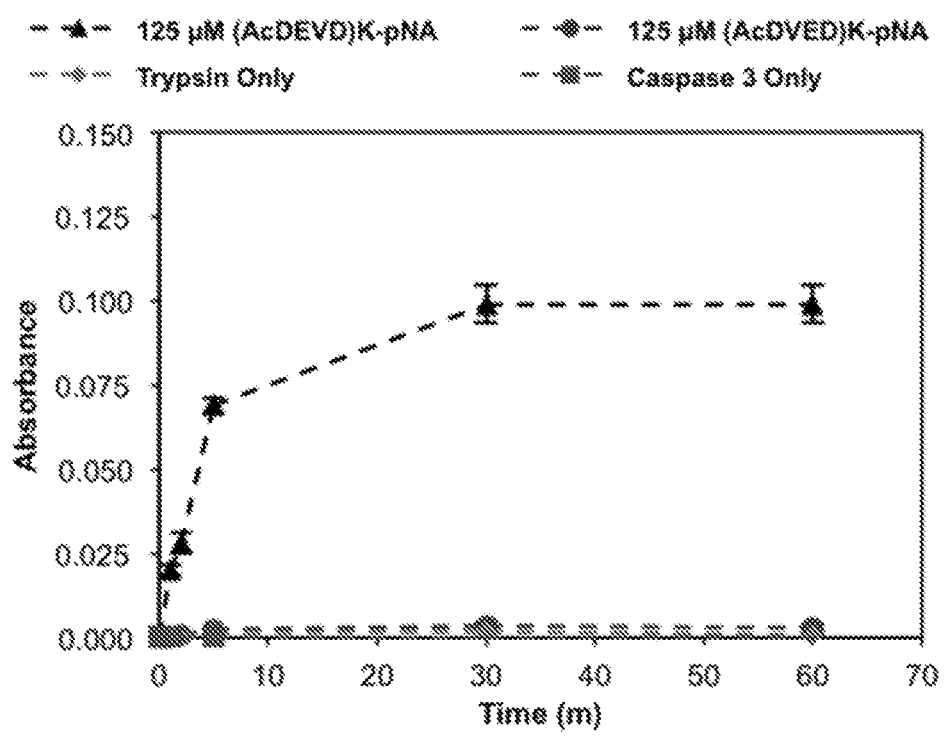
FIG. 4 is a graph showing digestion of 125 µM (AcDEVD)K-pNA (SEQ ID NO: 1) with trypsin and caspase 3 results in p-nitroaniline release. No release is observed when only trypsin or caspase 3 is used or when the caspase 3 recognition sequence was scrambled ((AcDVED)K-pNA (SEQ ID NO: 2)). Average and standard deviation of four repeats are shown.
Figure 5:
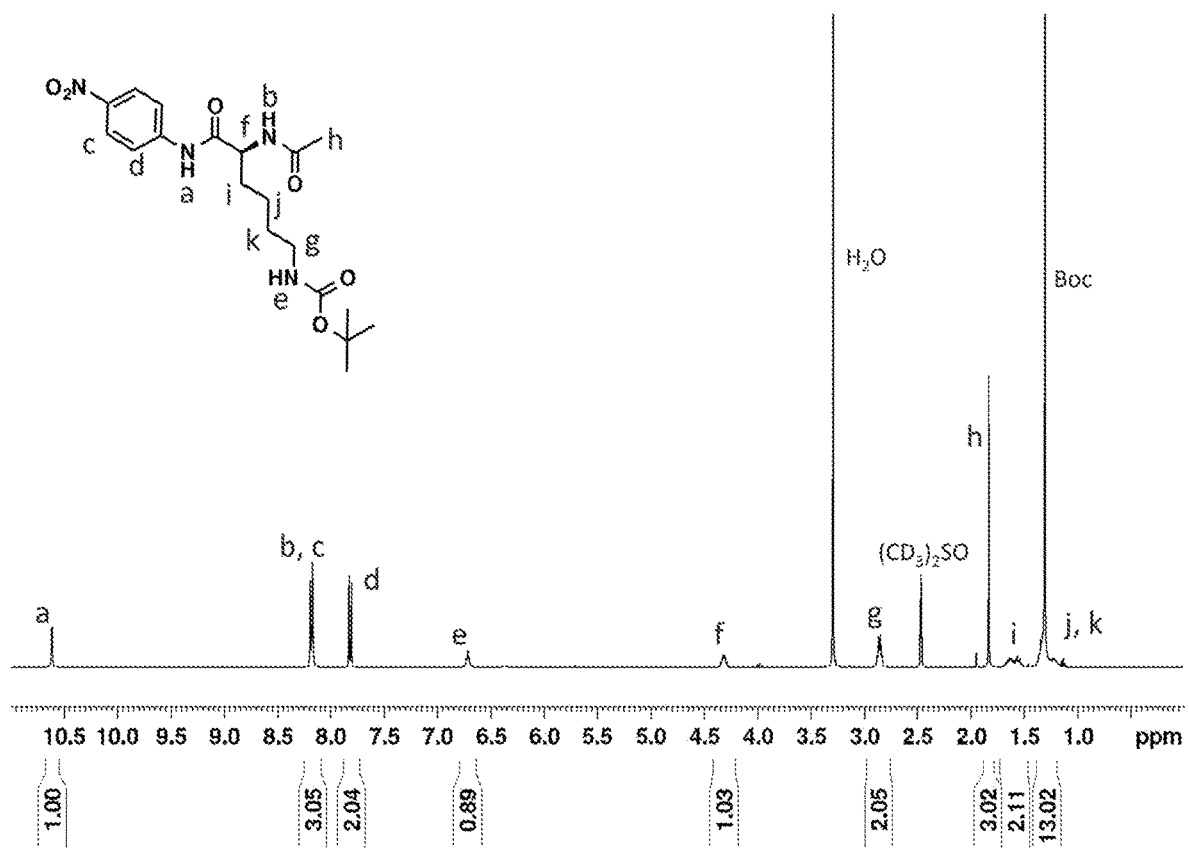
FIG. 5 is a graph showing $^1$H NMR spectrum of t-butyl (S)-(5-acetamido-64(4-nitrophenyl)amino)-6-oxohexyl)carbamate (2) in $(CD_3)_2SO$.
Figure 6:
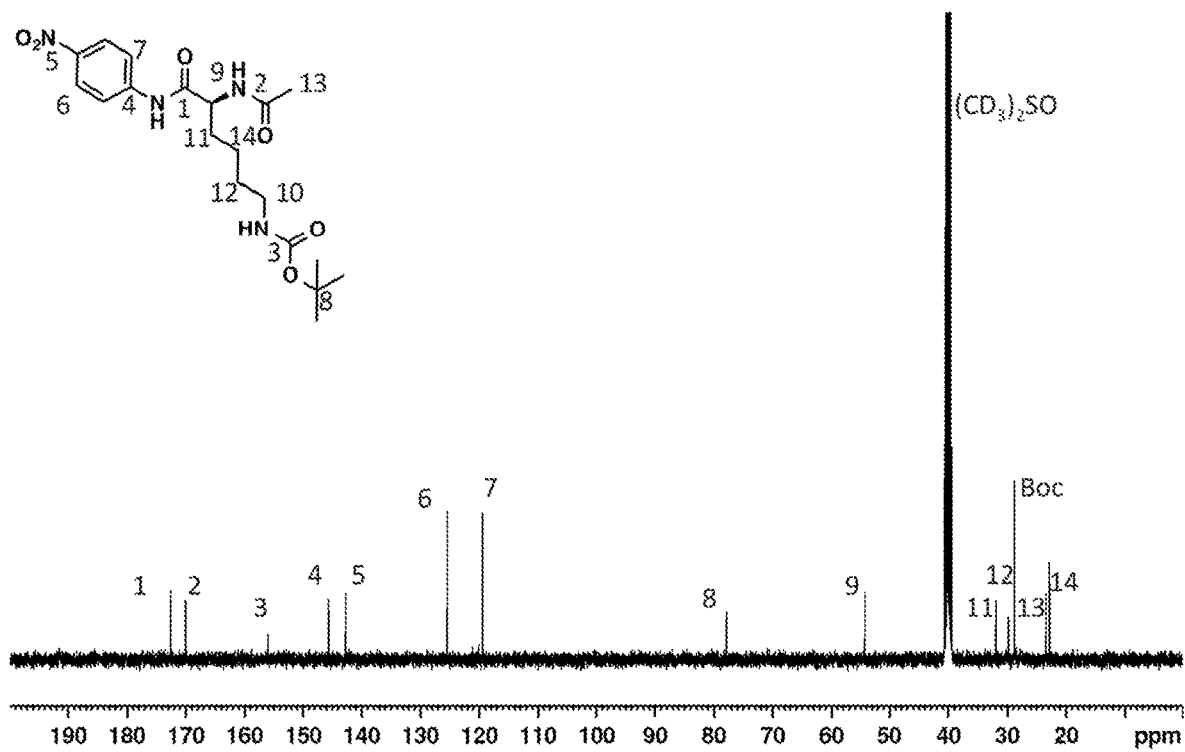
FIG. 6 is a graph showing $^{13}$C NMR spectrum of t-butyl (S)-(5-acetamido-6-((4-nitrophenyl)amino)-6-oxohexyl) carbamate (2) in $(CD_3)_2SO$.
Figure 7:
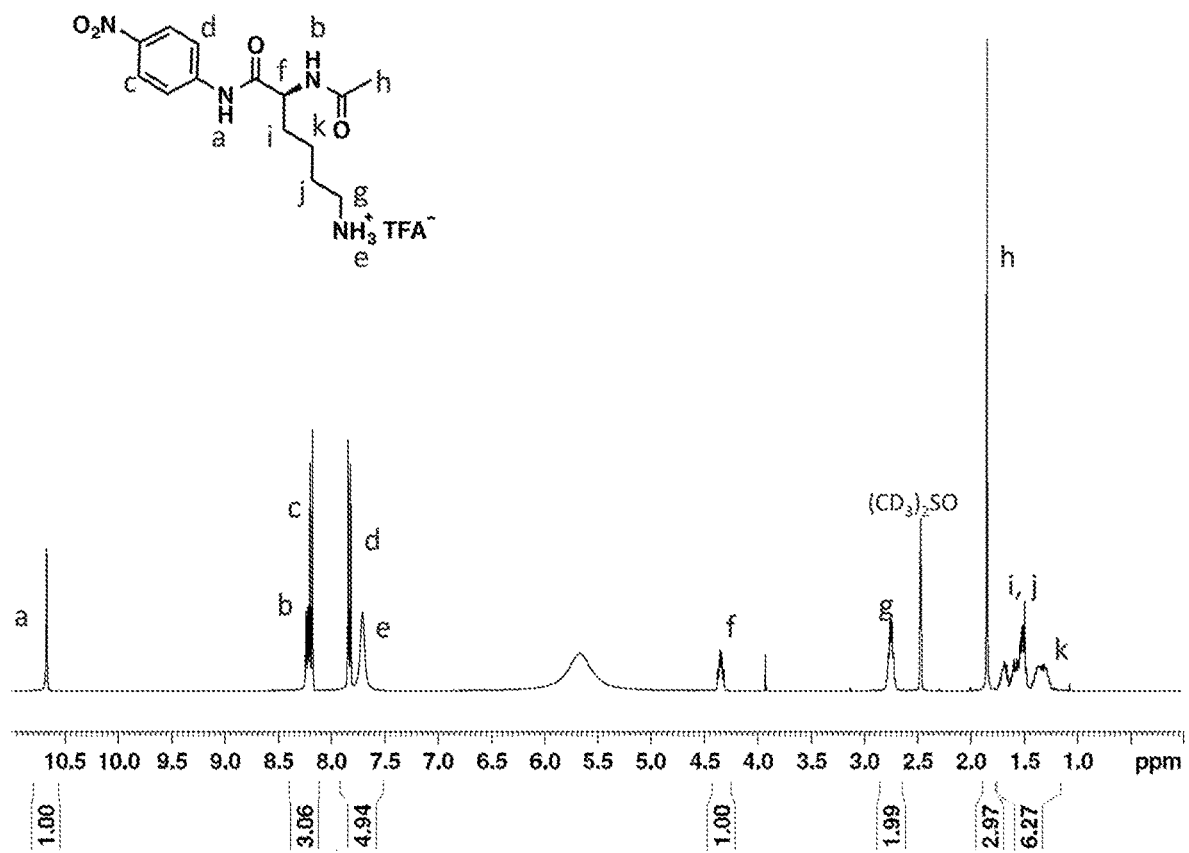
FIG. 7 is a graph showing $^1$H NMR spectrum of (S)-2-acetamido-6-amino-N-(4-nitrophenyl)hexanamide (3) as the TFA salt in $(CD_3)_2SO$.
Figure 8:
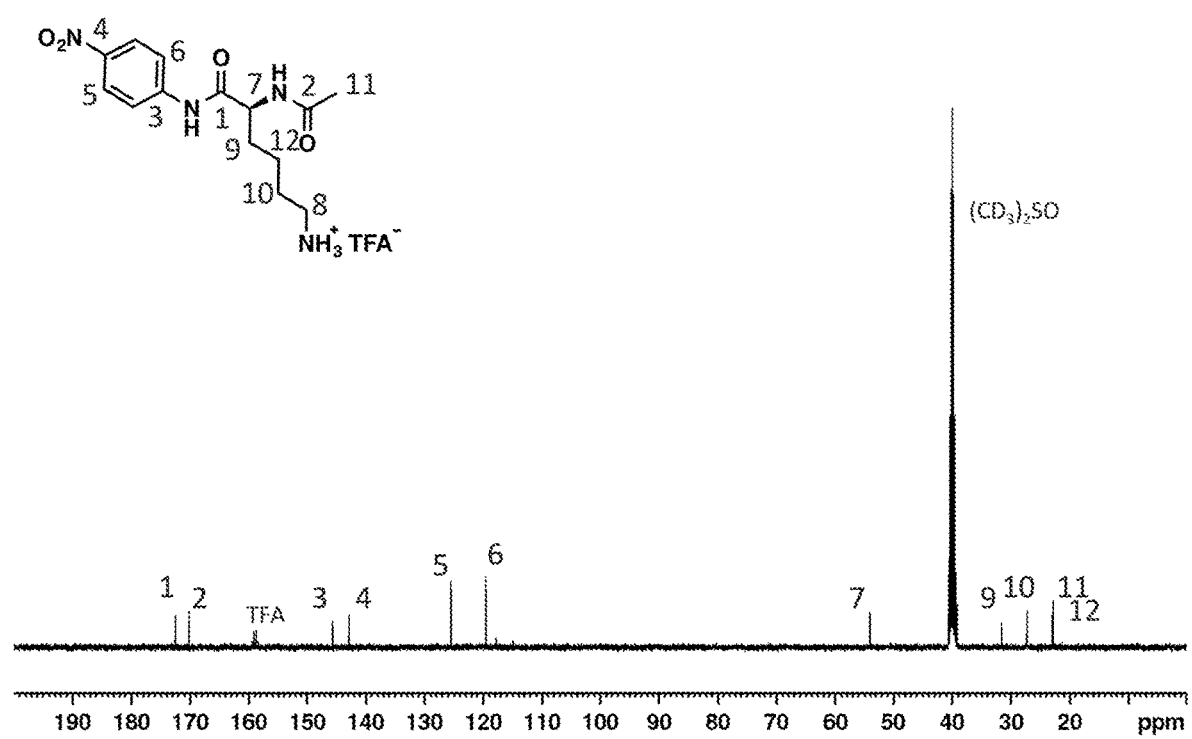
FIG. 8 is a graph showing $^{13}$C NMR spectrum of (S)-2-acetamido-6-amino-N-(4-nitrophenyl)hexanamide (3) as the TFA salt in $(CD_3)_2SO$.

Enzyme sensitivity of (AcDEVD)K-pNA (SEQ ID NO: 1) was assessed after incubating 125 μM of substrate first with caspase-3 then with trypsin, which resulted in an absorbance increase of 0.1±0.006 AU over 60 minutes (FIG. 4). This indicated that caspase 3 was able to digest the substrate in contrast to our findings for caspase 8. In the presence of trypsin or caspase 3 only, no absorbance increase was observed as expected. A scrambled version of the caspase 3 substrate, (AcDVED)K-pNA (SEQ ID NO: 2) was also synthesized, for which no enzyme digestion was anticipated. As hypothesized, no pNA release occurred when (AcDVED)

Figure 11:
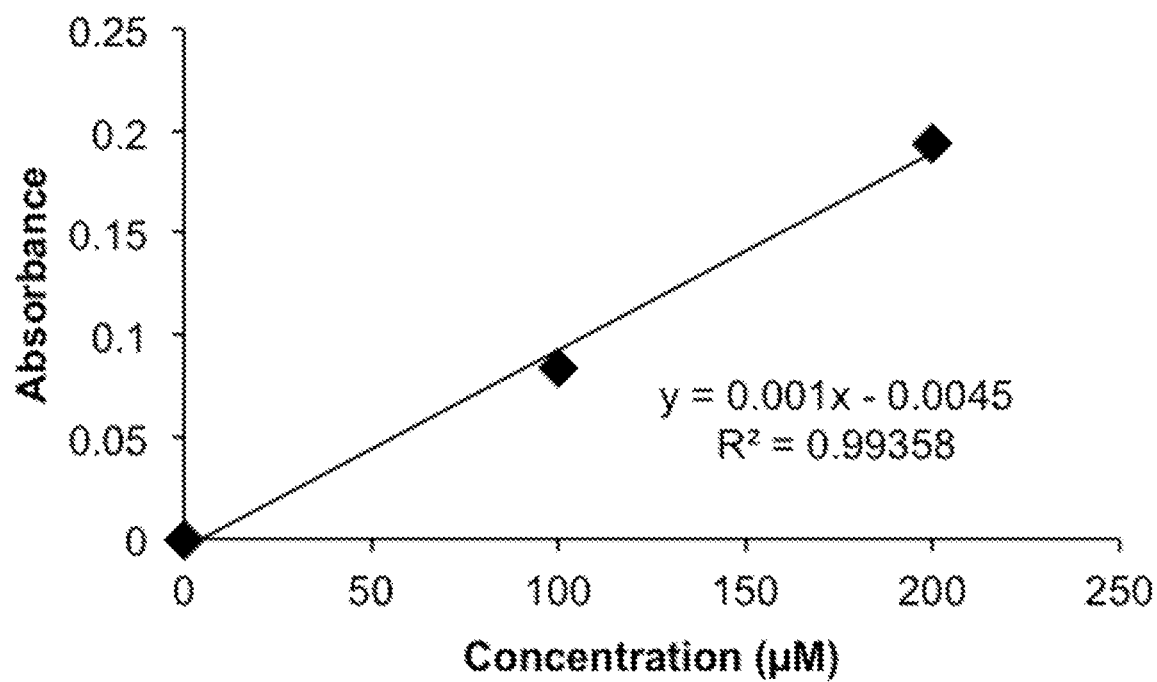
FIG. 11 is a graph showing that caspase-3 digestion of commercial Ac-DEVD-pNA (SEQ ID NO: 7). Each measurement was carried out in triplicate, and a linear trend line was generated from average absorbance values plotted against concentration. Average of three repeats was used to generate standard curve.

K-pNA (SEQ ID NO: 2) was incubated with trypsin and caspase 3 (FIG. 4). Because of the difference in caspase 8 cleavage rates of (AcIEPD)K-pNA (SEQ ID NO: 3) and AcIEPD-pNA (SEQ ID NO: 8), we wanted to compare caspase 3 digestion of (AcDEVD)K-pNA (SEQ ID NO: 1) to its commercial substrate, AcDEVD-pNA (SEQ ID NO: 7). We found that pNA release from our substrate corresponded to 83% of the release from the commercial substrate, indicating both substrates are digested efficiently by caspase 3 and that our peptide system may be useful for enzyme activity screening assays (FIG. 11).

Due to the modular design of our dual-enzyme responsive peptides, a wide range of protease substrates could be coupled to the lysine side chain. This could be useful for multi-enzyme screening applications as well as for creating selectively degradable materials for drug delivery. While we have not yet explored using other proteases in place of trypsin, doing so would broaden the scope of our system even further. Our data also show that the cleavage rates of each enzyme must be taken into account when designing further dual enzyme responsive peptides in this manner, providing information for successful design.

In summary, we have designed and synthesized a series of multi-enzyme responsive peptides by modifying the ε-amine of lysine with substrates of three different proteases: chymotrypsin, papain, and caspase 3. It was shown that dual protease activity is required for nitroaniline release to occur. Due to the modular design, we envision that these peptides could be used for selective drug delivery, for fundamental studies on dual enzyme activity, as well as for diagnostic enzyme screening.

Materials and Methods

Fmoc-protected amino acids were purchased from Chem Impex. Chymotrypsin (64.8 units/mg) was purchased from Sigma Aldrich. Trypsin (225 units/mg), papain (30.3 units/mg), and caspases 3 (100 units/μL) and 8 (0.2 mg/ml) were purchased from Fisher Scientific. All other chemicals were purchased from Sigma Aldrich. $^1$H NMR and $^{13}$C NMR spectra were obtained on an Avance DRX 400 MHz instrument. ESI mass spectra were obtained using a Waters Acquity LCT Premier XE. Assay measurements were carried out on a Bio-Tek ELx 800 Microplate Reader.

Synthesis and Characterization of Peptides

Peptide Synthesis: Method 1

Figure 31:
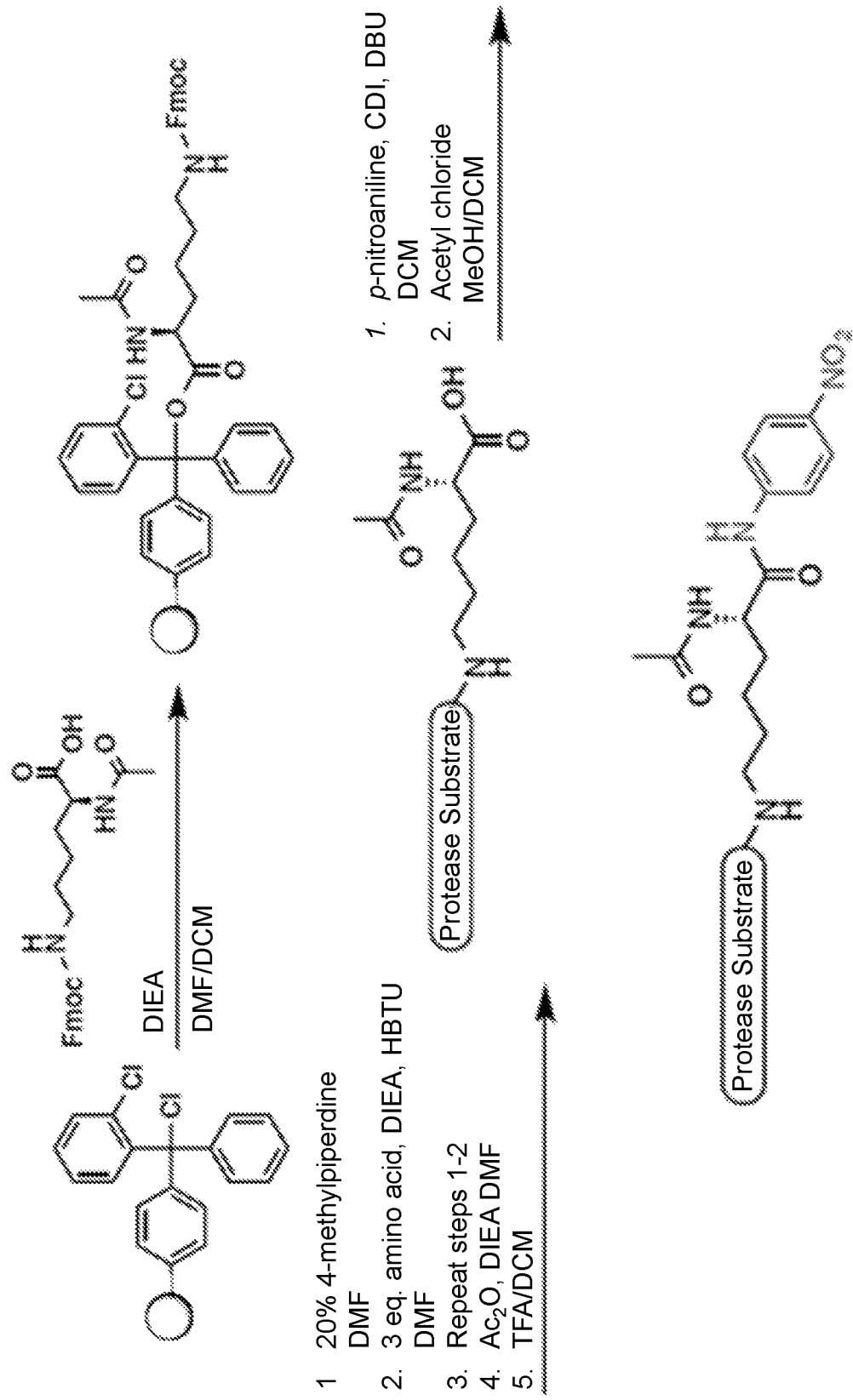
FIG. 31 is a scheme showing synthesis of nitroanilide peptides using method 1.

Peptides were synthesized using standard fmoc solid-phase chemistry with a 2-chlorotrityl chloride resin (0.4 mmol/g substitution). N-termini were acetylated prior to cleavage from the resin using eq. acetic anhydride and diisopropylethylamine (DIEA) in dimethylformamide (DMF) for 30 min. Peptides were cleaved from the resin using 95:2.5:2.5 trifluoracetic acid (TFA)/triisopropylsilane (TIPS)/H$_2$O. For peptides containing t-butyl protecting groups, 0.5% TFA in dichloromethane (DCM) was used to cleave from the resin, thereby keeping any protecting groups intact. Peptides were modified with p-nitroaniline using a previously reported procedure. 23 Peptides were purified by preparative reverse-phase HPLC equipped with a C18 column using a linear gradient from 95:5 to 5:95 H$_2$O/acetonitrile with 0.1% TFA at a flow rate of 20 ml/min. ESI-MS was used to confirm the molecular masses of the desired products. An exemplary schematic of the synthesis of nitroanilide peptides using method 1 is illustrated in FIG. 31.

Synthesis of (S)-2-acetamido-6-amino-N-(4-nitrophenyl) hexanamide Lys(Boc)-pNA 1 (2.0 g, 5.46 mmol) was dissolved in dichloromethane (10 ml). Triethylamine (3.4 ml, 24.6 mmol) was added before cooling the solution to 0° C. using an ice bath. Acetic anhydride (2.3 ml, 24.6 mmol) was added drop wise and the reaction stirred for 3 hours. During the reaction, a precipitate formed, and a beige color developed. Dichloromethane was removed under vacuum, and solids were re-dissolved in ethyl acetate (~20 ml) before washing with 2×NaHCO$_3$, 2× sat. NH$_4$Cl, and 1× brine. The organic layer was dried over MgSO4 before reducing volume under vacuum. Product was re-crystallized two times from ethyl acetate to yield a beige solid 2 (1.6 g, 72%). Calc. [M+1]: 409.2009 Da; Obs. [M+1]: 409.2072 Da. 1H NMR of 2 (400 MHz, (CD$_3$)$_2$SO) 10.68-10.55 (s, 1H), 8.25-8.10 (m, 3H), 7.88-7.77 (dt, 2H, J=10.2, 2.5 Hz), 6.78-6.65 (t, 1H, J=5.5 Hz), 4.38-4.23 (m, 1H), 2.92-2.77 (q, 2H, J=6.4 Hz), 1.87-1.78 (s, 3H), 1.71-1.48 (m, 2H), 1.39-1.16 (m, 13H) ppm. 13C NMR of 2 (400 MHz, (CD$_3$)$_2$SO) δ 172.6, 170.0, 156.0, 145.6, 142.7, 125.4, 119.4, 77.7, 54.2, 31.9, 29.7, 28.7, 23.3, 22.8 ppm. Carbon 10 not observed due to solvent overlap. 2 was dissolved in 1:1 TFA/DCM (4 ml) and stirred for 1 hour before removing solvent under vacuum to give 3 as a beige solid in quantitative yield. Calc. [M+1]: 309.1485 Da; Obs. [M+1]: 309.1616 Da. 1H NMR of 3 (400 MHz, (CD3)2SO) δ 10.72-10.63 (s, 1H), 8.29-8.15 (m, 3H), 7.88-7.78 (dt, 2H, J=10.2, 2.5 Hz), 7.78-7.61 (broad s, 3H), 4.42-4.26 (m, 1H), 2.84-2.66 (m, 2H), 1.90-1.78 (s, 3H), 1.75-1.17 (m, 6H) ppm. $^{13}$C NMR of 3 (400 MHz, (CD3)2SO) δ 174.4, 170.1, 159.0, 158.7, 145.6, 142.8, 125.4, 119.4, 54.1, 31.6, 27.1, 23.0, 22.8 ppm. Carbon 8 not observed due to solvent overlap.

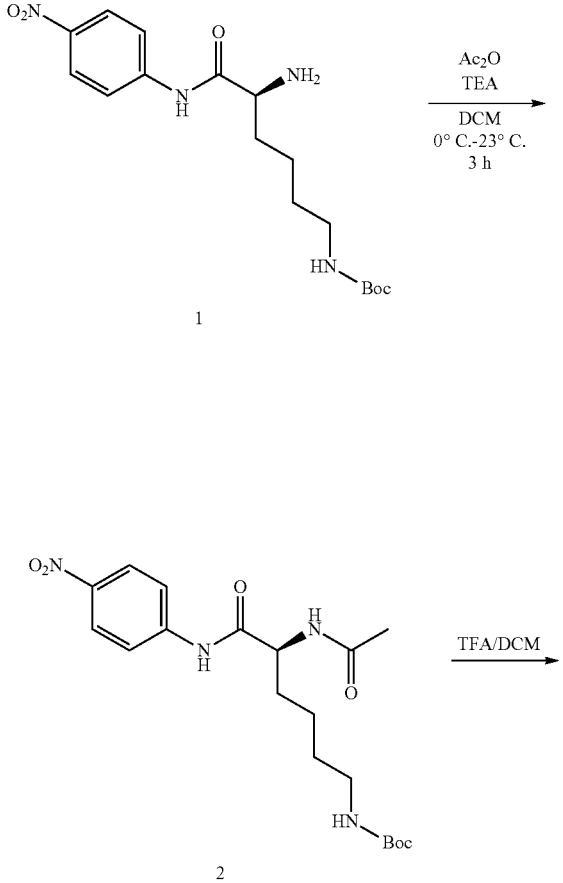

Scheme 4. Synthesis of 3.

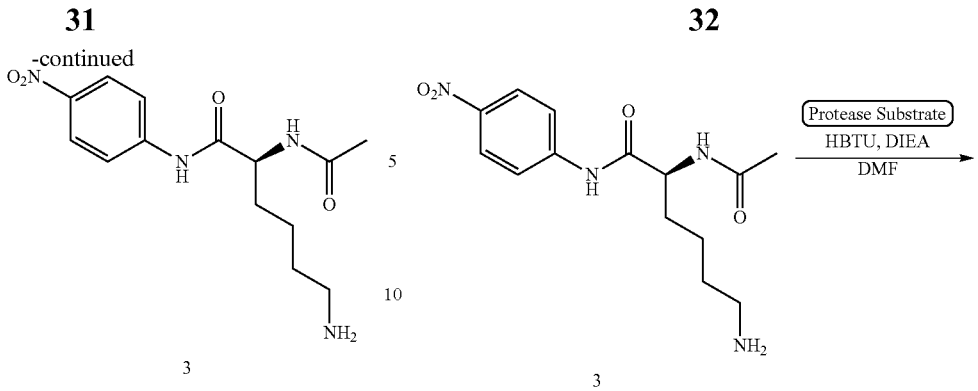

Peptide Synthesis: Method 2

Protease substrates (Ac-FG, Ac-DEVD (SEQ ID NO: 7), Ac-DVED (SEQ ID NO: 10), Ac-IEPD (SEQ ID NO: 8)) were synthesized using standard fmoc solid-phase chemistry with 2-chlorotrityl chloride resin (0.4 or 1.2 mmol/g substitution). 0.1M HOBt in 20% 4-methylpiperidine in DMF was used for Fmoc deprotection to reduce aspartimide formation. 2 N-termini were acetylated prior to cleavage from resin using 50 eq. acetic anhydride and DIEA in DMF for 30 min. Peptides were cleaved from the resin using 0.5% TFA in DCM. Reverse coupling to 3 was carried out in DMF using 3 eq. HBTU and 6 eq. DIEA. Nitroanilide peptides were purified either by dissolving in ethyl acetate and washing with saturated NaHCO$_3$, NH$_4$Cl, and brine, or by preparative reverse-phase HPLC equipped with a C18 column using a linear gradient from 95:5 to 5:95 H$_2$O/acetonitrile with 0.1% TFA at a flow rate of 20 ml/min. ESI-MS was used to confirm the molecular masses of the desired products.

(AcAAF)K-pNA:

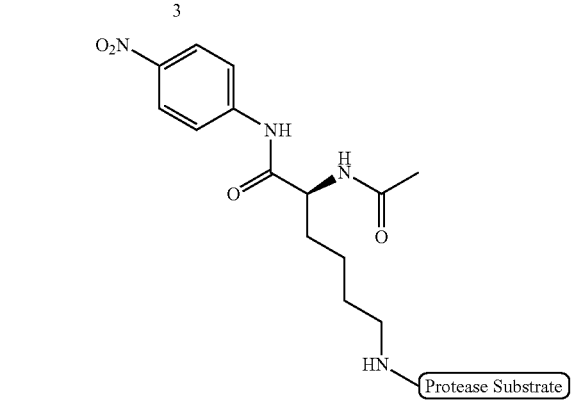

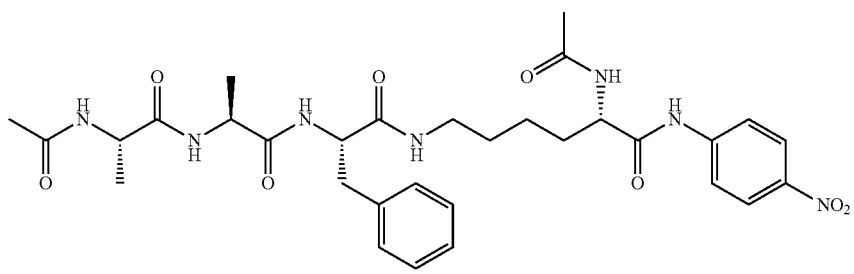 [SMILES: CC(=O)N[C@@H](C)C(=O)N[C@@H](C)C(=O)N[C@@H](Cc1ccccc1)C(=O)NCCCC[C@H](NC(C)=O)C(=O)Nc1ccc([N+](=O)[O-])cc1]

Calc. [M+TFA]: 752.2873 Da; Obs. [M+TFA]: 752.3518 Da

Analytical HPLC Conditions:
min: 10% ACN with 0.1% TFA
min: 10-100% ACN with 0.1% TFA
12.5-15 min: 100% ACN with 0.1% TFA
Peptide eluted at 8.3 min.
HPLC purity: 71.2%

(AcFG)K-pNA:

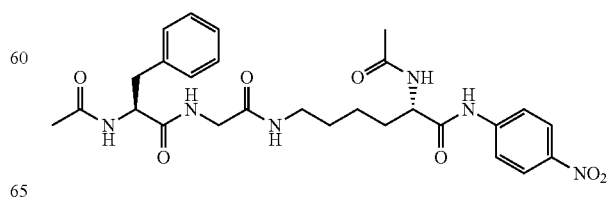

Calc. [M+Na]: 577.2381 Da; Obs. [M+Na]: 577.2471 Da

Analytical HPLC conditions:
min: 10% ACN with 0.1% TFA
min: 10-100% ACN with 0.1% TFA
12.5-15 min: 100% ACN with 0.1% TFA
Peptide eluted at 8.3 min.
HPLC Purity: 96.7%
(AcDEVD)K-pNA (SEQ ID NO: 1):

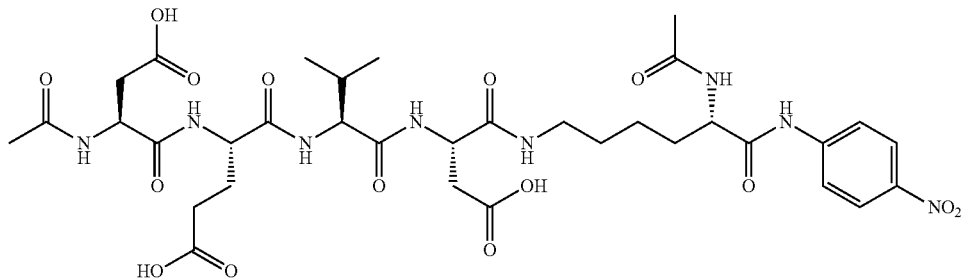 [SMILES: CC(=O)N[C@@H](CCCCNC(=O)[C@H](CC(=O)O)NC(=O)[C@@H](NC(=O)[C@H](CCC(=O)O)NC(=O)[C@H](CC(=O)O)NC(C)=O)C(C)C)C(=O)Nc1ccc([N+](=O)[O-])cc1]

Calc. [M−1]. 807.3240 Da; Obs. [M−1]: 807.3092 Da
Analytical HPLC conditions:
min: 10% ACN with 0.1% TFA
min: 10-100% ACN with 0.1% TFA
12.5-15 min: 100% ACN with 0.1% TFA
Peptide eluted at 7.0 min.
HPLC Purity: 84.7%
(AcDVED)K-pNA (SEQ ID NO: 2):

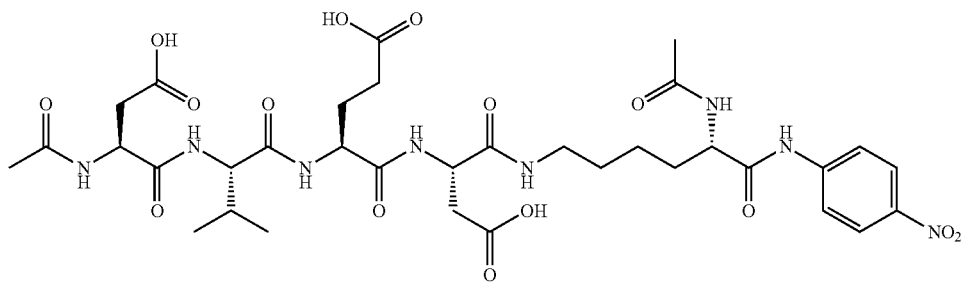 [SMILES: CC(=O)N[C@@H](CCCCNC(=O)[C@H](CC(=O)O)NC(=O)[C@H](CCC(=O)O)NC(=O)[C@@H](NC(=O)[C@H](CC(=O)O)NC(C)=O)C(C)C)C(=O)Nc1ccc([N+](=O)[O-])cc1]

Calc. [M−1]: 807.3240 Da; Obs. [M−1]: 807.3287 Da
Analytical HPLC Conditions:
min: 10% ACN with 0.1% TFA
min: 10-100% ACN with 0.1% TFA
12.5-15 min: 100% ACN with 0.1% TFA
Peptide eluted at 7.0 min.
HPLC Purity: 99.2%

(AcIEPD)K-pNA (SEQ ID NO: 3):

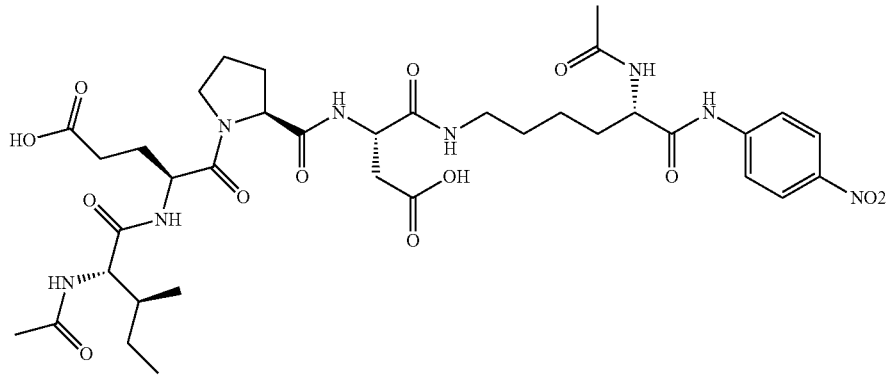 [SMILES: CC[C@H](C)[C@H](NC(C)=O)C(=O)N[C@@H](CCC(=O)O)C(=O)N1CCC[C@H]1C(=O)N[C@@H](CC(=O)O)C(=O)NCCCC[C@H](NC(C)=O)C(=O)Nc1ccc([N+](=O)[O-])cc1]

Calc. M-H: 803.3654 Da; Obs. M-H: 803.3658 Da
Analytical HPLC Conditions:
min: 10% ACN with 0.1% TFA
min: 10-100% ACN with 0.1% TFA
12.5-15 min: 100% ACN with 0.1% TFA
Peptide eluted at 7.6 min.
Purity by HPLC: 96.2%
Assays
Trypsin+Chymotrypsin Assay Stock solutions of enzymes were prepared by dissolving trypsin (60 mg/ml) in 1 mM HCl and chymotrypsin (60 mg/ml) in pH 7.4 0.035M HEPES+0.1M NaCl. The peptide substrate, (Ac-AAF)K-pNA, was dissolved in DMSO to make a 1 mM stock solution. To wells in a 96-well plate, 87.5 µL pH 7.4 0.035M HEPES+0.1M NaCl and 2.5 µL peptide substrate were added. Absorbance was measured using a plate reader at 405 nm. Then, 5 µL trypsin and 5 µL chymotrypsin were added to the wells, and absorbance was measured at pre-determined time points. Absorbance values were subtracted from initial reading of only buffer and peptide. When testing only one enzyme, 5 µL buffer were added to keep total volume per well at 100 µL. All conditions were measured in triplicate.

Papain+Trypsin Assay

Papain was reconstituted in deionized water at a concentration of 1 mg/ml. A stock solution of trypsin was prepared by dissolving the enzyme (10 mg/ml) in 1 mM HCl. The peptide substrate, (AcFG)K-pNA was dissolved in DMSO to make a 5 mM solution. Separately, 3M NaCl and 20 mM EDTA+50 mM cysteine (pH 6.2) solutions were prepared with deionized water. In a 96-well plate, 5 µL substrate were mixed with 45 µL NaCl and 40 µL EDTA+cysteine solutions. Absorbance was measured at 405 nm to serve as a blank. Then, 5 µL of both enzyme solutions were added, and absorbance measurements were taken at pre-determined time points. All conditions were prepared and measured in quadruplicate.

Caspase 3/8+Trypsin Assay

Caspase 3 was taken directly from stock solution containing 1000 U/µL. A stock solution of trypsin was prepared by dissolving the enzyme (5 mg/ml) in 1 mM HCl. The peptide substrates were dissolved in DMSO to make 10 mM solutions. These were then diluted to 2.5 mM with pH 7.5 0.1 M HEPES containing 10 mM DTT, 2 mM EDTA, and 10% v/v glycerol. In a 96-well plate, 84 µL of buffer and 5 µL peptide were mixed together before measuring the absorbance at 405 nm to serve as a blank. 1 µL caspase-3 was added, and the plate was incubated at 23° C. for 12-24 hours and absorbance was measured again. Then, 5 µL trypsin were added to the well and absorbance measurements were taken at pre-determined time points. All conditions prepared and measured in triplicate. The same protocol was used for caspase 8 assays, adjusting peptide substrate concentration as needed.

Example 3

Additional Examples of Dual Enzyme Cleavable Peptides

Figure 12:
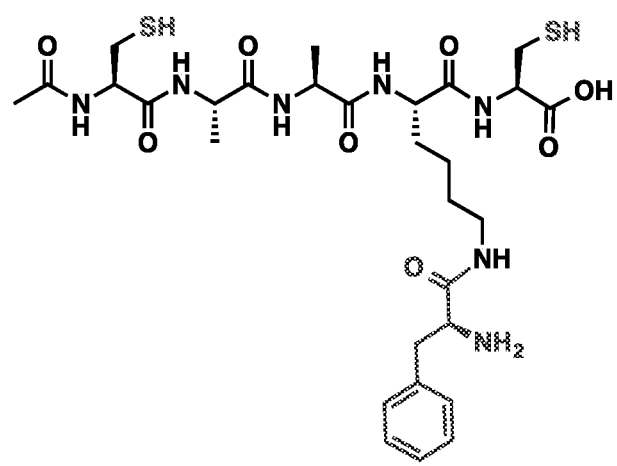
FIG. 12 is a formula showing chemical structure of one exemplary dual enzyme cleavable peptide according to embodiments of the present invention.

FIG. 12 shows one example of other dual enzyme cleavable peptides.

Synthesis of the Exemplary Dual Enzyme Cleavable Peptide.

Standard solid phase peptide synthesis conditions were used to synthesize the peptide cross-linker. 2-chlorotrityl chloride resin was loaded with Fmoc-Cysteine(Trityl) in the presence of a mild base, such as TEA. Fmoc-Lysine(Boc), Fmoc-Alanine, Fmoc-Alanine, and Fmoc-Cysteine(Trityl) were subsequently coupled to the loaded resin, and the amine terminus was acetylated prior to cleavage from the resin with TFA in DCM. The lysine side chain was modified by adding Boc-Phe-4-nitrophenylester in the presence of a mild base, triethylamine and purified by precipitation. Subsequent Boc and Trityl deprotection was carried out using 2.5% TIPS, 2.5% water in TFA, and the resulting peptide, generated as a TFA salt, was purified by precipitating into diethyl ether. Reverse phase HPLC was used to purify the peptide if precipitation did not remove all impurities.

Figure 13:
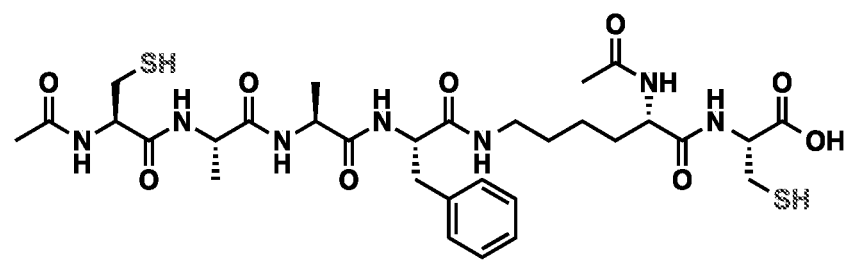
FIG. 13 is a formula showing chemical structure of another exemplary dual enzyme cleavable peptide according to embodiments of the present invention.

FIG. 13 shows another example of dual enzyme cleavable peptides.

Synthesis of the Exemplary Dual Enzyme Cleavable Peptide.

The drug will be loaded onto a 2-chlorotrityl chloride resin followed by coupling of Fmoc-Lysine(Boc) and Fmoc-Alanine. The peptide will be acetylated prior to cleavage from the resin and Boc deprotection with trifluoroacetic acid (TFA) in dichloromethane (DCM). The deprotected peptide will be precipitated into cold diethyl ether to remove impurities. The lysine side chain will be modified by adding Boc-Phe-4-nitrophenylester in the presence of a mild base, triethylamine. Subsequent Boc removal will be carried out with TFA in DCM, providing the peptide as a TFA salt that can be precipitated to purify. Reverse phase HPLC will be used if additional purification is needed.

Example 4

Peptides for Drug Release by Dual Enzyme Peptide Cleavage

Figure 14:
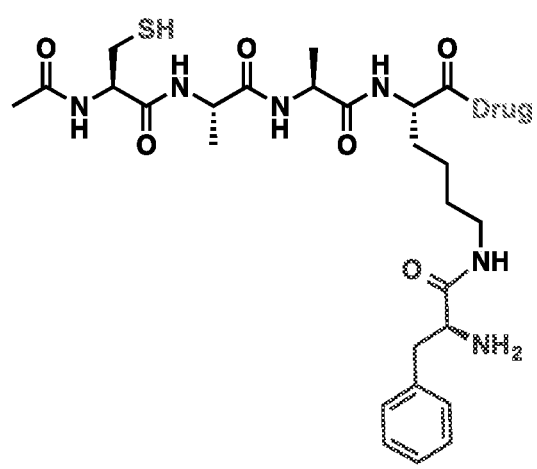
FIG. 14 is a formula showing chemical structure of one exemplary peptide for drug release by dual enzyme peptide cleavage according to embodiments of the present invention.

FIG. 14 shows one exemplary peptide with ester linkage to drug for drug release by dual enzyme peptide cleavage.

Synthesis of the Exemplary Peptide with Ester Linkage to Drug.

The drug-containing peptide will be synthesized using standard Fmoc solid phase peptide synthesis conditions. Fmoc-Lysine(Boc) will be loaded onto a 2-chlorotrityl chloride resin followed by two couplings of Fmoc-Alanine and Fmoc-Cysteine(Trityl). The peptide will be acetylated prior to cleavage from the resin and Boc deprotection with trifluoroacetic acid (TFA) in dichloromethane (DCM). The lysine side chain will be modified by adding Boc-Phe-4-nitrophenylester in the presence of a mild base, triethylamine and purified by precipitation. The drug compound will be added to the peptide using standard EDC coupling conditions. Subsequent Boc and trityl removal will be carried out with 2.5% triisopropylsilane (TIPS) and 2.5% water in TFA, providing the peptide as a TFA salt that can be precipitated to purify. Reverse phase HPLC will be used if additional purification is needed.

Figure 15:
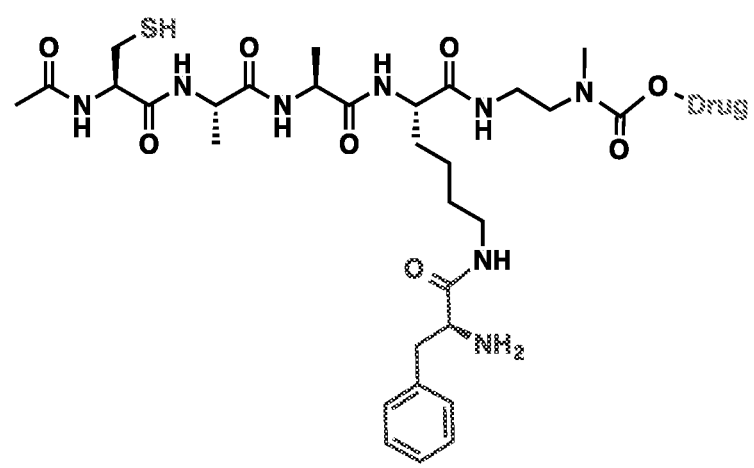
FIG. 15 is a formula showing chemical structure of another exemplary peptide for drug release by dual enzyme peptide cleavage according to embodiments of the present invention.

FIG. 15 shows one exemplary peptide with carbamate linkage to drug for drug release by dual enzyme peptide cleavage.

Synthesis of the Exemplary Peptide with Carbamate Linkage to Drug.

The drug-containing peptide will be synthesized using standard Fmoc solid phase peptide synthesis conditions. Fmoc-Lysine(Boc) will be loaded onto a 2-chlorotrityl chloride resin followed by two couplings of Fmoc-Alanine and Fmoc-Cysteine(Trityl). The peptide will be acetylated prior to cleavage from the resin and Boc deprotection with trifluoroacetic acid (TFA) in dichloromethane (DCM). The lysine side chain will be modified by adding Boc-Phe-4-nitrophenyl ester in the presence of a mild base, triethylamine and purified by precipitation. N-boc-N-methylethylenediamine will then be coupled to the C-terminus of the peptide using standard solution phase coupling conditions, which will then be coupled to a drug functionalized with an activated formate group, such as nitrophenylformate. Subsequent Boc and trityl removal will be carried out with 2.5% triisopropylsilane (TIPS) and 2.5% water in TFA, providing the peptide as a TFA salt that can be precipitated to purify. Reverse phase HPLC will be used if additional purification is needed.

Example 5

Noncrushable Cross-Linked Polymer for Non-Abusable Formulations

Figure 30:
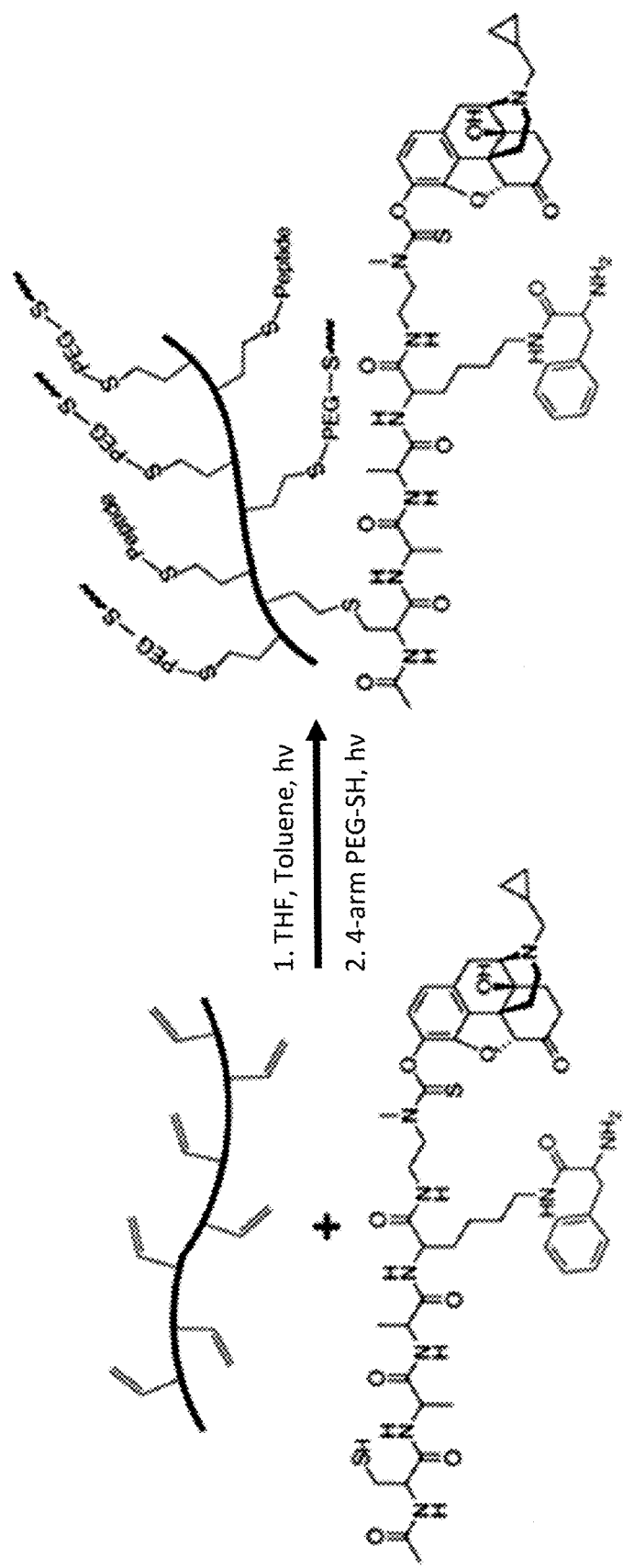
FIG. 30 is a scheme showing a noncrushable cross-linked polymer for non-abusable formulations.
Figure 30:
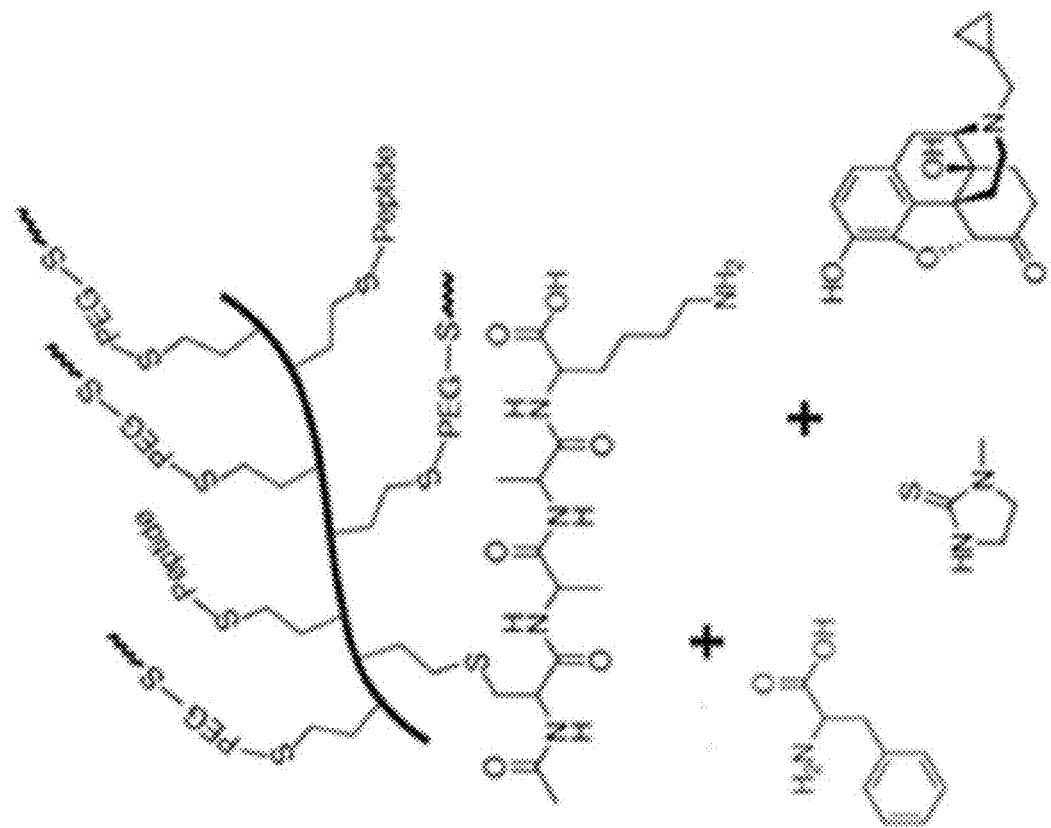
Figure 30:
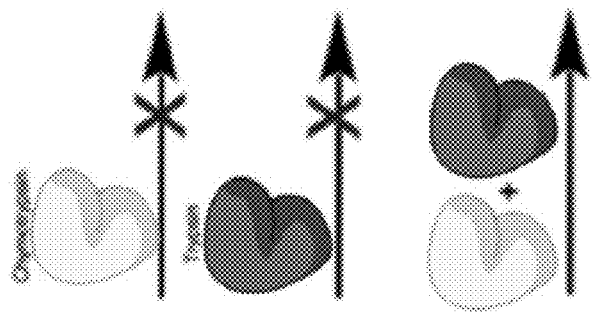

With abuse of prescription opioids so prevalent in society, a need has developed for non-abusable formulations. Many current methods of abuse include tampering with presently available formulations to increase the immediate dose to the user. To this end, we have developed an enzymatically triggered drug release system using a dual enzyme responsive peptide-drug conjugate resistant to "dose-dumping" coupled with a cross-linked polymer to resist crushing for nasal infusion. Specifically, the drug is linked to the non-crushable cross-linked polymer via a peptide linker that can only be cleaved by enzymes found in the small intestine. The peptide was prepared by masking the trypsin substrate, lysine, at the ε-amine with a second enzyme substrate and incorporating a self-immolative linker at the C-terminus. This was then conjugated to the drug through either a carbamate or thionocarbamate linker. The inclusion of a cysteine moiety allows for thiol-ene conjugation to siloxane polymers. As a proof of concept, Naltrexone was used as a model drug of the opioid family, which was conjugated to a polydimethylsiloxane (PDMS) copolymer containing 12% vinyl groups. This material was then cross-linked with 4-arm polyethylene glycol (PEG-SH) forming a rigid cross-linked network resistive to mechanical stress under a variety of conditions. An exemplary noncrushable cross-linked polymer for non-abusable formulations and a scheme for its preparation and use are illustrated in FIG. 30.

Peptide Synthesis

All peptides were prepared according to the scheme shown below. Peptides were prepared using standard Fmoc (fluorenylmethyloxycarbonyl) solid phase peptide synthesis using a 2-chlorotrityl resin (0.8 mmol/g loading). The N-termini were acetylated prior to cleavage using 50 eq of acetic anhydride and N,N-diisopropyl ethylamine (DIPEA) in N,N-dimethylformamide (DMF). The peptides were then cleaved from resin using a 50:50 mixture of trifluoroacetic acid (TFA) and DCM, which maintains the trityl protecting groups while unmasking the ε-amine of the lysine. The peptide was characterized and confirmed utilizing electrospray ionization mass spectrometry (ESI-MS).

Scheme 7. Fmoc solid phase peptide synthesis forming the peptide used in all the following conjugations.

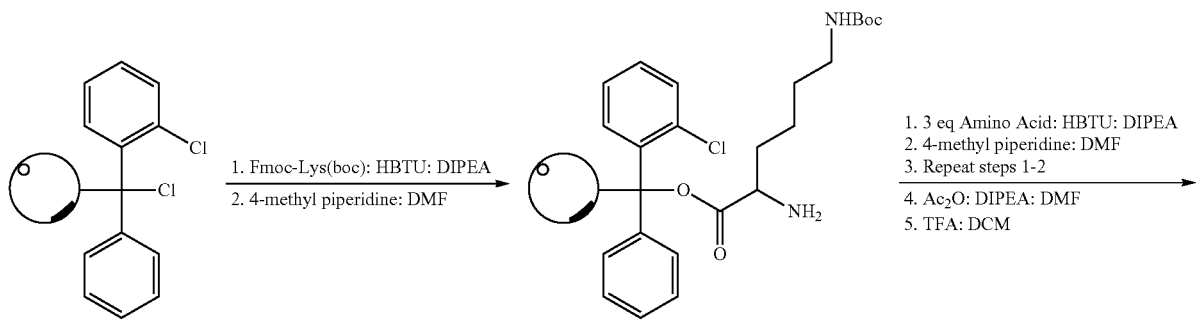

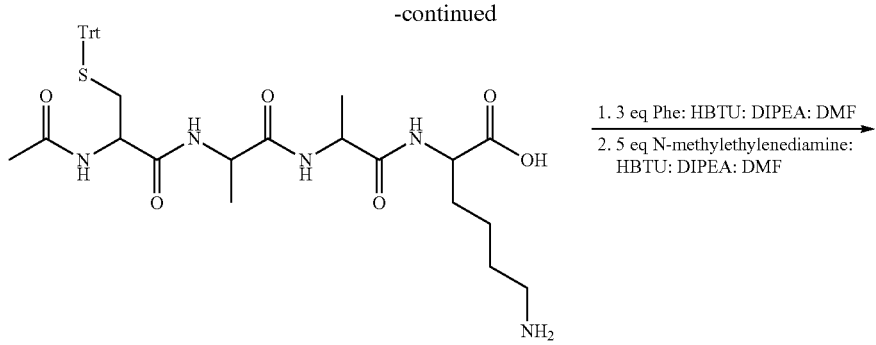

1. 3 eq Phe: HBTU: DIPEA: DMF
2. 5 eq N-methylethylenediamine: HBTU: DIPEA: DMF

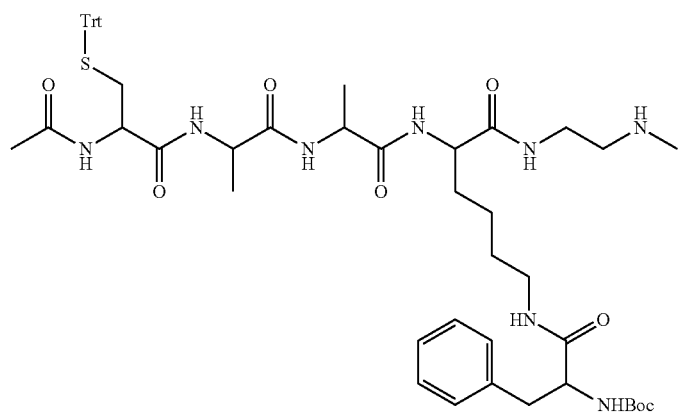

This ε-amine of the lysine was then masked using a solution-phase coupling reaction of the peptide with Boc-Phenylalanine (3 eq), N,N,N'N'-tetramethyl-O-(1-H-benzotriazol-1-yl)uranium hexafluorophosphate (HBTU) (3 eq), and DIPEA (5 eq). This material was then purified using high performance liquid chromatography (HPLC) equipped with a C18 column running a 70/30% to 5/95% $H_2O$/MeCN (acetonitrile) gradient with 0.1% TFA (trifluoroacetic acid) over 20 minutes with a 5-minute isocratic hold at 95% MeCN (20 mL/min). ESI-MS was used to confirm product identity.

The N-methylethylenediamine was then added to the C-terminus through another solution phase coupling reaction. The peptide was combined with HBTU (1.5 eq) and DIPEA (5 eq) to activate this carboxyl group. The N-methylethylenediamine was then added dropwise (5 eq) to form the desired product shown below. This was purified using HPLC equipped with a C18 column running a 70/30% to 5/95% $H_2O$/MeCN gradient with 0.1% TFA over 20 minutes with a 5-minute isocratic hold at 95% MeCN (20 mL/min). ESI-MS was used to confirm product identity.

Scheme 8. Conjugation of nitrophenylchloroformate to the diamine modified C-terminus through a carbamate linker.

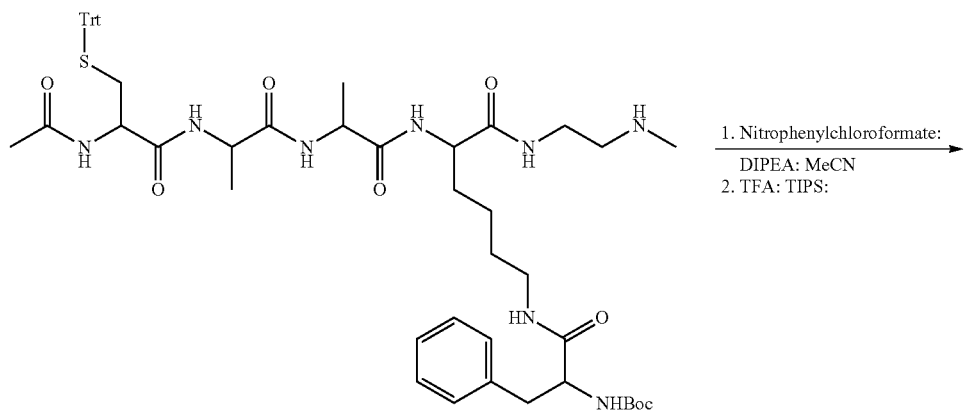

1. Nitrophenylchloroformate: DIPEA: MeCN
2. TFA: TIPS:

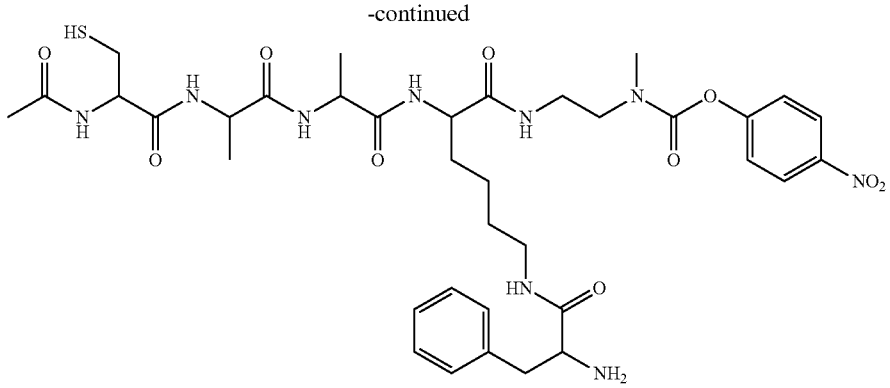

The diamine-conjugated peptide could then be attached to a colorimetric compound through a carbamate linker. This material allows for monitoring of enzymatic cleavage through the absorbance at 405 nm. The coupling was carried out in MeCN; followed by purification using HPLC equipped with a C18 column running a 70/30% to 5/95% H2O/MeCN gradient with 0.1% TFA over 18 minutes with a 5-minute isocratic hold at 95% MeCN (3 mL/min). ESI-MS was used to confirm product identity. The material was then deprotected using a solution of 95% TFA, 2.5% TIPS (triisopropylsilane), and 2.5% H$_2$O. The solution was then concentrated under vacuum and precipitated into cold ether to yield the deprotected peptide. ESI-MS was confirmed the product identity.

Preparation of Modified Naltrexone and Conjugation of Naltrexone to Peptide

The phenol of Naltrexone was modified using either 4-nitrophenyl chloroformate or pentafluorophenyl chlorothionoformate to produce the corresponding carbonate or thionocarbonate, respectively. This was done using either the free base of Naltrexone or the HCl salt. In a typical procedure, Naltrexone (1 eq), either as the freebase or HCl salt, was dissolved in dry dichloromethane under an Argon atmosphere with magnetic stirring. N,N-diisopropylethylamine (2.5 eq) was then added and stirred for 5 minutes before adding either 4-nitrophenylchloroformate or pentafluorophenyl chlorothionoformate (2 eq) to produce the corresponding carbonate or thionocarbonate, respectively. After 18 hours, the modified Naltrexone product was purified by flash column chromatography using a solvent system of 2-20% acetone in dichloromethane. Typical yields ranged from 83-87% and products were yellow/orange solids. The identities of the desired products were confirmed using 1H NMR, 13C NMR, and ESI-MS.

Scheme 9. Synthesis of Naltrexone O-pentafluorophenyl carbonothioate (top) and Naltrexone 4-nitrophenyl carbonate (bottom).

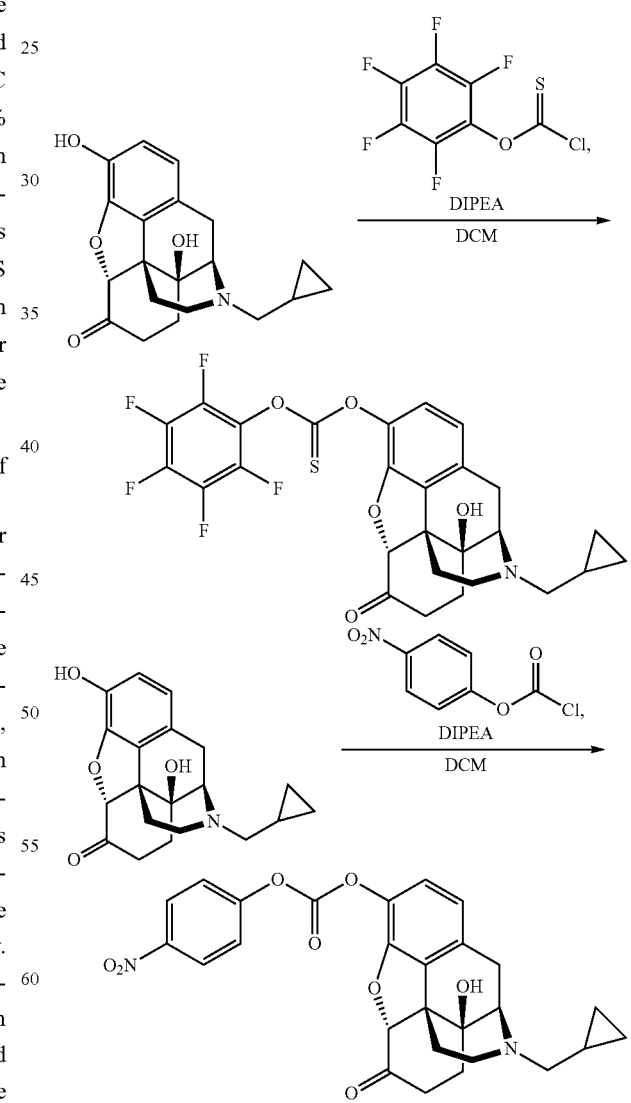

Figure 32:
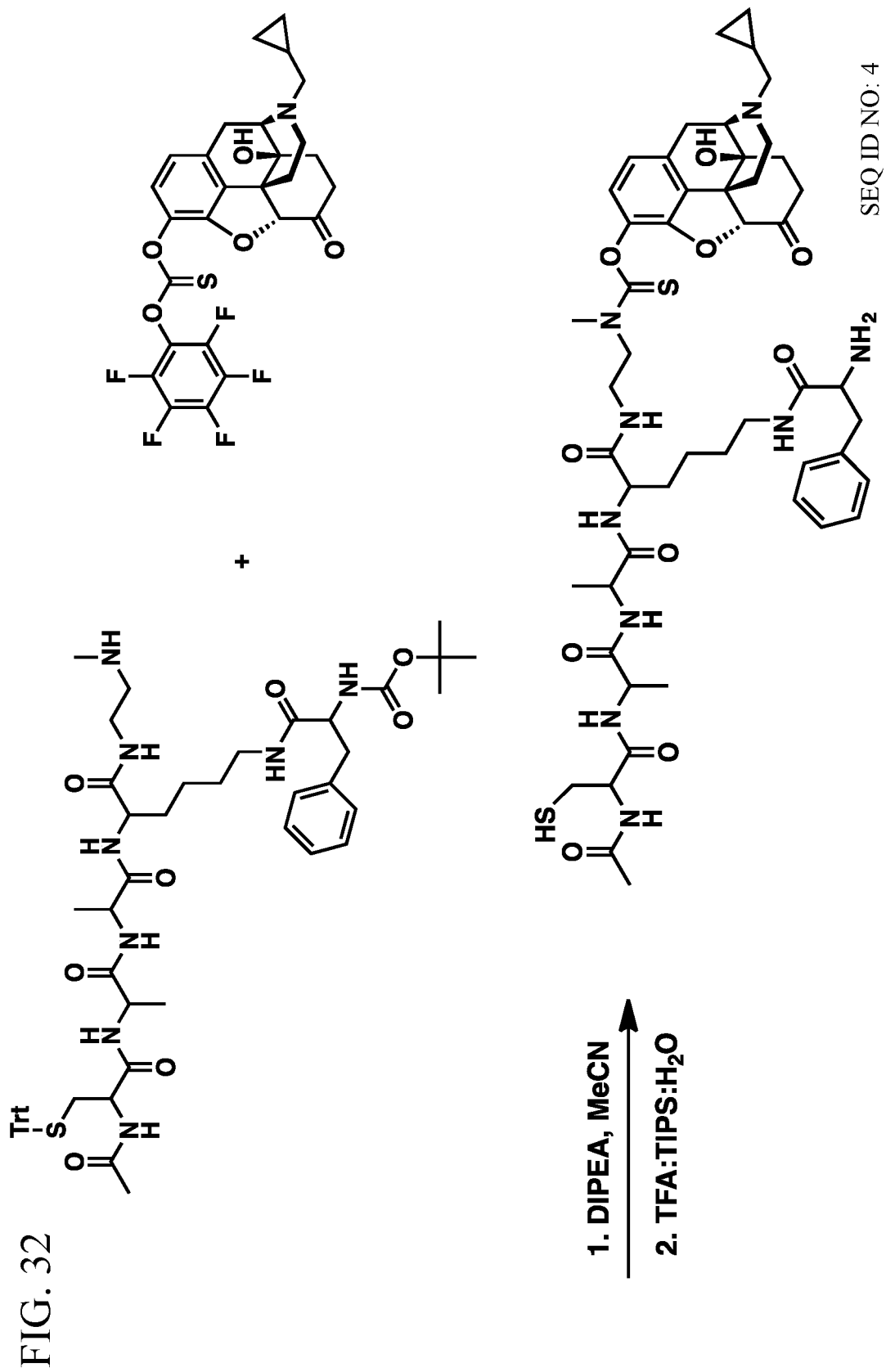
FIG. 32 is a scheme showing synthesis of CAAK(F)-diamino-Naltrexone thionocarbamate (SEQ ID NO: 4) and CAAK(F)-diamino-Naltrexone carbamate (SEQ ID NO: 4).
Figure 32:
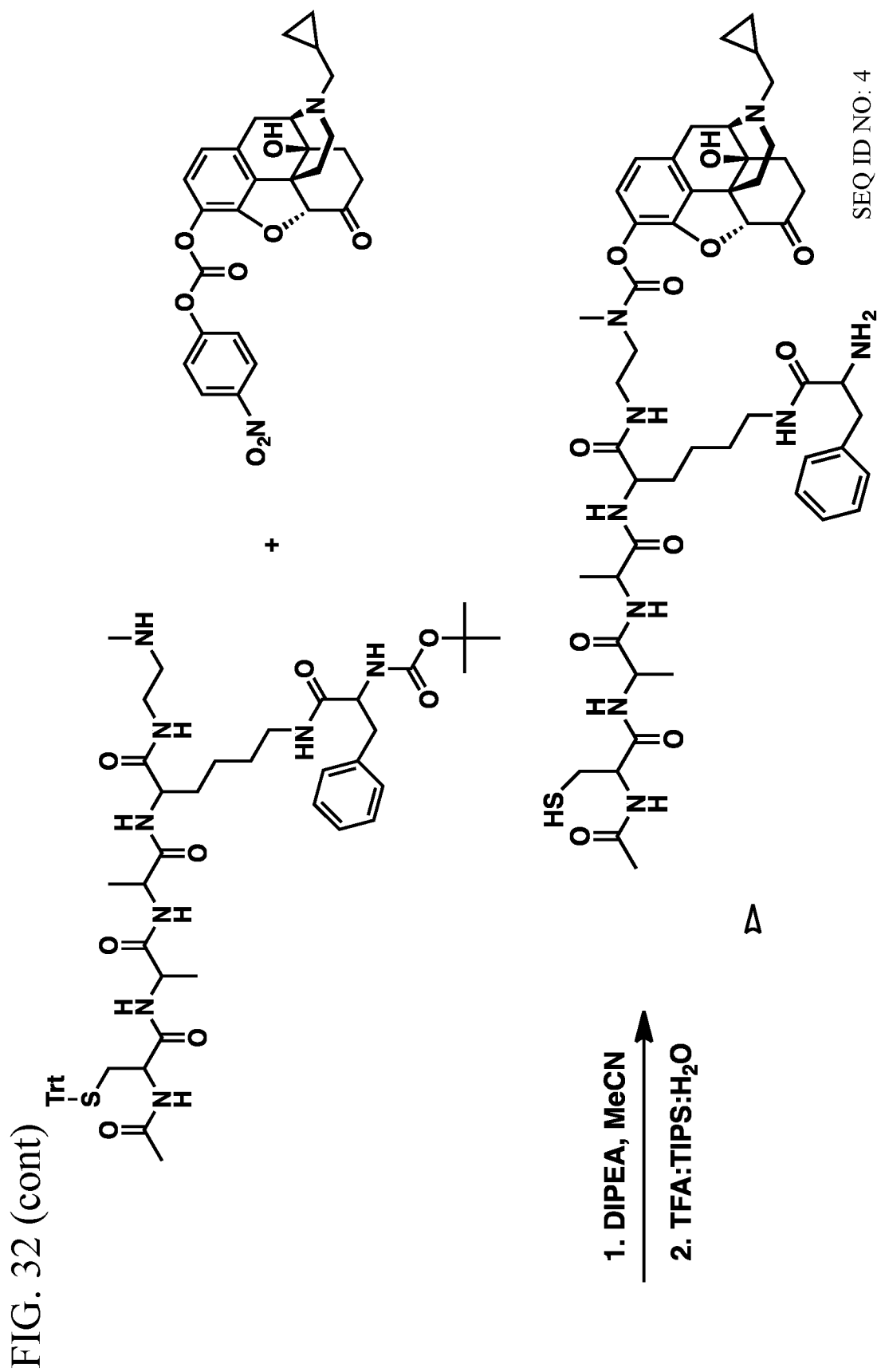

Each modified Naltrexone was then coupled onto the CAAK(F) (SEQ ID NO: 4) peptide containing the C-terminal diamino linker by first dissolving the peptide in acetonitrile under magnetic stirring followed by addition of the modified Naltrexone (2 eq) and N,N-diisopropylethylamine (2.5 eq). After 3 hours, solvent was removed under vacuum and redissolved into a mixture of water and acetonitrile and purified by HPLC equipped with a C18 column running a 90/10% to 0/100% H₂O/MeCN gradient with 0.1% TFA over 15 minutes followed by a 5-minute isocratic hold at 100% MeCN with 0.1% TFA. Subsequent deprotection of the peptides was carried out using a solution of 95% TFA, 2.5% TIPS, and 2.5% H₂O. The solutions were then concentrated under vacuum and precipitated into cold ether to produce the deprotected peptide. The desired products were collected and confirmed using ESI-MS. An exemplary schematic of the synthesis synthesis of CAAK(F)-diamino-Naltrexone thionocarbamate (SEQ ID NO: 4) and CAAK (F)-diamino-Naltrexone carbamate (SEQ ID NO: 4) is illustrated in FIG. 32.

Elastomer Synthesis

Figure 33:
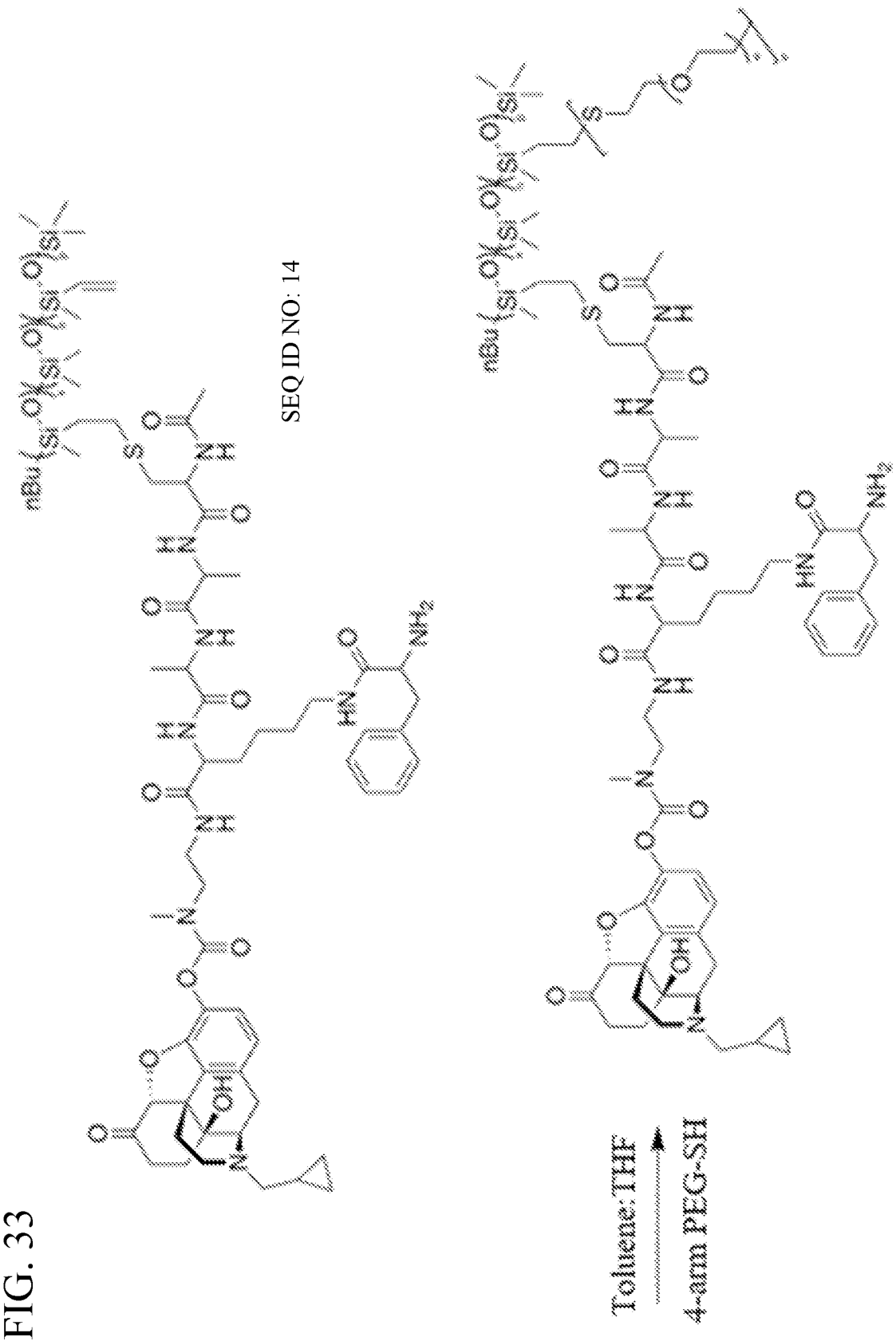
FIG. 33 is a scheme showing crosslinking of the PDMS-CAAK(F)-diamino-Naltrexone-polysiloxane (SEQ ID NO: 14) conjugate with 4-arm PEG-SH.

The PDMS copolymer with 12% vinyl groups was dissolved in minimal toluene. Separately the peptide-Naltrexone conjugate (1 eq to vinyl groups) was combined with Irgacure 2959 (0.2 eq to vinyl groups) and dissolved in (1:2 parts toluene:tetrahydrofuran THF). The solution was then freeze-pump-thawed three times, sealed under argon, and irradiated under UV light (365 nm) for minutes. An exemplary schematic of the crosslinking of PDMS-CAAK(F) diamino-Naltrexone-polysiloxane (SEQ ID NO: 14) conjugate with 4-arm PEG-SH is illustrated in FIG. 33. After the UV irradiation, the reaction was quenched by exposing it to oxygen. 4-arm PEG-SH (0.5 eq SH to every vinyl group) and Irgacure 2959 (0.1 eq to vinyl groups) was dissolved in minimal THF. This solution was then added to polymer-peptide conjugate and this was again freeze-pump-thawed three times, sealed under argon, and irradiated with UV light (365 nm) for an additional 90 minutes. This was then quenched by exposing to oxygen and the solvent was removed under vacuum, producing a rigid elastomer. The elastomer was tested on its resistance to mechanical stress (via crushing with a hammer and shaving with a razor) under various conditions. The elastomer remained noncrushable upon testing after it was cooled to 4° C. for 12/24 hours, cooled to −20° C. for 12/24 hours, heated to 260° C. for 15/30/60 minutes, and microwaved for up to minutes.

Figure 16:
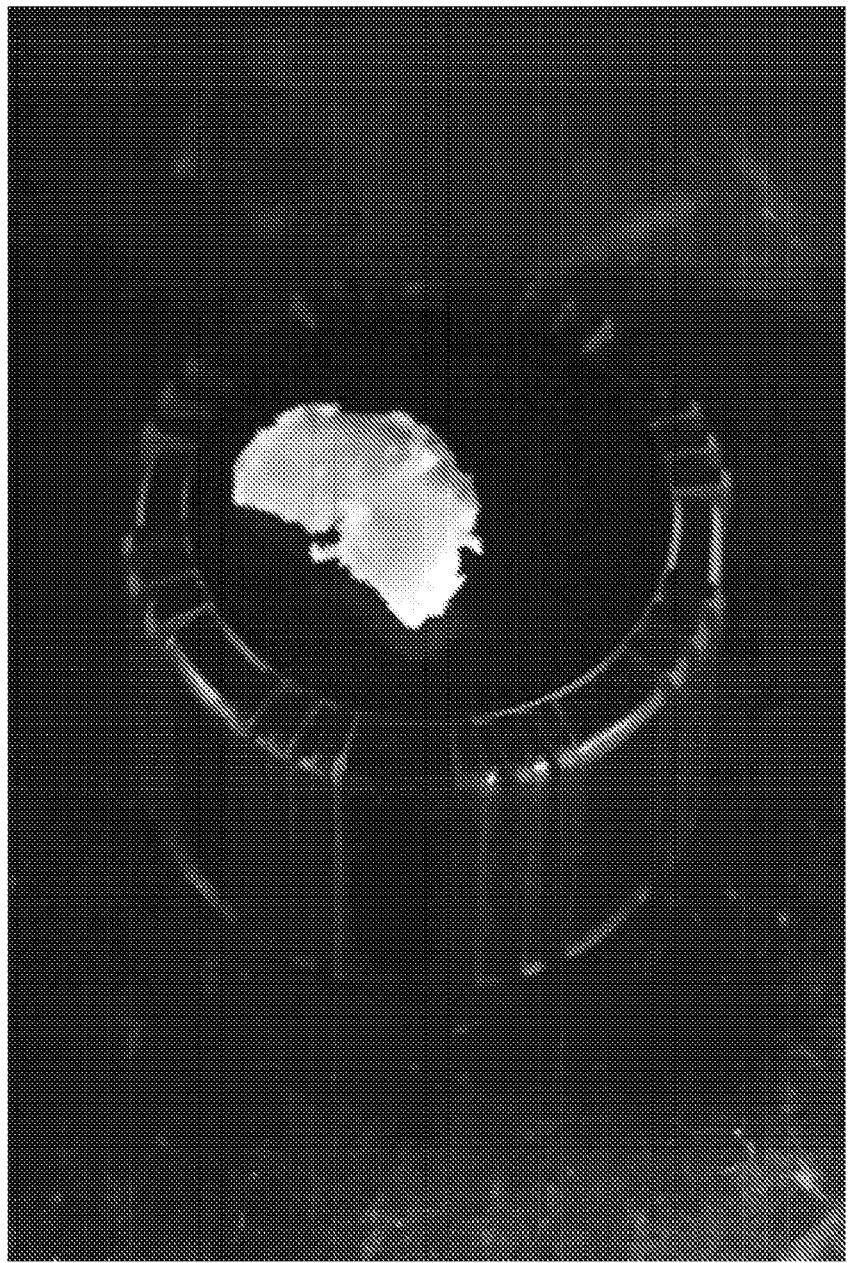
FIG. 16 is an image showing that elastomer containing CAAK(F)-diamino-Naltrexone (SEQ ID NO: 5) conjugated onto PDMS cross-linked using 4-arm PEG-SH.

FIG. 16 shows an image of the Elastomer containing CAAK(F)-diamino-Naltrexone (SEQ ID NO: 4) conjugated onto PDMS cross-linked using 4-arm PEG-SH.

Peptides Preparation and Characterization:

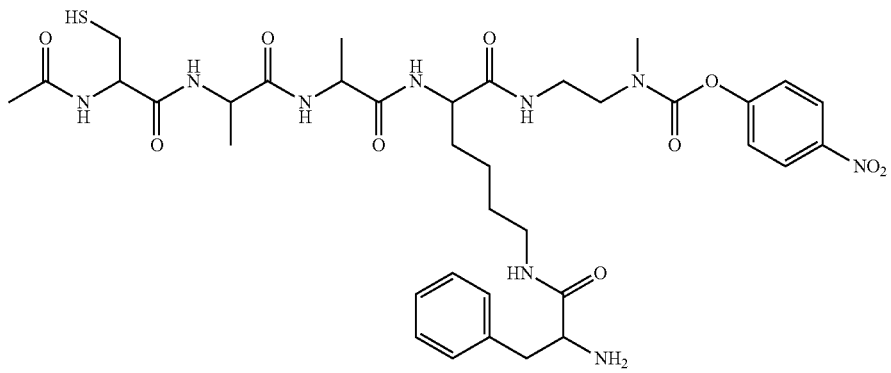 [SMILES: CC(=O)NC(CS)C(=O)NC(C)C(=O)NC(C)C(=O)NC(CCCCNC(=O)C(N)Cc1ccccc1)C(=O)NCCN(C)C(=O)Oc1ccc([N+](=O)[O-])cc1]

CAAK(F)-diamino-pNA (SEQ ID NO: 4)
Calc. [M+]: 802.3573 Observed [M+]: 802.3361

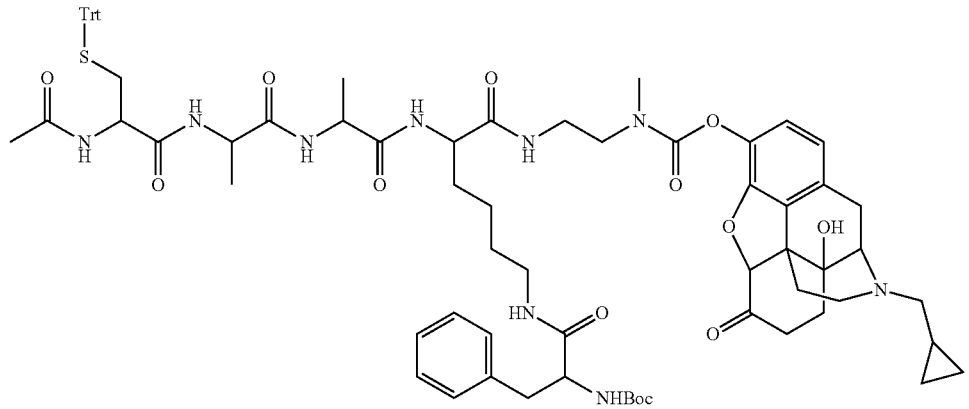

CAAK(F)-diamino-Naltrexone (carbamate-linked) (SEQ ID NO: 4)
Calc. [M+]: 1368.6392 Observed [M+]: 1368.5975

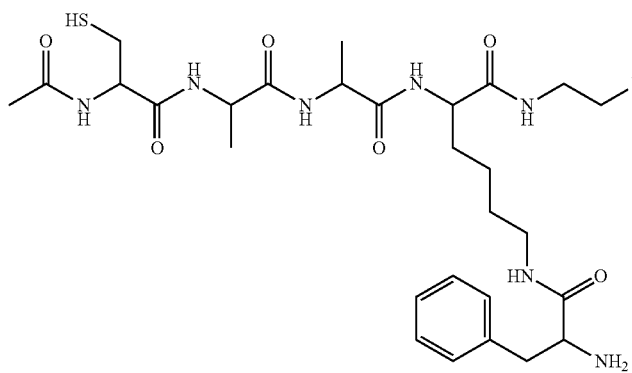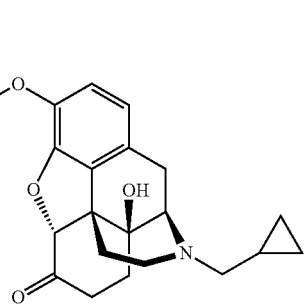

CAAK(F)-diamino-Naltrexone (thionocarbamate-linked) (SEQ ID NO: 4)

Calc. [M+Na]: 1042.4492 Observed [M+Na]: 1042.4596 pNA Release Assay

A stock solution of the CAAK(F)-diamino-pNA (SEQ ID NO: 4) was prepared in dimethyl sulfoxide (DMSO) to produce a 16.0 mg/mL solution. A 7.5 mg/mL stock solution of the trypsin was prepared in 50 mM $NH_4HCO_3$ buffer (pH=8.05). A 7.5 mg/mL stock solution of chymotrypsin was prepared in 50 mM $NH_4HCO_3$ buffer (pH=8.05).

A 96 well plate was used for monitoring the solutions at 405 nm using a plate reader. 20 µL of the peptide was combined with 62.0/66.6 µL of no enzyme, trypsin only, chymotrypsin only, or with both enzymes respectively. All solutions were diluted to a total volume of 200 µL using 50 mM $NH_4HCO_3$ (pH=8.05). Blanks were prepared by combining the enzymes with DMSO/buffer and their absorbances were subtracted from the cleavage conditions. Additionally, the residual signal from the peptide in the presence of no enzymes was also used as a blank and subtracted out from enzymatic conditions.

Figure 17:
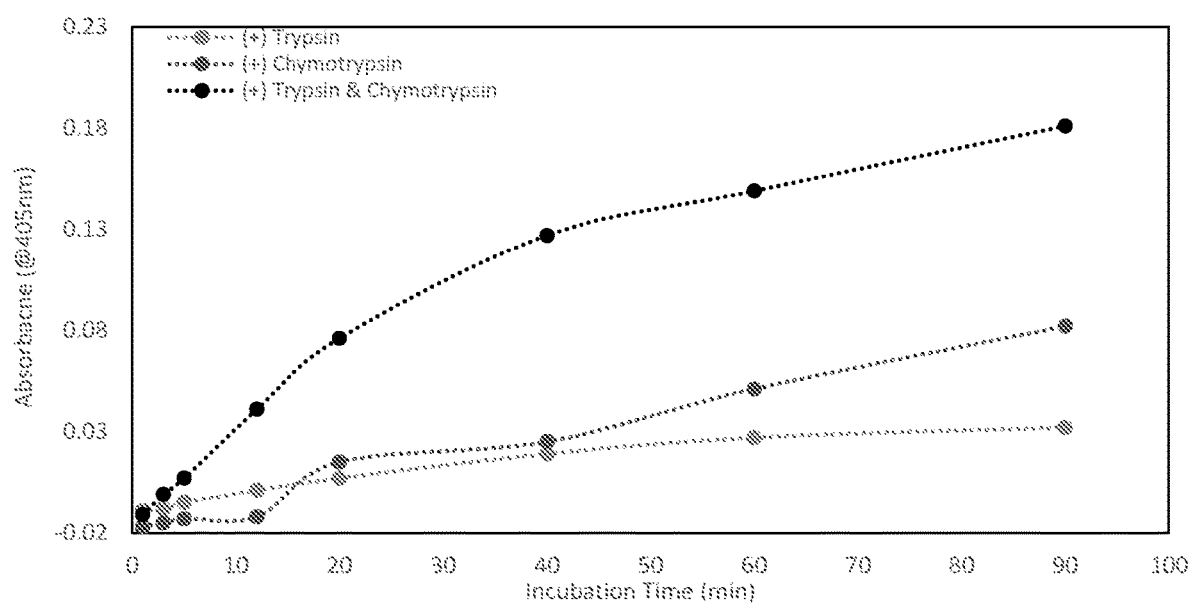
FIG. 17 is a graph showing that 2 mM CAAK(F)-diamino-pNA (SEQ ID NO: 5) was incubated with trypsin and/or chymotrypsin for 90 minutes at 37° C. 55% of the theoretical pNA was released after 90 minutes of incubation.

FIG. 17 shows that 2 mM CAAK(F)-diamino-pNA (SEQ ID NO: 4) was incubated with trypsin and/or chymotrypsin for 90 minutes at 37° C. 55% of the theoretical pNA was released after 90 minutes of incubation.

Naltrexone Release Assay

A stock solution of the peptide was prepared in DMSO to produce a 20.0 mg/mL solution. A 11.65 mg/mL stock solution of the trypsin was prepared in 50 mM $NH_4HCO_3$ buffer (pH=8.05). A 12.5 mg/mL stock solution of chymotrypsin was prepared in 50 mM $NH_4HCO_3$ buffer (pH=8.05).

50 µL of the peptide solution was combined with 100 µL of either/both enzymes into an Eppendorf low-bind tube and diluted to 500 µL with $NH_4HCO_3$ buffer (pH=8.05). Blanks were prepared by combining the enzymes with DMSO/buffer and their absorbances were subtracted from the cleavage conditions. The residual signal from the peptide in the presence of no enzymes was also used as a blank and subtracted out from enzymatic conditions. The solutions were placed in an incubator at 37° C. for the remainder of the experiment. Aliquots were removed from the sample over the course of the experiment. 50 µL aliquots were combined with 50 µL of a quenching solution (1 mg/mL TCEP, 2.5% TFA, 48.75% $H_2O$, 48.75 MeCN) bringing the pH of the solution below the active range of the proteases while keeping the peptide reduced. These solutions were then filtered and run on a C18 analytical HPLC using a 70/30% to 5/95% $H_2O$/MeCN gradient with 0.1% TFA over 15 minutes with a 5-minute isocratic hold at 95% MeCN (3 mL/min). The cleavage was monitored by integrating the appearance of a peak at 5.8 min corresponding to the same retention time as Naltrexone run under identical conditions.

Figure 18:
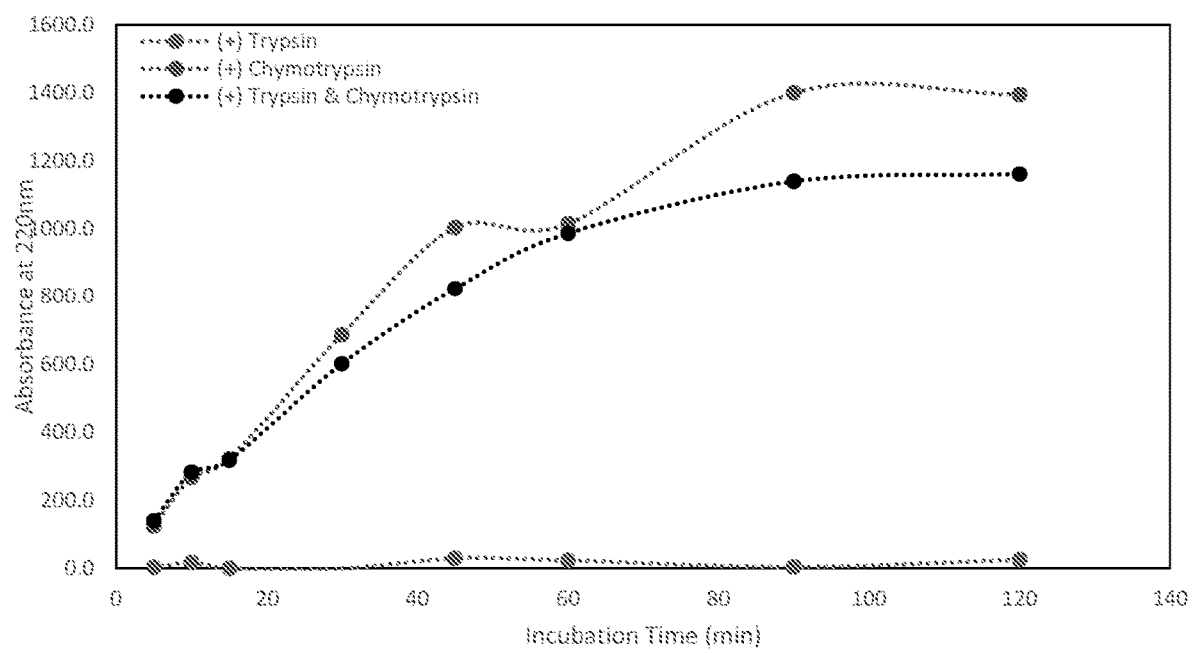
FIG. 18 is a graph showing that 2 mM CAAK(F)-diamino-Naltrexone (carbamate-linked) (SEQ ID NO: 5) was incubated with trypsin and/or chymotrypsin for 120 minutes at 37° C.

FIG. 18 shows the results when 2 mM CAAK(F)-diamino-Naltrexone (carbamate-linked) (SEQ ID NO: 4) was incubated with trypsin and/or chymotrypsin for 120 minutes at 37° C.

Figure 19:
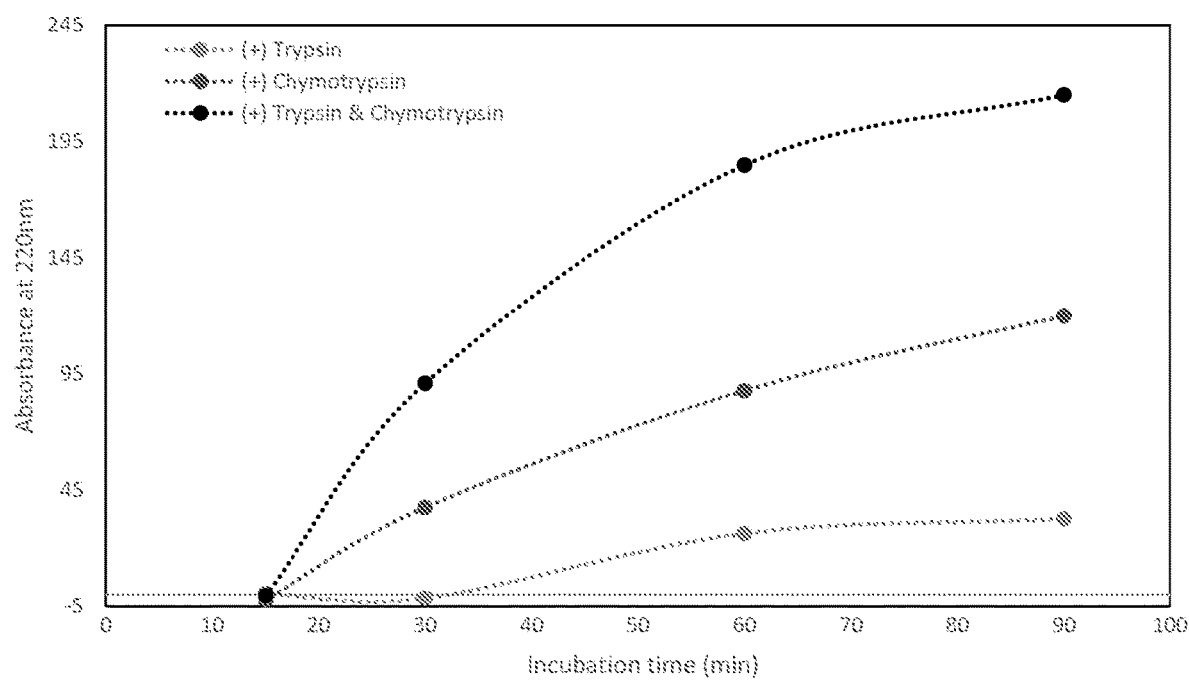
FIG. 19 is a graph showing that 2 mM CAAK(F)-diamino-Naltrexone (thionocarbamate-linked) (SEQ ID NO: 5) was incubated with trypsin and/or chymotrypsin for 90 minutes at 37° C.

FIG. 19 shows the results when 2 mM CAAK(F)-diamino-Naltrexone (thionocarbamate-linked) (SEQ ID NO: 4) was incubated with trypsin and/or chymotrypsin for 90 minutes at 37° C.

Example 6

Alternative Methods for Naltrexone Activation

Naltrexone Activation

The ketone of Naltrexone could only be modified after first protecting its phenol as a phenyl methyl ether. The phenol was methylated by dissolving Naltrexone (1 eq) in 10 ml DCM and then adding potassium carbonate (5 eq) followed by iodomethane (20 eq). The reaction was stirred for 18 hours and then diluted with DCM and washed several times with a mixture of water and saturated bicarbonate solution followed by drying over magnesium sulfate and concentration under vacuum. The product, 0-Me Naltrexone, was recovered in quantitative yield. The ketone of Naltrexone was then modified by first dissolving potassium bis(trimethylsilyl)amide (KHMDS; 3 eq) in 5 ml of dry dimethoxyethylene glycol (DME) in an oven dried flask under Argon and then cooling the mixture to −78° C. in a dry ice/acetone bath. O-Me Naltrexone (1 eq) was added dropwise in 2 ml of thy DME and stirred at −78° C. for 30 minutes. Meanwhile, pentafluorophenyl chlorothionoformate (3 eq) was dissolved in a separate oven dried flask followed by boron trifluoride etherate (3 eq). The solution was then cooled to −78° C. in a dry ice/acetone bath for 15 minutes. Next, the solution containing O-Me Naltrexone was cannulated into the other flask and the entire mixture was allowed to stir at −78° C. for 30 minutes and then for minutes after removal from the bath. The reaction was then concentrated under vacuum and redissolved in a minimal amount of DCM and precipitated three times in hexanes. Finally, the desired product was recovered by dissolving the remaining material in approximately 60% acetonitrile and purifying it by HPLC using a gradient of 40/60% to 5/95% H2O/acetonitrile gradient with 0.1% TFA over 15 minutes followed by a 5-minute isocratic hold at 95% acetonitrile with 0.1% TFA. Typical yields were around 11% and so the reaction needs to be scaled. The identities of the desired products were confirmed using 1H NMR, 13C NMR, and ESI-MS.

Scheme 12. Synthesis of O—Me Naltrexone Enol Pentafluorophenylthionocarbonate.

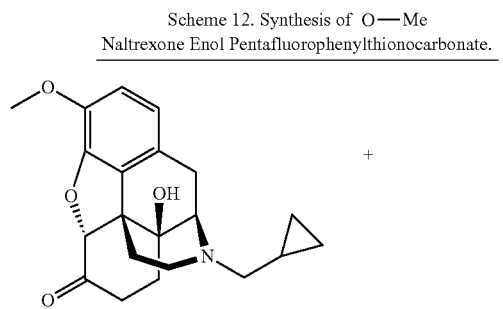

+

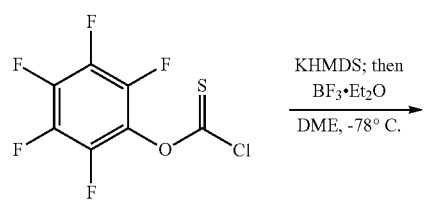

KHMDS; then BF$_3$·Et$_2$O
DME, -78° C.

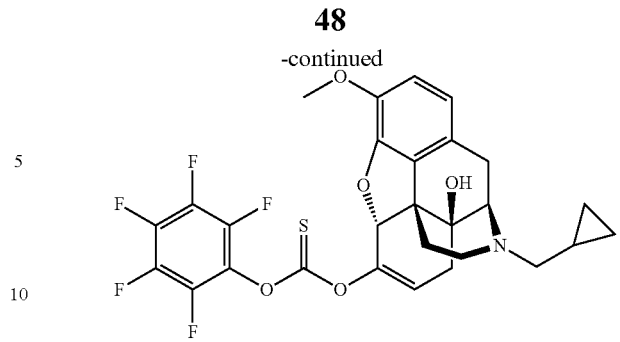

-continued

Naltrexone Conjugation to the Peptide

Each modified Naltrexone was then coupled onto the CAAK(F) peptide (SEQ ED NO: 4) containing the C-terminal diamino linker by first dissolving the peptide in acetonitrile under magnetic stirring followed by addition of the modified Naltrexone (2 eq) and DIPEA (2.5 eq). After 3 hours, solvent was removed under vacuum and redissolved into a mixture of water and acetonitrile and purified by HPLC equipped with a C18 column running a 90/10% to 0/100% H$_2$O/acetonitrile gradient with 0.1% TFA over 15 minutes followed by a 5-minute isocratic hold at 100% acetonitrile with 0.1% TFA. Subsequent deprotection of the peptides was carried out using a solution of 95% TFA, 2.5% TIPS, and 2.5% H$_2$O. This was then concentrated under vacuum and precipitated into cold ether to produce the deprotected peptide. The desired products were collected and confirmed using ESI-MS.

Scheme 13. Synthesis of CAAK(F)-diamino-Naltrexone enol thionocarbamate (SEQ ID NO: 4).

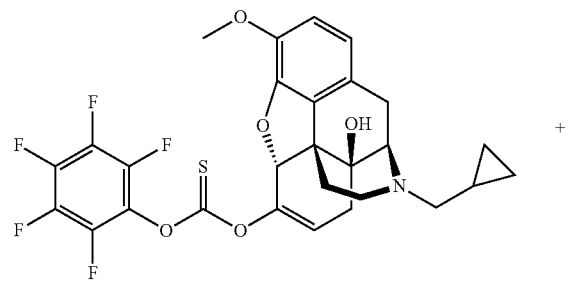

+

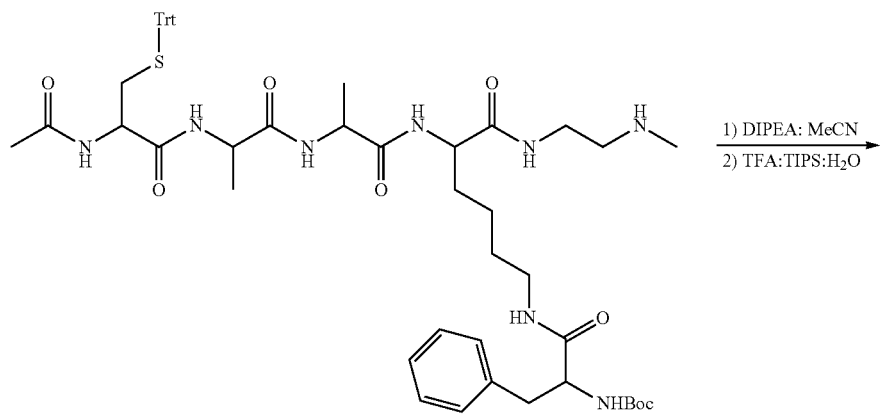

1) DIPEA: MeCN
2) TFA:TIPS:H$_2$O

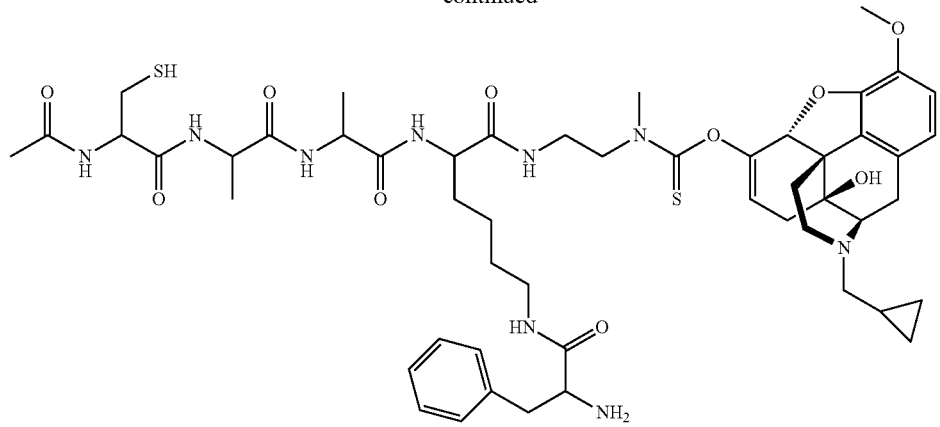

Stability Analysis

In order to determine the stability of the enzymatically cleavable covalent linkage between the dual-enzyme responsive peptide and Naltrexone, the drug conjugates (below) were synthesized and subjected to a range of different pH buffers that were chosen to emulate the pH range of typical household chemicals (pH 2-10).

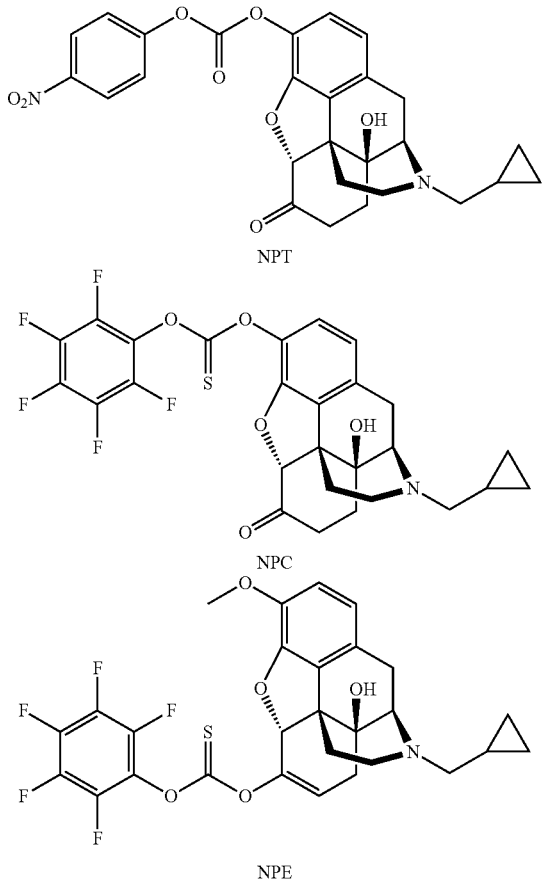

The stabilities of these linkages were assessed by HPLC by monitoring the relative amount of Naltrexone versus the intact peptide-Naltrexone conjugate. The thiocarbamate linker above (NPT, left) proved to be more stable than the carbamate linker (NPC, middle). The enol thionocarbamate linker (NPE, right) demonstrated similar stability to NPC. The NPC and NPE linker showed very good stability over the entire pH range and were therefore suitable for the elastomer. NPE was incorporated into the final elastomer formulation to demonstrate release. The stability data is shown in the Table 1 below.

TABLE 1

The stability data of NPT, NPC and NPE.

| Entry | Sample Name | Sample Retention Time (min) | Percent Degradation, t = 0.5 hr | Percent Degradation, t = 24 hr |
|---|---|---|---|---|
| 1 | Naltrexone | 5.908 | — | — |
| 2 | Naltrexone-Peptide Carbamate Linker (NPC) | 6.433 | 0 | 0 |
| 3 | NPC in pH 2 | 6.078/6.472 | 6.00 | 12.30 |
| 4 | NPC in pH 4 | 6.078/6.472 | 3.50 | 2.89 |
| 5 | NPC in pH 7 | 6.078/6.472 | 1.50 | 3.62 |
| 6 | NPC in pH 9 | 6.078/6.472 | 5.56 | 5.17 |
| 7 | NPC in pH 12 | 6.078/6.472 | 7.03 | 6.94 |
| 8 | Naltrexone-Peptide Thionocarbamate Linker (NPT) | 6.433 | 0.51 | 2.90 |
| 9 | NPT in pH 2 | 6.078/6.472 | 3.23 | 4.10 |
| 10 | NPT in pH 4 | 6.078/6.472 | 1.67 | 2.04 |
| 11 | NPT in pH 7 | 6.078/6.472 | 3.22 | 3.59 |
| 12 | NPT in pH 9 | 6.078/6.472 | 4.69 | 3.37 |
| 13 | NPT in pH 12 | 6.078/6.472 | 5.15 | 6.72 |
| 14 | O-Me Naltrexone | 6.688 | — | — |
| 15 | O-Me Naltrexone-Peptide Enol Thionocarbamate Linker (NPE) | 7.064 | 0 | 1.51 |
| 16 | NPE in pH 2 | 6.688/7.064 | 1.77 | 4.90 |
| 17 | NPE in pH 4 | 6.688/7.064 | 1.38 | 3.41 |
| 18 | NPE in pH 7 | 6.688/7.064 | 2.29 | 3.88 |
| 19 | NPE in pH 9 | 6.688/7.064 | 5.99 | 7.16 |
| 20 | NPE in pH 12 | 6.688/7.064 | 3.28 | 5.38 |

Elastomer Synthesis

Figure 34:
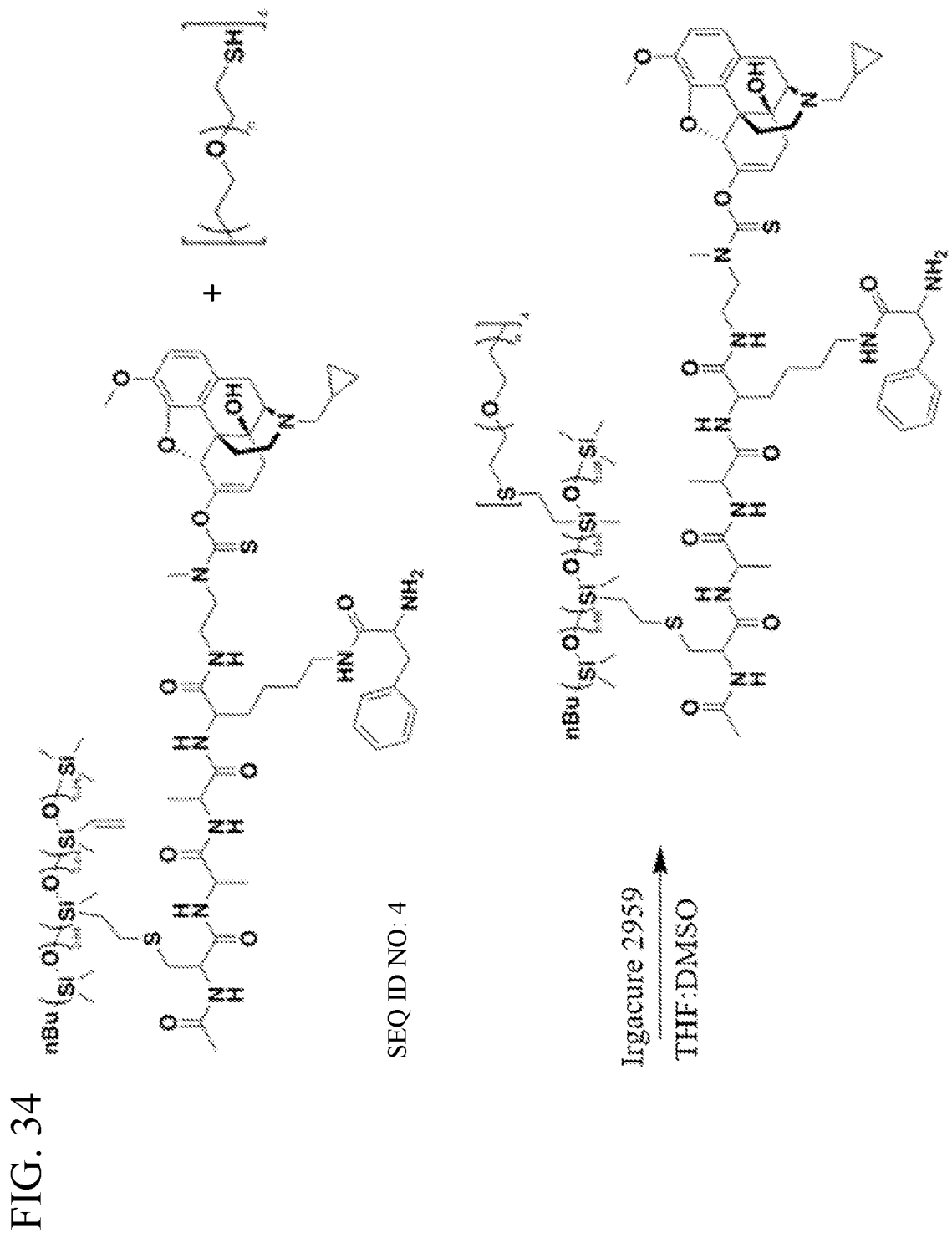
FIG. 34 is a scheme showing crosslinking of the PDMS-CAAK(F)-Naltrexone (SEQ ID NO: 4) conjugate with 4-arm PEG-SH.

The PDMS copolymer with 12% vinyl groups was dissolved in minimal toluene. Separately the peptide-Naltrexone conjugate (1 eq to vinyl groups) was combined with Irgacure 2959 (0.2 eq to vinyl groups) and dissolved in tetrahydrofuran (1:2 parts toluene:THF). The solution was then freeze-pump-thawed three times, sealed under argon, and irradiated under UV light (365 nm) for 50 minutes. An exemplary schematic of the crosslinking of the PDMS-CAAK(F)-Naltrexone (SEQ ID NO:4) conjugate with 4-PEG-SH is illustrated in FIG. 34.

After the UV irradiation, the reaction was quenched by exposing it to oxygen. Excess peptide was removed through dialysis using a solution of methanol and dichloromethane (30:70). This material was collected, residual solvent was removed under vacuum and it was dissolved in THF. 4-arm PEG-SH (0.5 eq SH to every vinyl group) and Irgacure 2959 (0.1 eq to vinyl groups) was dissolved in minimal THY. This solution was then added to the polymer-peptide conjugate and this was again freeze-pump-thawed three times, sealed under argon, and irradiated with UV light (365 nm) for an additional 90 minutes. This was then quenched by exposing to oxygen and the solvent was removed under vacuum, producing a rigid elastomer. The elastomer was tested on its resistance to mechanical stress (via crushing with a hammer and shaving with a razor) under various conditions. The elastomer remained rigid upon testing after it was cooled to 4° C. for 12/24 hours, cooled to −20° C. for 12/24 hours, heated to 260° C. for 15/30/60 minutes, and microwaved for up to 5 minutes.

Figure 20:
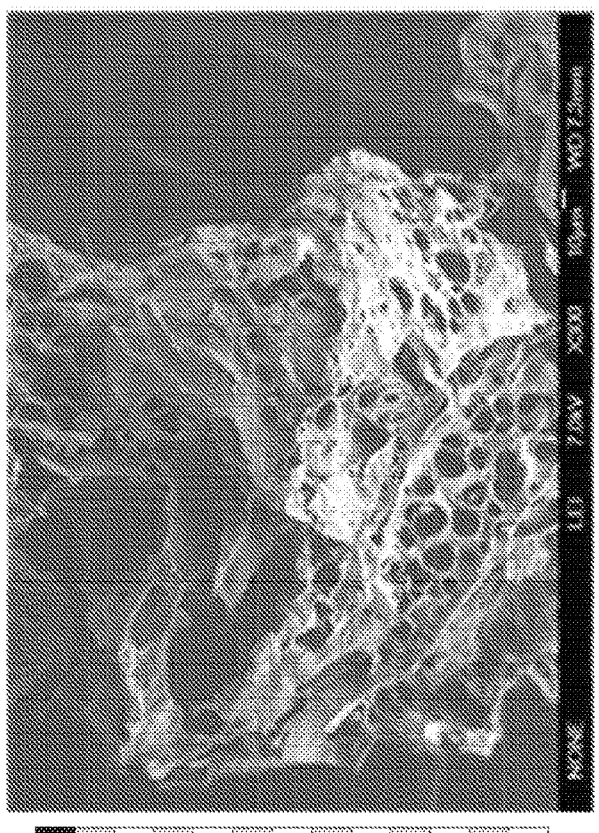
FIG. 20 are a table and an image showing that Physical rigidity of the elastomer containing CAAK(F)-diamino-Naltrexone (SEQ ID NO: 5) conjugated onto PDMS crosslinked using 4-arm PEG-SH against a variety of stresses and SEM images of final elastomer.

FIG. 20 shows that physical stability of the elastomer containing CAAK(F)-diamino-Naltrexone (SEQ ID NO: 4) conjugated onto PDMS crosslinked using 4-arm PEG-SH against a variety of stresses and SEM images of final elastomer.

Enzyme-Triggered Naltrexone Release

Peptide/elastomer was dissolved in DMSO and diluted using $NH_4HCO_3$ buffer (pH=8.05). Four solutions were prepared by adding either; no protease, trypsin only, chymotrypsin only, or both proteases. The solutions were placed in an incubator at 37° C. for the remainder of the experiment. Aliquots were removed from the samples over the course of the experiment. These solutions were then filtered and run on a C18 analytical HPLC using a 70/30% to 5/95% $H_2O$/acetonitrile gradient with 0.1% TFA over 15 minutes with a 5-minute isocratic hold at 95% acetonitrile (1.2 mL/min). The cleavage was monitored by integrating the appearance of the 0-Me Naltrexone peak at 9 min. Naltrexone appearance was confirmed using LCMS.

Figure 21:
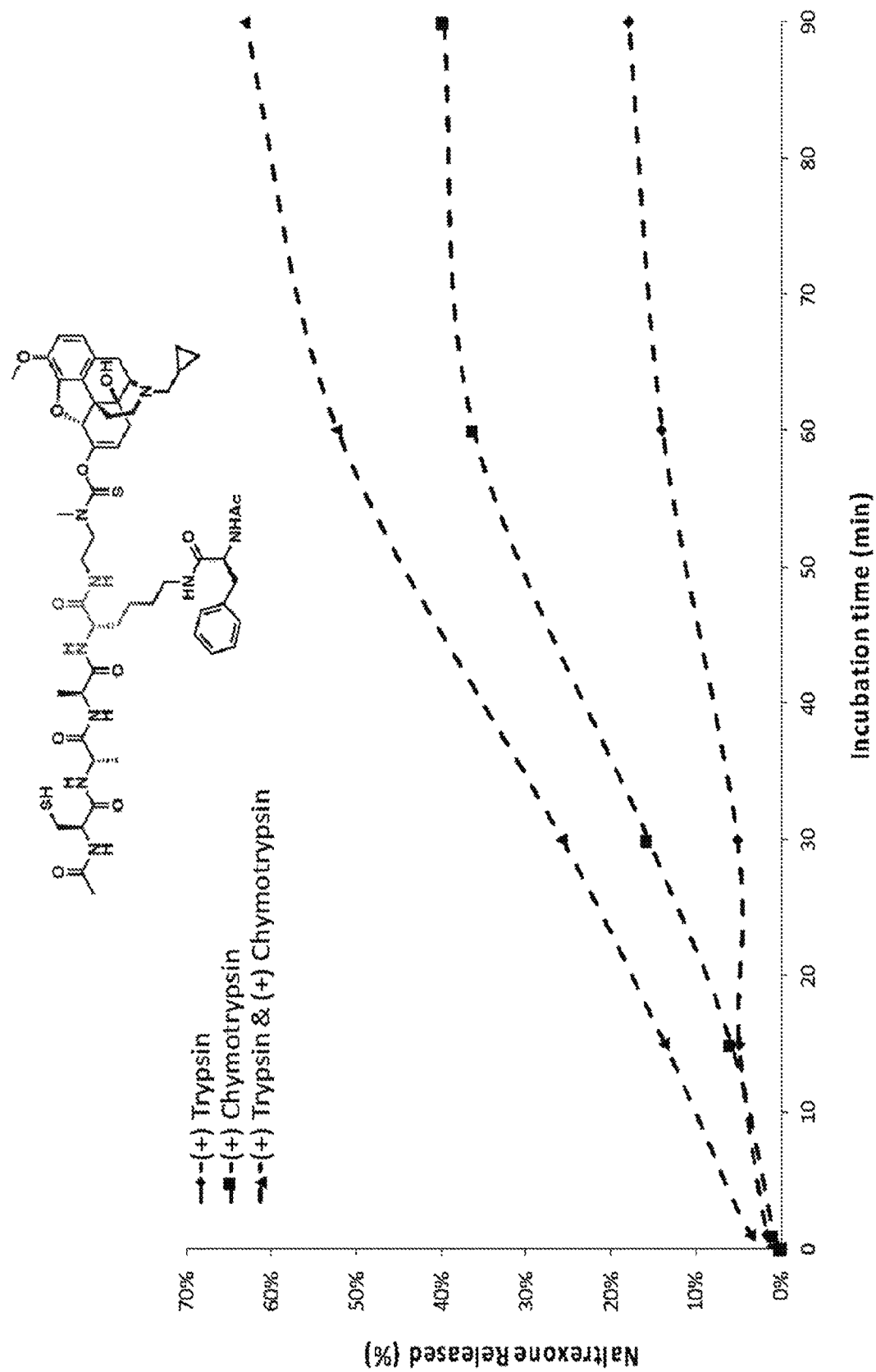
FIG. 21 is a graph showing that 2 mM CAAK(F)-diamino-Naltrexone (enol thionocarbamate-linked) (SEQ ID NO: 5) was incubated with trypsin and/or chymotrypsin for 90 minutes at 37° C.

FIG. 21 shows the results when 2 mM CAAK(F)-diamino-Naltrexone (enol thionocarbamate-linked) (SEQ ID NO: 4) was incubated with trypsin and/or chymotrypsin for 90 minutes at 37° C.

Figure 22:
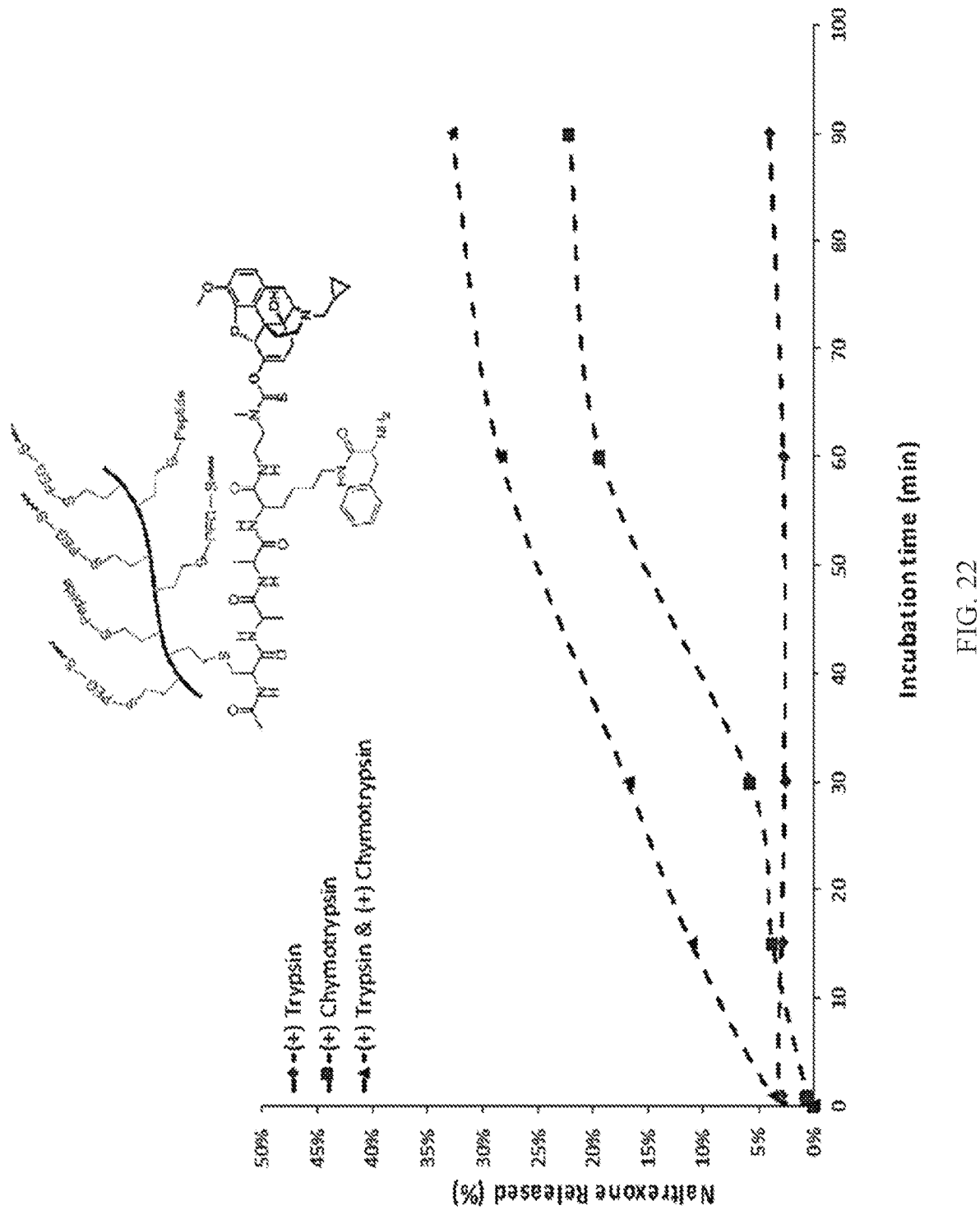
FIG. 22 is a graph showing that 2 mM Elastomer loaded with CAAK(F)-diamino-Naltrexone (enol thionocarbamate-linked) (SEQ ID NO: 5) was incubated with trypsin and/or chymotrypsin for 90 minutes at 37° C.

FIG. 22 shows the results when 2 mM Elastomer loaded with CAAK(F)-diamino-Naltrexone (enol thionocarbamate-linked) (SEQ ID NO: 4) was incubated with trypsin and/or chymotrypsin for 90 minutes at 37° C.

Unintended Naltrexone from Household Chemicals

The release of Naltrexone from Coca-Cola, Lemon Juice, and Vinegar was monitored using HPLC. Elastomer was incubated in the various substances with aliquots removed periodically over a 12-hour period and injected on a C18 column. There was no substantial release after incubation of the elastomer over a 12-hour time period. LCMS was run to confirm Naltrexone was not present in the 12-hour sample. The red box outlines the 0-Me Naltrexone peak, showing no presence across the 12-hour incubation period. The bottom trace shows injection of naltrexone in the various substances to demonstrate where it would appear if it was released.

Figure 23:
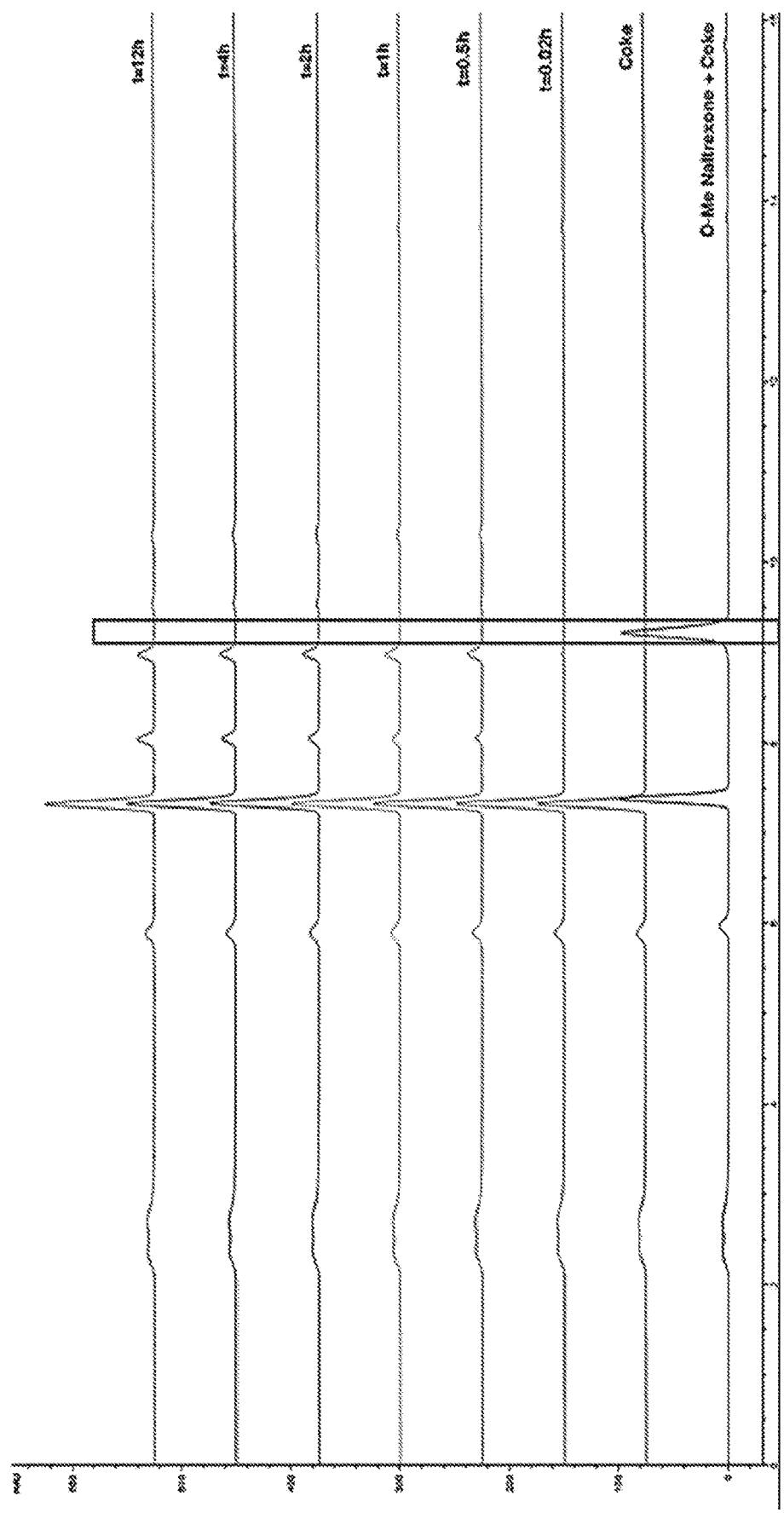
FIG. 23 is a graph showing the unintended release study from coca-cola measuring aliquots at 0, 0.02, 0.5, 1, 2, 4, and 12 hours. No appearance of Naltrexone was confirmed by LCMS.

FIG. 23 shows the unintended release study from coca-cola measuring aliquots at 0, 0.02, 0.5, 1, 2, 4, and 12 hours. No appearance of Naltrexone was confirmed by LCMS.

Figure 24:
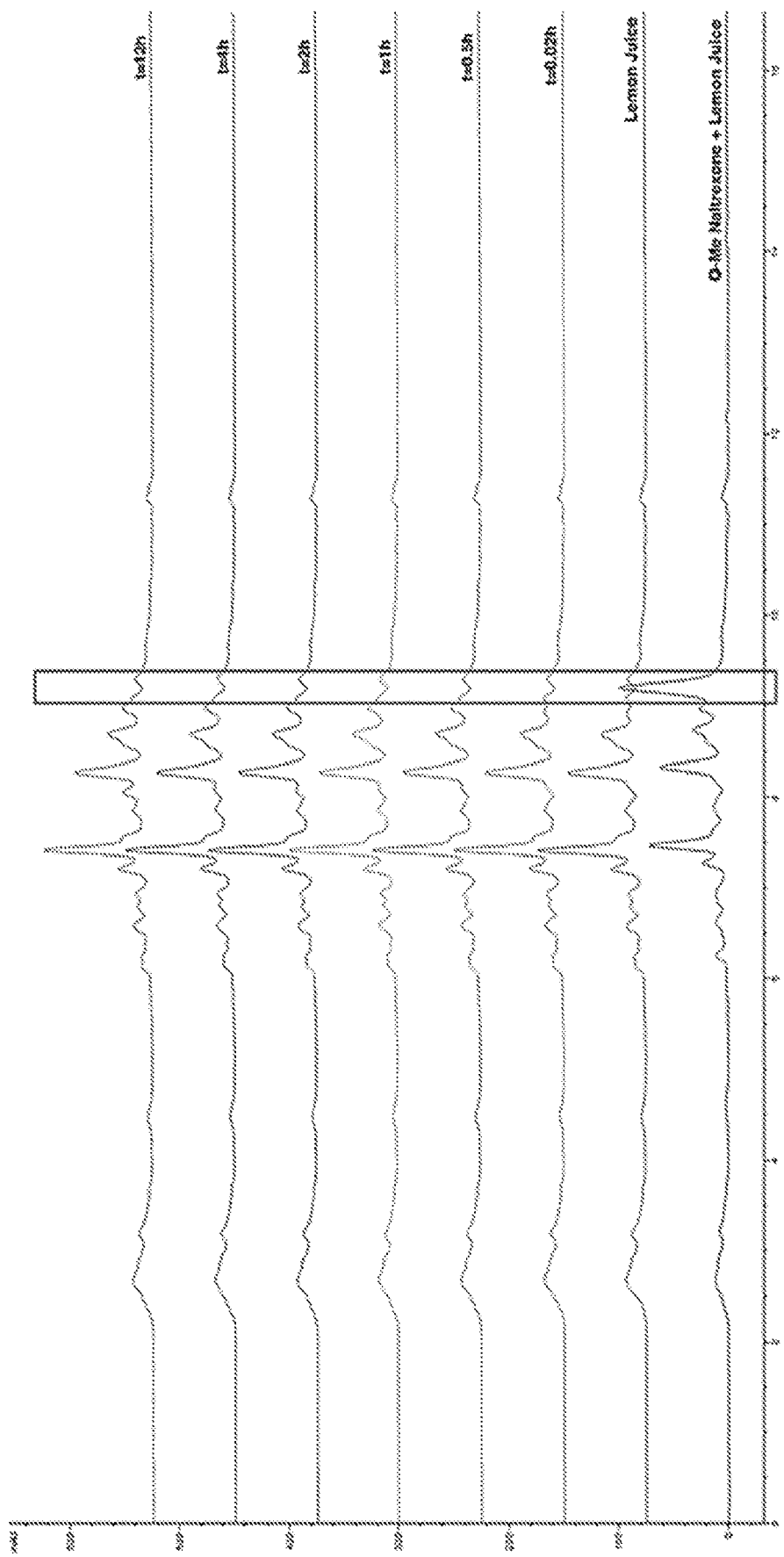
FIG. 24 is a graph showing the unintended release study from Lemon-Juice measuring aliquots at 0, 0.02, 0.5, 1, 2, 4, and 12 hours. No appearance of Naltrexone was confirmed by LCMS.

FIG. 24 shows the unintended release study from Lemon-Juice measuring aliquots at 0, 0.02, 0.5, 1, 2, 4, and 12 hours. No appearance of Naltrexone was confirmed by LCMS.

Figure 25:
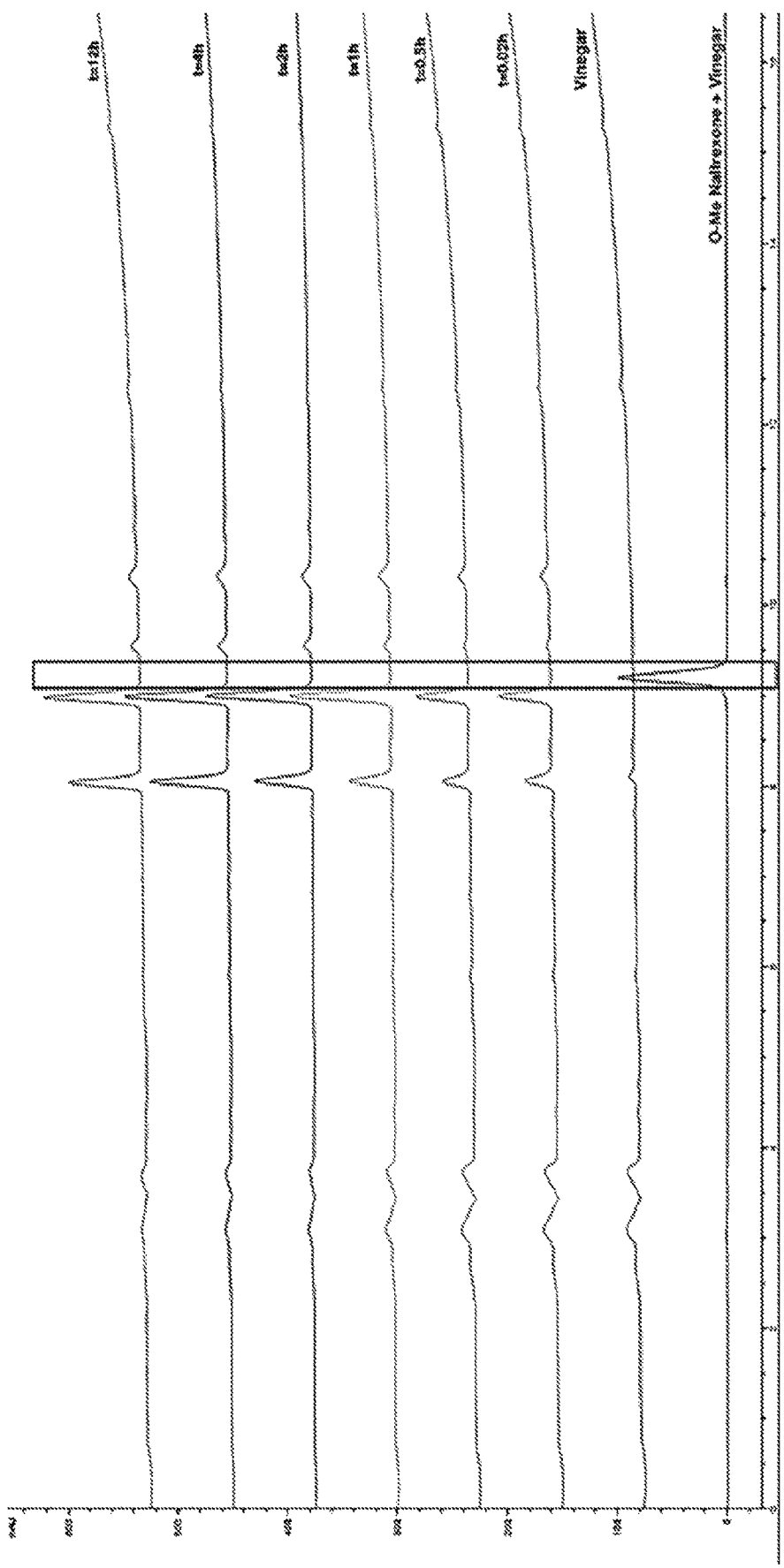
FIG. 25 is a graph showing the unintended release study from Vinegar measuring aliquots at 0, 0.02, 0.5, 1, 2, 4, and 12 hours. No appearance of Naltrexone was confirmed by LCMS.

FIG. 25 shows the unintended release study from Vinegar measuring aliquots at 0, 0.02, 0.5, 1, 2, 4, and 12 hours. No appearance of Naltrexone was confirmed by LCMS.

Animal Studies of Elastomer

LD50 of the elastomer was determined as greater than 5000 mg/kg according to the Organization for Economic Cooperation and Development (OECD) guideline. Briefly, the limit test at 5000 mg/kg dose was employed and the LD50 is determined to be greater than 5000 mg/kg after 3 animals survived over a 14-day observation. Sprague-Dawley rats (female, 4 weeks) were acclimated for 2 weeks prior to oral gavage of the elastomer (5000 mg/kg) suspended in phosphate-buffered saline. All rats survived the procedure for the full 14 days, after which they were euthanized.

Figure 26:
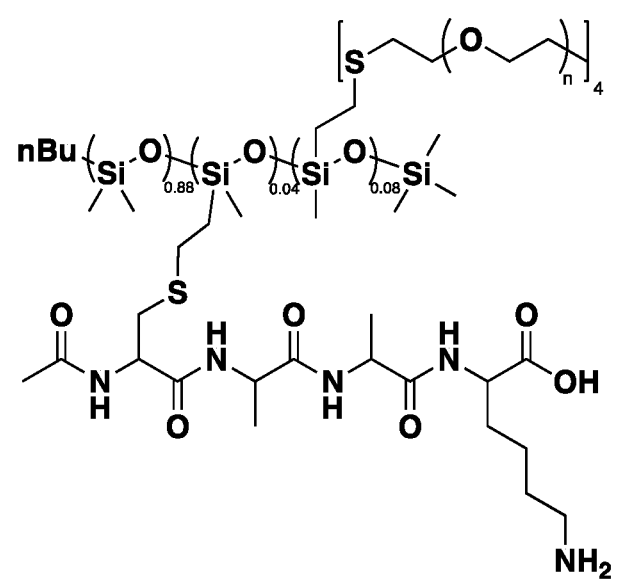
FIG. 26 is a formula showing the chemical structure of CAAK (SEQ ID NO: 9) functionalized elastomer used for animal toxicity studies.

FIG. 26 show the chemical structure of CAAK (SEQ ID NO: 9) functionalized elastomer used for animal toxicity studies.

Rat growth as measured by weight change is normal compared to the vendor data, showing that elastomers do not obstruct the GI tract. Note that one of the rats was slightly heavier than other rats prior to elastomer injection and grew faster, but it is within the natural weight variability and seems to stem from high liver enzyme value (see below for discussion).

Figure 27:
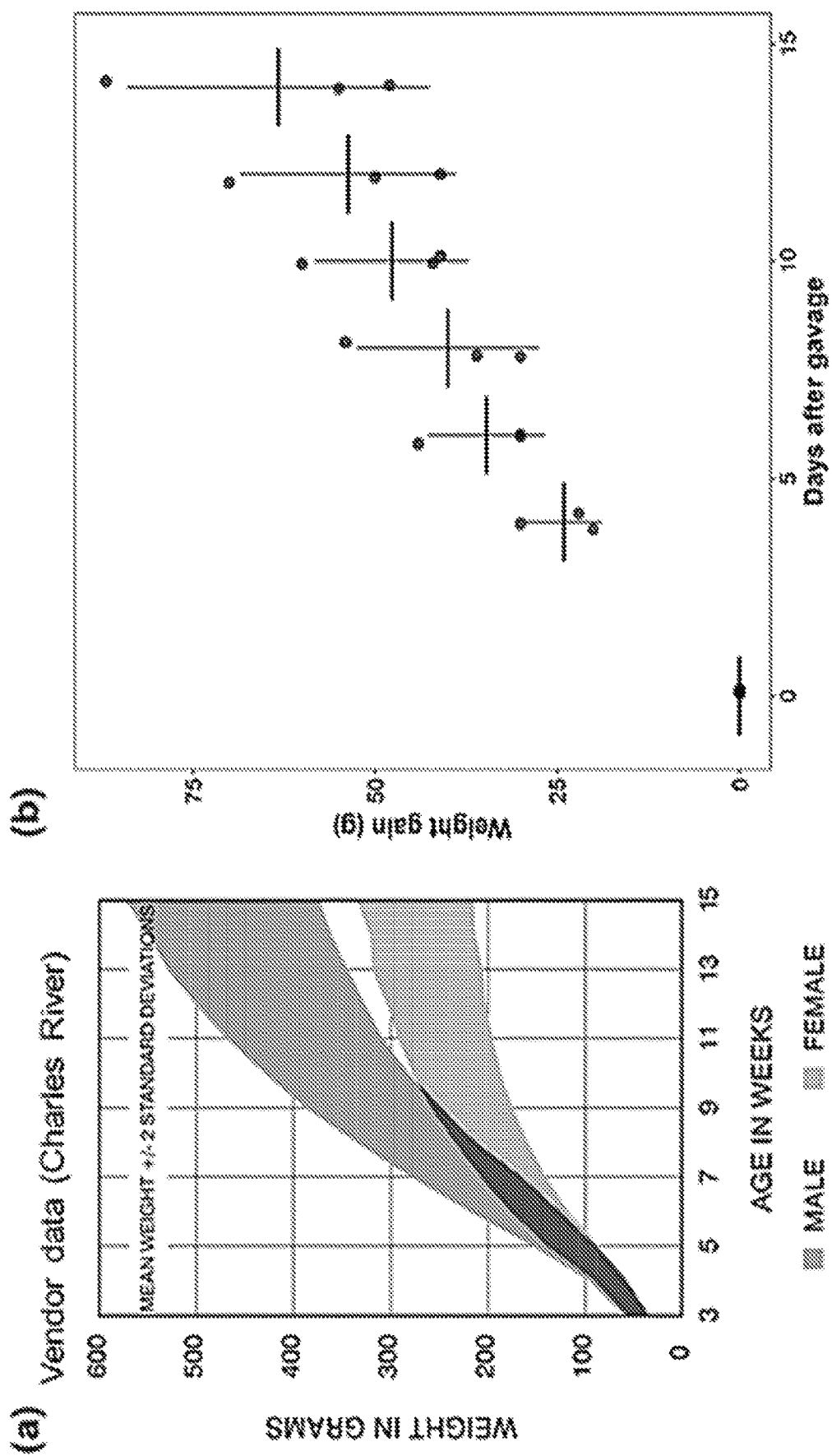
FIGS. 27A-B are a set of graphs showing the results when Rat weight change over time. (a) Normal rat growth curve provided by the vendor (Charles River), (b) weight gain after gavage (horizontal line: mean, vertical line: standard deviation).

FIG. 27 shows the results when rat weight change over time. (a) Normal rat growth curve provided by the vendor (Charles River), (b) weight gain after gavage (horizontal line: mean, vertical line: standard deviation).

Blood was collected from rats after oral gavage to test for liver and kidney toxicity as well as blood cell counts. Because serum chemistry results are relatively more variable, a baseline measurement was taken prior to oral gavage and tested for alanine aminotransferase (ALT) and aspartate aminotransferase (AST) activities as indicators for liver toxicity, and blood urea nitrogen (BUN) and creatinine (Creat) as indicators for kidney toxicity (Table 2). The pre-gavage data has shown that the heavier rat has slightly elevated ALT level (1.3 std. dev. above mean). Given that elevated ALT levels have been associated with obesity, the slightly higher weight of this rat may be due to its naturally high ALT level prior to the study.

TABLE 2

Baseline serum chemistry results prior to oral gavage.

| | ALT | AST | BUN | Creat |
|---|---|---|---|---|
| Rat 1 | 100 | 93 | 10 | 0.32 |
| Rat 2 | 67 | 112 | 9 | 0.43 |
| Rat 3 | 80 | 129 | 9 | 0.42 |
| Average | 82 ± 17 | 111 ± 18 | 9 ± 1 | 0.39 ± 0.06 |
| Normal | 57 ± 32 | 112 ± 65 | 13 ± 4 | 0.47 ± 0.10 |

ALT: alanine aminotransferase, AST: aspartate aminotransferase, BUN: blood urea nitrogen, Creat: creatinine. Normal values (mean ± standard deviation) are published by the vendor (Charles River).

The serum chemistry and blood counts conducted 14 days after oral gavage showed that the elastomer did not induce any noticeable changes in blood cells or liver/kidney function (Table 3).

TABLE 3

Serum chemistry and blood counts 14 days after oral gavage.

| | Liver enzymes | | Kidney function | | Blood cell counts | |
|---|---|---|---|---|---|---|
| | ALT | AST | BUN | Creat | WBC | RBC |
| Rat 1 | 70 | 82 | 16 | 0.43 | 8.9 | 7.04 |
| Rat 2 | 56 | 73 | 17 | 0.54 | 10.4 | 7.45 |
| Rat 3 | 63 | 87 | 18 | 0.54 | 8.8 | 8.21 |
| Average | 63 ± 7 | 81 ± 7 | 17 ± 1 | 0.50 ± 0.06 | 9.4 ± 0.90 | 7.57 ± 0.59 |
| Normal | 57 ± 32 | 112 ± 65 | 13 ± 4 | 0.47 ± 0.10 | 10.2 ± 3.7 | 7.37 ± 1.09 |

ALT: alanine aminotransferase, AST: aspartate aminotransferase, BUN: blood urea nitrogen, Creat: creatinine, WBC: white blood cell count, RBC: red blood cell count. Normal values (mean ± standard deviation) are published by the vendor (Charles River).

FIG. 28 shows other exemplary dual enzyme cleavable peptides according to certain embodiments of the present invention.

FIG. 29 shows other exemplary dual enzyme cleavable peptides conjugated to Naltrexone as an exemplary medication according to certain embodiments of the present invention. As discussed through this disclosure, naltrexone is used as a model compound of opioids and X=S or O; R=H, Acetamide, Protecting group, Amino acid or Peptide.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth. Throughout the disclosure, naltrexone is used as a model drug due to its structural similarity to many opioids.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modification forms thereof as come within the scope of the following claims.

REFERENCES CITED 1. (a) J. Rautio, H. Kumpulainen, T. Heimbach, R. Oliyai, D. Oh, T. Jarvinen and J. Savolainen, Nat. Rev. Drug Discov., 2008, 7, 255-270; (b) J. M. Hu, G. Q. Zhang and S. Y. Liu, Chem. Soc. Rev., 2012, 41, 5933-5949.
2. (a) X. Tian, K. H. Baek and I. Shin, Chem. Sci., 2013, 4, 947-956; (b) K. S. Tucking, V. Grutzner, R. E. Unger and H. Schonherr, Macromol. Rapid Commun., 2015, 36, 1248-1254; (c) D. Wegener, F. Wirsching, D. Riester and A. Schwienhorst, Chem. Biol., 2003, 10, 61-68; (d) R. Huang, X. J. Wang, D. L. Wang, F. Liu, B. Mei, A. M. Tang, J. Jiang and G. L. Liang, Anal. Chem., 2013, 85, 6203-6207.
3. G. C. Van de Bittner, C. R. Bertozzi and C. J. Chang, J. Am. Chem. Soc., 2013, 135, 1783-1795.
4. S. Y. Li, L. H. Liu, H. Cheng, B. Li, W. X. Qiu and X. Z. Zhang, Chem. Commun., 2015, 51, 14520-14523.
5. (a) M. P. C. Mulder, K. Witting, I. Berlin, J. N. Pruneda, K. P. Wu, J. G. Chang, R. Merkx, J. Bialas, M. Groettrup, A. C. O. Vertegaal, B. A. Schulman, D. Komander, J. Neefjes, F. El Oualid and H. Ovaa, Nat. Chem. Biol., 2016, 12, 523-533; (b) R. J. R. W. Peters, M. Marguet, S. Marais, M. W. Fraaije, J. C. M. Van Hest and S. Lecommandoux, Angew. Chem. Int. Ed., 2014, 53, 146-150.
6. (a) T. Ohta, T. Terada, T. Nagakawa, H. Tajima, H. Itoh, L. Fonseca and I. Miyazaki, Br. J. Cancer, 1994, 69, 152-156; (b) S. T. Vilen, J. Suojanen, F. Salas, J. Risteli, M. Ylipalosaari, O. Itkonen, H. Koistinen, M. Baumann, U. H. Stenman, T. Sorsa, T. Salo and P. Nyberg, Cancer Invest., 2012, 30, 583-592; (c) E. Koivunen, O. Itkonen, H. Halila and U. H. Stenman, Cancer Res., 1990, 50, 2375-2378; (d) K. Radhakrishnan, J. Tripathy, D. P. Gnanadhas, D. Chakravortty and A. M. Raichur, RSC Adv., 2014, 4, 45961-45968; (e) M. Van Dijk, M. L. Nollet, P. Weijers, A. C. Dechesne, C. F. van Nostrum, W. E. Hennink, D. T. S. Rijkers and R. M. J. Liskamp, Biomacromolecules, 2008, 9, 2834-2843.
7. N. Chen, J. Zou, S. M. Wang, Y. M. Ye, Y. Huang, G. Gadda and J. J. Yang, Biochemistry, 2009, 48, 3519-3526.
8. R. Moorman-Li, C. A. Motycka, L. D. Inge, J. M. Congdon, S. Hobson and B. Pokropski, P&T 2012, 37, 412-418.
9. J. V. Olsen, S. E. Ong and M. Mann, Mol. Cell. Proteomics, 2004, 3, 608-614.
10. B. M. Zee and B. A. Garcia, Essays Biochem., 2012, 52, 147-163.
11. C. Roessler, C. Tuting, M. Meleshin, C. Steegborn and M. Schutkowski, J. Med. Chem., 2015, 58, 7217-7223.
12. R. B. Merrifield, J. Am. Chem. Soc., 1963, 85, 2149-2154.
13. B. C. Gorske, B. L. Bastian, G. D. Geske and H. E. Blackwell, J. Am. Chem. Soc., 2007, 129, 8928-8929.
14. W. Appel, Clin. Biochem., 1986, 19, 317-322.
15. P. E. Groleau, S. F. Gauthier and Y. Pouliot, Int. Dairy J., 2003, 13, 887-895.
16. G. Lowe and Y. Yuthavong, Biochem. J., 1971, 124, 107-115.
17. (a) G. I. Tesser, M. Gruber and R. J. F. Nivard, Biochim. Biophys. Acta, 1964, 89, 303-308;
18. (b) N. E. Mackenzie, J. P. G. Malthouse and A. I. Scott, Biochem. J., 1985, 226, 601-606.
18. H. R. Stennicke and G. S. Salvesan, J. Biol. Chem., 1997, 272, 25719-25723.
19. (a) E. Devarajan, A. A. Sahin, J. S. Chen, R. R. Krishnamurthy, N. Aggarwal, A. M. Brun, A.
20. Sapino, F. Zhang, D. Sharma, X. H. Yang, A. D. Tora and K. Mehta, Oncogene, 2002, 21, 8843-8851; (b) S. Fulda, Cancer Lett., 2009, 281, 128-133.
21. M. Agosto, M. Azrin, K. Singh, A. S. Jaffe and B. T. Liang, J. Am. Coll. Cardiol., 2011, 57, 220-221.

21. M. Olsson and B. Zhivotovsky, Cell Death Differ., 2011, 18, 1441-1449.
22. H. R. Stennicke, M. Renatus, M. Meldal and G. S. Salvesen, Biochem. J., 2000, 350, 563-568.
23. Gorske, B. C.; Bastian, B. L.; Geske, G. D.; Blackwell, H. E. J. Am. Chem. Soc. 2007, 129, 8928-8929.
24. Lauer, J. L.; Fields, C. G.; Fields, G. B. Lett. Pept. Sci. 1994, 1, 197-205.

We claim:

1. An enzyme-responsive peptide, wherein the enzyme-responsive peptide has a general structure of:

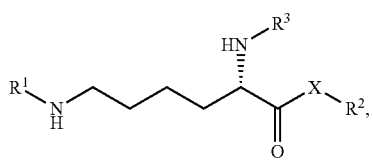

wherein X is selected from O, NH or S; $R^1$ is an enzyme substrate, wherein $R^1$ is a protease substrate selected from the group consisting of a chymotrypsin substrate, a papain substrate, a caspase 8 substrate and a caspase 3 substrate; $R^2$ comprises a reporter molecule or an active ingredient; and $R^3$ is selected from a protecting group, a H, an amino acid or a peptide, wherein the enzyme-responsive peptide requires digestion by two separate enzymes to cleave a bond between the α-carboxylic acid and X—$R^2$ to release $R^2$, wherein the enzyme-responsive peptide requires digestion by a first enzyme selected from the group consisting of chymotrypsin, a papain, caspase 8 and caspase 3 and by a second enzyme, wherein the second enzyme is trypsin.

2. The enzyme-responsive peptide of claim 1, wherein X is NH.

3. The enzyme-responsive peptide of claim 1, wherein $R^2$ is a reporter molecule.

4. The enzyme-responsive peptide of claim 1, wherein $R^2$ is an active ingredient.

5. The enzyme-responsive peptide of claim 1, wherein $R^3$ is a protecting group.

6. The enzyme-responsive peptide of claim 1, wherein the enzyme-responsive peptide requires digestion by the first enzyme and subsequently by the second enzyme.

7. The enzyme-responsive peptide of claim 1, wherein $R^3$ comprises cysteine conjugated to a siloxane polymer.

8. The enzyme-responsive peptide of claim 1, wherein $R^3$ comprises CAA.

9. The enzyme-responsive peptide of claim 1, wherein $R^1$ comprises F, FG, AAF, or DEVD (SEQ ID NO: 7).

10. The enzyme-responsive peptide of claim 8, wherein the enzyme-responsive peptide comprises the compound of formula

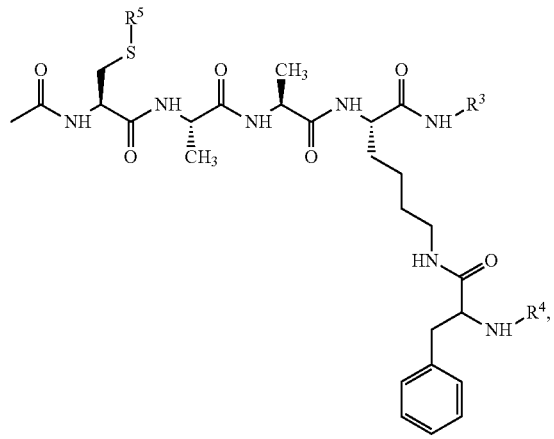

wherein $R^4$ is H, acetamide, a protecting group, an amino acid, or a peptide and wherein $R^5$ is H, a thiol protecting group, or a siloxane polymer.

11. The enzyme-responsive peptide of claim 1, wherein $R^2$ comprises the reporter molecule or the active ingredient conjugated through a carbamate linker or a thionocarbamate linker.

12. The enzyme-responsive peptide of claim 11, wherein the enzyme-responsive peptide comprises the compound of formula

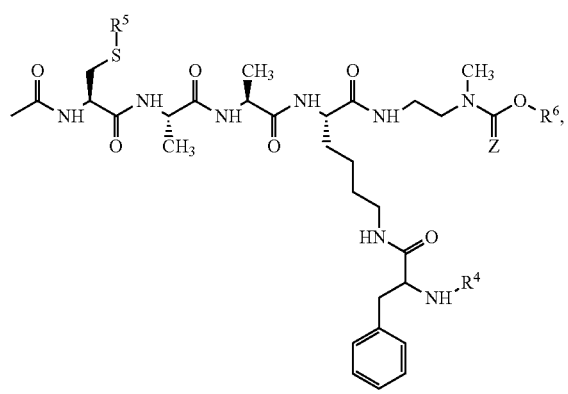

wherein $R^4$ is H, acetamide, a protecting group, an amino acid, or a peptide, wherein $R^5$ is H, a thiol protecting group, or a siloxane polymer, wherein Z is selected from O and S, and wherein $R^6$ is the reporter molecule or the active ingredient conjugated through the carbamate linker or the thionocarbamate linker.

13. A polymeric formulation for controlled releasing an active ingredient, the formulation comprising the enzyme-responsive peptide of claim 1.

14. A method for controlled releasing an active ingredient, wherein the method comprising the steps of
(1) contacting a compound having a general structure of

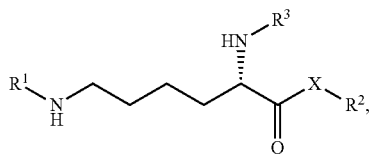

wherein X is selected from O, NH or S; $R^1$ is an enzyme substrate, wherein $R^1$ is a protease substrate selected from the group consisting of a chymotrypsin substrate, a papain substrate, a caspase 8 substrate and a caspase 3 substrate; $R^2$ comprises an active ingredient; and $R^3$ is selected from a protecting group, a H, an amino acid or a peptide; with a first enzyme, wherein $R^1$ is cleaved from the compound upon digestion by the first enzyme to form a second compound with a free ε-amine group; and (2) contacting the second compound with a second enzyme, wherein the active ingredient is released from the second compound upon digestion of the second enzyme—wherein the enzyme-responsive peptide requires digestion by a first enzyme selected from the group consisting of chymotrypsin, a papain, caspase 8 and caspase 3 and by a second enzyme, wherein the second enzyme is trypsin.

15. The method of claim 14, wherein $R^3$ is a protecting group.

16. The method of claim 14, wherein the first enzyme is a chymotrypsin.

17. The method of claim 14, wherein the first enzyme is papain.

18. The method of claim 14, wherein the first enzyme is a caspase 8.

19. The method of claim 14, wherein the first enzyme is caspase 3.

* * * * *